United States Patent
Li et al.

(10) Patent No.: US 9,309,566 B2
(45) Date of Patent: *Apr. 12, 2016

(54) METHODS, COMPOSITIONS, SYSTEMS, APPARATUSES AND KITS FOR NUCLEIC ACID AMPLIFICATION

(71) Applicant: LIFE TECHNOLOGIES CORPORATION, Carlsbad, CA (US)

(72) Inventors: Bin Li, Palo Alto, CA (US); Kai Qin Lao, Pleasanton, CA (US); Jennifer O'Neil, Peabody, MA (US); Jennifer Kunkel, Amesbury, MA (US); Kellie Haley, Peabody, MA (US); Rachel Kasinskas, Amesbury, MA (US); Zhaochun Ma, Sunnyvale, CA (US); Pius Brzoska, Woodside, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/828,049

(22) Filed: Mar. 14, 2013

(65) Prior Publication Data

US 2013/0203607 A1    Aug. 8, 2013

Related U.S. Application Data

(63) Continuation-in-part of application No. 13/328,844, filed on Dec. 16, 2011, which is a continuation-in-part of application No. PCT/US2011/065535, filed on Dec. 16, 2011.

(60) Provisional application No. 61/692,830, filed on Aug. 24, 2012, provisional application No. 61/424,599, filed on Dec. 17, 2010, provisional application No. 61/445,324, filed on Feb. 22, 2011, provisional application No. 61/451,919, filed on Mar. 11, 2011, provisional application No. 61/526,478, filed on Aug. 23, 2011, provisional application No. 61/552,660, filed on Oct. 28, 2011.

(51) Int. Cl.
C12Q 1/68    (2006.01)

(52) U.S. Cl.
CPC ............ *C12Q 1/6853* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 5,223,414 A | 6/1993 | Zarling et al. |
| 5,616,478 A | 4/1997 | Chetverin et al. |
| 5,670,325 A | 9/1997 | Lapidus et al. |
| 5,928,870 A | 7/1999 | Lapidus et al. |
| 5,958,698 A | 9/1999 | Chetverin et al. |
| 6,001,568 A | 12/1999 | Chetverin et al. |
| 6,033,881 A | 3/2000 | Himmler et al. |
| 6,074,853 A | 6/2000 | Pati et al. |
| 6,306,590 B1 | 10/2001 | Mehta et al. |
| 6,432,360 B1 | 8/2002 | Church |
| 6,440,706 B1 | 8/2002 | Vogelstein et al. |
| 6,511,803 B1 | 1/2003 | Church et al. |
| 6,929,915 B2 | 8/2005 | Benkovic et al. |
| 7,270,981 B2 | 9/2007 | Armes et al. |
| 7,282,337 B1 | 10/2007 | Harris |
| 7,399,590 B2 | 7/2008 | Piepenburg et al. |
| 7,432,055 B2 | 10/2008 | Pemov et al. |
| 7,435,561 B2 | 10/2008 | Piepenburg et al. |
| 7,485,428 B2 | 2/2009 | Armes et al. |
| 7,604,940 B1 | 10/2009 | Voss |
| 7,666,598 B2 | 2/2010 | Piepenburg et al. |
| 7,723,031 B2 | 5/2010 | Benkovic et al. |
| 7,763,427 B2 | 7/2010 | Piepenburg et al. |
| 7,785,790 B1 | 8/2010 | Church et al. |
| 7,824,889 B2 | 11/2010 | Vogelstein et al. |
| 7,906,279 B2 | 3/2011 | Benkovic et al. |
| 7,915,015 B2 | 3/2011 | Vogelstein et al. |
| 7,985,565 B2 | 7/2011 | Mayer et al. |
| 8,017,339 B2 | 9/2011 | Piepenburg et al. |
| 8,030,000 B2 | 10/2011 | Piepenburg et al. |
| 8,062,850 B2 | 11/2011 | Piepenburg et al. |
| 8,071,308 B2 | 12/2011 | Piepenburg et al. |
| 8,124,342 B2 | 2/2012 | Benkovic et al. |
| 8,129,116 B2 | 3/2012 | Benkovic et al. |
| 8,137,913 B2 | 3/2012 | Benkovic et al. |

(Continued)

FOREIGN PATENT DOCUMENTS

| | | |
|---|---|---|
| CN | 1489632 A2 | 4/2004 |
| CN | 101413034 B | 2/2011 |

(Continued)

OTHER PUBLICATIONS

Fujimoto et al. (Site-Specific Cytosine to Uracil Transition by Using Reversible DNA Photo-crosslinking, ChemBioChem 2010, 11, 1661-1664).*

(Continued)

*Primary Examiner* — Stephanie K Mummert
*Assistant Examiner* — Aaron Priest

(57) ABSTRACT

In some embodiments, the present teachings provide methods for paired end sequencing. In some embodiment, a polynucleotide template to be subjected to paired end sequencing comprises at least one cross linking moiety and at least one scissile moiety. In some embodiments, a paired end sequencing reaction comprises (a) a forward sequencing step, (b) a cleavage step, and (c) a reverse sequencing step. In some embodiments, a paired end sequencing reaction comprises (a) a forward sequencing step, (b) a cross-linking step, (c) a cleavage step, and (d) a reverse sequencing step.

19 Claims, 11 Drawing Sheets

(56) References Cited

U.S. PATENT DOCUMENTS

| | | | |
|---|---|---|---|
| 8,143,008 B2 | 3/2012 | Kawashima et al. | |
| 8,241,851 B2 | 8/2012 | Benkovic et al. | |
| 8,361,718 B2 | 1/2013 | Benkovic et al. | |
| 8,389,216 B2 | 3/2013 | Benkovic et al. | |
| 8,426,134 B2 | 4/2013 | Piepenburg et al. | |
| 8,460,875 B2 | 6/2013 | Armes et al. | |
| 8,476,022 B2 | 7/2013 | Ronaghi et al. | |
| 8,652,810 B2 | 2/2014 | Adessi et al. | |
| 8,673,561 B2 | 3/2014 | Benkovic et al. | |
| 8,759,000 B2 | 6/2014 | Benkovic et al. | |
| 8,765,374 B2 | 7/2014 | Benkovic et al. | |
| 8,895,249 B2 | 11/2014 | Shen et al. | |
| 2003/0143525 A1 | 7/2003 | Benkovic et al. | |
| 2003/0219792 A1 | 11/2003 | Armes et al. | |
| 2004/0171060 A1 | 9/2004 | Benkovic et al. | |
| 2005/0100900 A1 | 5/2005 | Kawashima et al. | |
| 2006/0269934 A1 | 11/2006 | Woudenberg et al. | |
| 2007/0054296 A1 | 3/2007 | Piepenburg et al. | |
| 2008/0009420 A1 | 1/2008 | Schroth et al. | |
| 2008/0166727 A1 | 7/2008 | Esfandyarpour et al. | |
| 2009/0093378 A1* | 4/2009 | Bignell et al. | 506/23 |
| 2009/0127589 A1 | 5/2009 | Rothberg et al. | |
| 2009/0171078 A1 | 7/2009 | Lao et al. | |
| 2009/0203531 A1 | 8/2009 | Kurn | |
| 2009/0286286 A1 | 11/2009 | Lim | |
| 2009/0325165 A1 | 12/2009 | Armes et al. | |
| 2010/0136544 A1 | 6/2010 | Agresti et al. | |
| 2010/0167954 A1 | 7/2010 | Earnshaw et al. | |
| 2010/0304982 A1 | 12/2010 | Hinz et al. | |
| 2011/0065106 A1 | 3/2011 | Armes et al. | |
| 2011/0123991 A1 | 5/2011 | Hoser | |
| 2012/0015367 A1 | 1/2012 | Piepenburg et al. | |
| 2012/0053063 A1 | 3/2012 | Rigatti et al. | |
| 2012/0058517 A1 | 3/2012 | Piepenburg et al. | |
| 2012/0082990 A1 | 4/2012 | Piepenburg et al. | |
| 2012/0129173 A1 | 5/2012 | Piepenburg et al. | |
| 2012/0156728 A1 | 6/2012 | Li et al. | |
| 2012/0172259 A1 | 7/2012 | Rigatti | |
| 2012/0258456 A1 | 10/2012 | Armes et al. | |
| 2012/0258499 A1 | 10/2012 | Piepenburg et al. | |
| 2012/0264132 A1 | 10/2012 | Ismagilov et al. | |
| 2013/0012399 A1* | 1/2013 | Myers et al. | 506/2 |
| 2013/0210008 A1 | 8/2013 | Feitsma et al. | |
| 2014/0228254 A1 | 8/2014 | Adessi et al. | |

FOREIGN PATENT DOCUMENTS

| | | |
|---|---|---|
| EP | 1275737 A2 | 1/2003 |
| JP | 2003-510012 | 3/2003 |
| JP | 2004-524012 | 8/2004 |
| JP | 2004-535162 | 11/2004 |
| WO | WO-94/03624 | 2/1994 |
| WO | WO-98/08975 | 3/1998 |
| WO | WO-98/44151 | 10/1998 |
| WO | WO-00/18957 | 4/2000 |
| WO | WO-00/47767 | 8/2000 |
| WO | WO-00/60919 A2 | 10/2000 |
| WO | WO0060919 | 10/2000 |
| WO | WO-01/81908 | 11/2001 |
| WO | WO-02/46456 A1 | 6/2002 |
| WO | WO-02/072772 A2 | 9/2002 |
| WO | WO-03/072805 | 9/2003 |
| WO | WO-2005/007796 | 1/2005 |
| WO | WO-2006/099579 A2 | 9/2006 |
| WO | WO-2007/010252 | 1/2007 |
| WO | WO-2007/107710 | 9/2007 |
| WO | WO-2008/041002 | 4/2008 |
| WO | WO-2009/102878 A2 | 8/2009 |
| WO | WO-2011/106368 A2 | 9/2011 |
| WO | WO-2011/106368 A3 | 9/2011 |
| WO | WO-2011/106460 | 9/2011 |
| WO | WO-2012/083189 A2 | 6/2012 |
| WO | WO-2012/083189 A3 | 6/2012 |
| WO | WO-2012/106072 A2 | 8/2012 |
| WO | WO-2013/019361 | 2/2013 |
| WO | WO-2013/045700 | 4/2013 |

OTHER PUBLICATIONS

PCT/US2011/065535, International Search Report mailed Jul. 4, 2012, 5.

PCT/US2011/065535, International Preliminary Report on Patentability issued Jun. 18, 2013, 8.

PCT/US2013/059093, International Search Report and Written Opinion mailed Jan. 22, 2014, 12.

Bentley, D et al., "Accurate whole human genome sequencing using reversible terminator chemistry", Nature, vol. 456(6), (7218), 2008, pp. 53-59.

Borer, Philip N. et al., "Stability of Ribonucleic acid Double-stranded Helices", J. Mol. Biol. 86, 843-853, 1974, 843-853.

Brewood, Greg P. et al., "Electrical detection of the temperature induced melting transition of a DNA hairpin covalently attached to gold interdigitated microelectrodes", Nucleic Acids Research, 2008, vol. 36(15):e98, Jul. 15, 2008.

Meunier-Prest, Rita et al., "Direct Measurement of the Melting Temperature of Supported DNA by Electrochemical Method", Nucleic Acids Research, vol. 31(23):e150, Dec. 1, 2003, e150.

Morrison, et al., "Nanoliter High Throughput Quantitative PCR", Nucleic Acids Research, vol.34, No. 18, e123, 2006, 1-9.

Oyola, Samuel et al., "Optimizing illumina next-generation sequencing library preparation for extremely at-biased genomes", BMC Genomics, 13:1, 2012, 1-12.

PCT/US2013/031589, International Search Report and Written Opinion mailed Jun. 25, 2013, 12.

PCT/US2013/032598, International Search Report and Written Opinion mailed Jun. 11, 2013.

Piepenburg, Olaf et al., "DNA Detection Using Recombination Proteins", PLoS Biology, vol. 4, issue 7 e204, Jul. 2006, 1115-1121.

Rychlik, Wojciech et al., "A computer program for choosing optimal oligonucleotides for filter hybridization, sequencing and in vitro amplification of DNA", Nuc. Acids Res., 1989, vol.17(21):8543-8551, vol. 17, No. 21, 1989, 8543-8551.

Santalucia, John, "A unified view of polymer, dumbbell, and oligonucleotide DNA nearest-neighbor thermodynamics", Biochemistry, vol. 95, Proceedings of the National Academy of Sciences, USA, Feb. 1998, 1460-1465.

Sato, Kae et al., "Microbead-based rolling circle amplification in a microchip for sensitive DNA detection", Lab Chip, 10, 2010, 1262-1266.

Shapero, Michael et al., "SNP Genotyping by Multiplexed Solid-Phase Amplification and Fluorescent Minisequencing", Genome Research, 11, 2001, 1926-1934.

Shen, Feng et al., "Digital Isothermal Quantification of Nucleic Acids via Simultaneous Chemical Initiation of Recombinase Polymerase Amplification Reactions on SlipChip", Anal. Chem., 83, 2011, 3533-3540.

Shendure, Jay et al., "Next-generation DNA sequencing", Next-generation DNA sequencing, vol. 26, No. 10, Oct. 2008, 1135-1145.

Shigemori, Yasushi et al., "Multiplex PCR: use of heat-stable Thermus thermophilus RecA protein to minimize non-specific PCR products", Nucleic Acids Research, vol. 33, No. 14, e126, 2005, 1-9.

Spink, Charles H., "Differential Scanning Calorimetry", Methods Cell Biol. (2008) 84:115-141, 2008, 115-141.

Xu, Ming Y. et al., "Dual primer emulsion PCR for next-generation DNA sequencing", BioTechniques, vol. 48, No. 5, 2010, 409-412.

PCT/US2013/032598, International Preliminary Report on Patentability mailed on Oct. 30, 2014, 7 pages.

Mardis, E., "Next-generation DNA sequencing methods", Annual Review of Genomics and Human Genetetics, vol. 9, Jan. 1, 2008, 387-402.

Mitra, R et al., "Digital genotyping and haplotyping with polymerase colonies", PNAS, vol. 100(10), 2003, 5926-5931.

Mitterer, G. et al., "Microarray-Based Detection of Bacteria by On-Chip PCR", Methods in Molecular Biology, vol. 345, 2006, 37-51.

Moorthie, S. et al., "Review of massively parallel DNA sequencing technologies", Hugo J, vol. 5, Oct. 27, 2011, 1-2.

(56) References Cited

OTHER PUBLICATIONS

PCT/US2014/026735, International Search Report and Written Opinion mailed Sep. 5, 2014, 15 Pages.
Schadt, E. et al., "A window into third-generation sequencing", *Human Molecular Genetics*, vol. 19 (2), Sep. 21, 2010, R227-R240.
Von Nickisch-Rosenegk, M. et al., "On-chip PCR amplification of very long templates using immobilized primers on glassy surfaces", *Biosensors & Bioelectronics*, vol. 20, 2005, 1491-1498.
Abrams, Ezra et al., "Bridge Amplification for DNA-based Diagnostics", Chapter 1.9, 1997, 171-189.
Adessi, C et al., "Solid Phase DNA Amplification: characterisation of primer attachment and amplification mechanisms", *Nucleic Acids Research*, vol. 28, No. 20, e87, 2000, 1-8.
Andreadis, Joanne D. et al., "Use of immobilized PCR primers to generate covalently immobilized DNAs for in vitro transcription/translation reactions", *Nucleic Acids Research*, vol. 28, No. 2, 2000, e5.
Andresen, Dennie et al., "Helicase dependent OnChip-amplification and its use in multiplex pathogen detection", *Clinica Chimica Acta*, 403, Mar. 18, 2009, 244-248.
Andresen, Dennie et al., "Helicase-dependent amplification: use in OnChip amplification and potential for point-of-care diagnostics", *Expert Rev. Mol. Diagn.*, 9(7), Oct. 2009, 645-650.
Belanger, Karyn et al., "Bacteriophage T4 Initiates Bidirectional DNA Replication through a Two-Step Process", *Molecular Cell*, vol. 2, 1998, 693-701.
Bing, David et al., "Bridge Amplification: A Solid Phase PCR System for the Amplification and Detection of Allelic Differences in Single Copy Genes", *Genetic Identity Conference Proceedings, Seventh International Symposium on Human Identification*, 1996.
Chetverin, Alexander et al., "Oligonucleotide Arrays: New Concepts and Possibilities", *Bio/Technology*, vol. 12, Nov. 12, 1994, 1093-1099.
Dubiley, Svetlana et al., "Polymorphism analysis and gene detection by minisequencing on an array of gel-immobilized primers", *Nucleic Acids Research*, vol. 27, No. 18, 1999, e19.
Formosa, Timothy et al., "DNA Synthesis Dependent on Genetic Recombination: Characterization of a Reaction Catalyzed by Purified Bacteriophage T4 Proteins", *Cell*, vol. 47, 1986, 793-806.
Meuzelaar, Linda et al., "MegaPlex PCR: a strategy for multiplex amplification", *Nature Methods*, vol. 4, No. 10, Oct. 2007, 835-837.
Morrical, Scott et al., "Amplification of Snap-back DNA Synthesis Reactions by the uvsX Recombinase of Bacteriophage T4", *The Journal of Biological Chemistry*, vol. 266, No. 21, 1991, 14031-14038.
PCT/EP01/14369, International Search Report mailed Mar. 13, 2002, 3 pages.
PCT/US2014/026735, Partial Search Report, Jun. 25, 2014, 8 pages.
Pemov, A.et al., "DNA analysis with multiplex microarray-enhanced PCR", *Nucleic Acids Research*, vol. 33, No. 2, 2005, 1-9.
Pourmand, N et al., "Direct electrical detection of DNA synthesis", *PNAS*, vol. 103(17), 2006, pp. 6466-6470.
Rehman, F. et al., "Immobilization of Acrylamide-modified Oligonucleotides by Co-polymerization", *Nucleic Acids Research*, vol. 27, No. 2, 1999, pp. 649-655.
Rothberg, J. et al., "An integrated semiconductor device enabling non-optical genome sequencing", *Nature*, vol. 475, No. 7356, Jul. 21, 2011, pp. 348-352.
Walker, et al., "Strand displacement amplification—an isothermal, in vitro DNA amplification technique", *Nucleic Acids Research*, vol. 20, Issue 7,, 1992, 1691-1696.
Walter, Nils et al., "Strand displacement amplification as an in vitro model for rolling-circle replication: Deletion formation and evolution during serial transfer", *Proc. Natl. Acad. Sci. USA*, vol. 91, Aug. 1994, 7937-7941.
Yershov, et al., "DNA Analysis and Diagnostics on Oligonucleotide Microchips", *Proc. Natl. Acad. Sci. USA 93*, 1996, 4913-4918.
Ma, Zhaochun et al., "Isothermal amplification method for next-generation sequencing", *PNAS*, vol. 110, No. 5, Aug. 27, 2013, 14320-14323.
Mitra, Robi et al., "In situ localized amplification and contact replication of many individual DNA molecules", *Nuc Acids Res*, vol. 27(24), 1999, e34, pp. i-vi.
"Oligo Calc: Oligonucleotide Properties Calculator", *Northwestern University*, http://www.basic.northwestern.edu/biotools/oligocalc.html, Dec. 4, 2014, 5 Pages.
Hoser, "Oligo Calc: Oligonucleotide Properties Calculator", *Northwestern University*, http://www.basic.northwestern.edu/biotools/oligocalc.html, Dec. 4, 2014, 10 Pages.
Hoser, "Primer-BLAST", *NCBI*, http://www.ncbi.nlm.nih.gov/tools/primer-blast/primertool.cgi?ctg_time=1417731967&job_key=4PsNu7exHpUhpyWpRIcX11-qJcZMtTjD, Dec. 4, 2014, 76 Pages.
Oroskar, A. et al., "Detection of immobilized amplicons by ELISA-like techniques", *Clin. Chem.*, vol. 42, No. 9, 1996, 1547-1555.
PCT/US2013/031589, International Preliminary Report on Patentability and Written Opinion mailed Mar. 5, 2015, 7 Pages.
PCT/US2013/059093, International Preliminary Report on Patentability and Written Opinion mailed Mar. 26, 2015, 7 Pages.
Piepenburg, "Oligo Calc: Oligonucleotide Properties Calculator", *Northwestern University*, http://www.basic.northwestern.edu/biotools/oligocalc.html, Dec. 6, 2014, 20 Pages.
Piepenburg, "Primer-BLAST", *NCBI*, http://www.ncbi.nlm.nih.gov/tools/primer-blast/primertool.cgi?ctg_time=1417877793&job_key=0Ms93mzUxfD-SPpGm2jlOIBF-imTWucs, Dec. 4, 2014, 2 Pages.
Promega, "BioMath—Tm Calculations for Oligos", https://www.promega.com/techserv/tools/biomath/calc11.htm, Dec. 4, 2014, 5 pages.
Schroth, "Oligo Calc: Oligonucleotide Properties Calculator", *Northwestern University*, http://www.basic.northwestern.edu/biotools/oligocalc.html, Dec. 4, 2014, 5 Pages.
Schroth, "Primer-BLAST", *NCBI*, http://www.ncbi.nlm.nih.gov/tools/primer-blast/primertool.cgi?ctg_time=1417745143&job_key=WkG3eUFz6Fz6FfT79fhts_In63i146-_cqL, Dec. 4, 2014, 1 page.
Sigma-Aldrich, "Oligos Melting Temperature", http://www.sigmaaldrich.com/life-science/custom-oligos/custom-dna/learning-center/oligos-melting-temp.html, Dec. 4, 2014, 2 pages.
Von Ahsen, N. et al., "Oligonucleotide Melthing Temperatures under PCR Conditions: Nearest-Neighbor Corrections for Mg2+, Deoxynucleotide Triphosphate, and Dimethyl Sulfoxide Concentrations with Comparison to Alternative Empirical Formulas", *Clinical Chemistry*, vol. 47 (11), 2001, 1956-1961.
Westin, Lorelei et al., "Anchored multiplex amplification on a microelectronic chip array", *Nature Biotechnology*, vol. 18, Feb. 2000, 119-204.
Mercier, J et al., "Solid Phase DNA Amplification: A Brownian Dynamics Study of Crowding Effects", *Biophysical Journal*, vol. 89, Jul. 2005, 32-42.
PCT/US2014/026735, International Preliminary Report on Patentability, Sep. 15, 2015, 9 pages.

\* cited by examiner

| | FAM | VIC | | FAM | VIC | | FAM | VIC | | FAM | VIC |
|---|---|---|---|---|---|---|---|---|---|---|---|
| A1 | 50 | 31.96548 | C1 | | 50 | E1 | | 50 | G1 | | 50 |
| A2 | 50 | 39.86279 | C2 | | 50 | E2 | | 50 | G2 | 30.95665 | 38.49394 |
| A3 | 44.3971 | 50 | C3 | | 50 | E3 | | 50 | G3 | 42.10394 | 36.18042 |
| A4 | 50 | 50 | C4 | | 50 | E4 | 45.15652 | 50 | G4 | | 50 |
| A5 | 50 | 50 | C5 | | 50 | E5 | 50 | 39.25991 | G5 | 43.07935 | 50 |
| A6 | 50 | 50 | C6 | | 50 | E6 | 50 | 50 | G6 | 40.46702 | 50 |
| A7 | 50 | 50 | C7 | | 50 | E7 | 50 | 27.78382 | G7 | | 50 |
| A8 | 50 | 50 | C8 | | 50 | E8 | 50 | 50 | G8 | 50 | 31.60849 |
| A9 | 50 | 50 | C9 | 38.08558 | 50 | E9 | 50 | 50 | G9 | 50 | 50 |
| A10 | 50 | 50 | C10 | 44.47919 | 50 | E10 | 50 | 50 | G10 | 50 | 50 |
| A11 | 50 | 50 | C11 | | 50 | E11 | 50 | 50 | G11 | 50 | 50 |
| A12 | 50 | 50 | C12 | | 50 | E12 | 50 | 50 | G12 | 50 | 31.61124 |
| B1 | 50 | 39.01974 | D1 | 32.6227 | 50 | F1 | 41.63503 | 39.91924 | H1 | 50 | 50 |
| B2 | 50 | 50 | D2 | 32.34154 | 38.27389 | F2 | | 50 | H2 | 50 | 50 |
| B3 | 50 | 50 | D3 | | 37.80156 | F3 | 50 | 50 | H3 | 30.91996 | 38.31835 |
| B4 | 50 | 50 | D4 | | 50 | F4 | 50 | 50 | H4 | | 50 |
| B5 | 50 | 35.26348 | D5 | 42.20201 | 50 | F5 | 50 | 50 | H5 | 50 | 37.56089 |
| B6 | 42.93367 | 40.18534 | D6 | | 50 | F6 | 50 | 39.90506 | H6 | 50 | 50 |
| B7 | 50 | 50 | D7 | | 50 | F7 | 36.69026 | 50 | H7 | 50 | 50 |
| B8 | 50 | 30.90235 | D8 | 46.95021 | 50 | F8 | 36.95259 | 39.65005 | H8 | 50 | 50 |
| B9 | 50 | 50 | D9 | | 50 | F9 | 50 | 30.54854 | H9 | 50 | 50 |
| B10 | 50 | 50 | D10 | | 50 | F10 | 50 | 50 | H10 | 50 | 29.22241 |
| B11 | 50 | 50 | D11 | 34.98179 | 50 | F11 | 50 | 50 | H11 | 50 | 50 |
| B12 | 50 | 50 | D12 | | 50 | F12 | 50 | 50 | H12 | 50 | 50 |

FIG. 6

Uncut strand will not be amplified in the 2nd TW with Pg primer

SEQUENCE LISTING

```
<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```
aaaaaaaaaa aaaaaaaaaa aaaaaaaaaa                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttttttttt tttttttttt tttttttttt                                          30

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttttttttt tttttttttt                                                     20

<210> SEQ ID NO 4
<211> LENGTH: 330
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: misc_feature
<222> LOCATION: (2)..(11)
<223> OTHER INFORMATION: This region may encompass 2, 3, 4, 5, 6, or 10
      nucleotides
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: misc_feature
<222> LOCATION: (13)..(22)
<223> OTHER INFORMATION: This region may encompass 2, 3, 4, 5, 6, or 10
      nucleotides
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: misc_feature
<222> LOCATION: (24)..(33)
<223> OTHER INFORMATION: This region may encompass 2, 3, 4, 5, 6, or 10
      nucleotides
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: misc_feature
<222> LOCATION: (35)..(44)
<223> OTHER INFORMATION: This region may encompass 2, 3, 4, 5, 6, or 10
      nucleotides
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: misc_feature

```
<222> LOCATION: (46)..(55)
<223> OTHER INFORMATION: This region may encompass 2, 3, 4, 5, 6, or 10
      nucleotides
<220> FEATURE:
<221> NAME/KEY: modified_base
<222> LOCATION: (56)..(56)
<223> OTHER INFORMATION: a, c, t, g, unknown or other
<220> FEATURE:
<221> NAME/KEY: misc_feature
<222> LOCATION: (57)..(66)
<223> OTHER INFORMATION: This region may encompass 2, 3, 4, 5, 6, or 10
      nucleotides
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: misc_feature
<222> LOCATION: (68)..(77)
<223> OTHER INFORMATION: This region may encompass 2, 3, 4, 5, 6, or 10
      nucleotides
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: misc_feature
<222> LOCATION: (79)..(88)
<223> OTHER INFORMATION: This region may encompass 2, 3, 4, 5, 6, or 10
      nucleotides
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: misc_feature
<222> LOCATION: (90)..(99)
<223> OTHER INFORMATION: This region may encompass 2, 3, 4, 5, 6, or 10
      nucleotides
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: misc_feature
<222> LOCATION: (101)..(110)
<223> OTHER INFORMATION: This region may encompass 2, 3, 4, 5, 6, or 10
      nucleotides
<220> FEATURE:
<221> NAME/KEY: modified_base
<222> LOCATION: (111)..(111)
<223> OTHER INFORMATION: a, c, t, g, unknown or other
<220> FEATURE:
<221> NAME/KEY: misc_feature
<222> LOCATION: (112)..(121)
<223> OTHER INFORMATION: This region may encompass 2, 3, 4, 5, 6, or 10
      nucleotides
<220> FEATURE:
<221> NAME/KEY: modified_base
<222> LOCATION: (122)..(122)
<223> OTHER INFORMATION: a, c, t, g, unknown or other
<220> FEATURE:
<221> NAME/KEY: misc_feature
<222> LOCATION: (123)..(132)
<223> OTHER INFORMATION: This region may encompass 2, 3, 4, 5, 6, or 10
      nucleotides
<220> FEATURE:
<221> NAME/KEY: modified_base
<222> LOCATION: (133)..(133)
<223> OTHER INFORMATION: a, c, t, g, unknown or other
<220> FEATURE:
<221> NAME/KEY: misc_feature
<222> LOCATION: (134)..(143)
<223> OTHER INFORMATION: This region may encompass 2, 3, 4, 5, 6, or 10
      nucleotides
<220> FEATURE:
<221> NAME/KEY: modified_base
<222> LOCATION: (144)..(144)
<223> OTHER INFORMATION: a, c, t, g, unknown or other
```

-continued

```
<220> FEATURE:
<221> NAME/KEY: misc_feature
<222> LOCATION: (145)..(154)
<223> OTHER INFORMATION: This region may encompass 2, 3, 4, 5, 6, or 10
      nucleotides
<220> FEATURE:
<221> NAME/KEY: modified_base
<222> LOCATION: (155)..(155)
<223> OTHER INFORMATION: a, c, t, g, unknown or other
<220> FEATURE:
<221> NAME/KEY: misc_feature
<222> LOCATION: (156)..(165)
<223> OTHER INFORMATION: This region may encompass 2, 3, 4, 5, 6, or 10
      nucleotides
<220> FEATURE:
<221> NAME/KEY: modified_base
<222> LOCATION: (166)..(166)
<223> OTHER INFORMATION: a, c, t, g, unknown or other
<220> FEATURE:
<221> NAME/KEY: misc_feature
<222> LOCATION: (167)..(176)
<223> OTHER INFORMATION: This region may encompass 2, 3, 4, 5, 6, or 10
      nucleotides
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: misc_feature
<222> LOCATION: (178)..(187)
<223> OTHER INFORMATION: This region may encompass 2, 3, 4, 5, 6, or 10
      nucleotides
<220> FEATURE:
<221> NAME/KEY: modified_base
<222> LOCATION: (188)..(188)
<223> OTHER INFORMATION: a, c, t, g, unknown or other
<220> FEATURE:
<221> NAME/KEY: misc_feature
<222> LOCATION: (189)..(198)
<223> OTHER INFORMATION: This region may encompass 2, 3, 4, 5, 6, or 10
      nucleotides
<220> FEATURE:
<221> NAME/KEY: modified_base
<222> LOCATION: (199)..(199)
<223> OTHER INFORMATION: a, c, t, g, unknown or other
<220> FEATURE:
<221> NAME/KEY: misc_feature
<222> LOCATION: (200)..(209)
<223> OTHER INFORMATION: This region may encompass 2, 3, 4, 5, 6, or 10
      nucleotides
<220> FEATURE:
<221> NAME/KEY: modified_base
<222> LOCATION: (210)..(210)
<223> OTHER INFORMATION: a, c, t, g, unknown or other
<220> FEATURE:
<221> NAME/KEY: misc_feature
<222> LOCATION: (211)..(220)
<223> OTHER INFORMATION: This region may encompass 2, 3, 4, 5, 6, or 10
      nucleotides
<220> FEATURE:
<221> NAME/KEY: modified_base
<222> LOCATION: (221)..(221)
<223> OTHER INFORMATION: a, c, t, g, unknown or other
<220> FEATURE:
<221> NAME/KEY: misc_feature
<222> LOCATION: (222)..(231)
<223> OTHER INFORMATION: This region may encompass 2, 3, 4, 5, 6, or 10
      nucleotides
<220> FEATURE:
<221> NAME/KEY: modified_base
<222> LOCATION: (232)..(232)
<223> OTHER INFORMATION: a, c, t, g, unknown or other
<220> FEATURE:
<221> NAME/KEY: misc_feature
<222> LOCATION: (233)..(242)
<223> OTHER INFORMATION: This region may encompass 2, 3, 4, 5, 6, or 10
      nucleotides
<220> FEATURE:
<221> NAME/KEY: modified_base
```

```
<222> LOCATION: (243)..(243)
<223> OTHER INFORMATION: a, c, t, g, unknown or other
<220> FEATURE:
<221> NAME/KEY: misc_feature
<222> LOCATION: (244)..(253)
<223> OTHER INFORMATION: This region may encompass 2, 3, 4, 5, 6, or 10
      nucleotides
<220> FEATURE:
<221> NAME/KEY: modified_base
<222> LOCATION: (254)..(254)
<223> OTHER INFORMATION: a, c, t, g, unknown or other
<220> FEATURE:
<221> NAME/KEY: misc_feature
<222> LOCATION: (255)..(264)
<223> OTHER INFORMATION: This region may encompass 2, 3, 4, 5, 6, or 10
      nucleotides
<220> FEATURE:
<221> NAME/KEY: modified_base
<222> LOCATION: (265)..(265)
<223> OTHER INFORMATION: a, c, t, g, unknown or other
<220> FEATURE:
<221> NAME/KEY: misc_feature
<222> LOCATION: (266)..(275)
<223> OTHER INFORMATION: This region may encompass 2, 3, 4, 5, 6, or 10
      nucleotides
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: misc_feature
<222> LOCATION: (277)..(286)
<223> OTHER INFORMATION: This region may encompass 2, 3, 4, 5, 6, or 10
      nucleotides
<220> FEATURE:
<221> NAME/KEY: modified_base
<222> LOCATION: (287)..(287)
<223> OTHER INFORMATION: a, c, t, g, unknown or other
<220> FEATURE:
<221> NAME/KEY: misc_feature
<222> LOCATION: (288)..(297)
<223> OTHER INFORMATION: This region may encompass 2, 3, 4, 5, 6, or 10
      nucleotides
<220> FEATURE:
<221> NAME/KEY: modified_base
<222> LOCATION: (298)..(298)
<223> OTHER INFORMATION: a, c, t, g, unknown or other
<220> FEATURE:
<221> NAME/KEY: misc_feature
<222> LOCATION: (299)..(308)
<223> OTHER INFORMATION: This region may encompass 2, 3, 4, 5, 6, or 10
      nucleotides
<220> FEATURE:
<221> NAME/KEY: modified_base
<222> LOCATION: (309)..(309)
<223> OTHER INFORMATION: a, c, t, g, unknown or other
<220> FEATURE:
<221> NAME/KEY: misc_feature
<222> LOCATION: (310)..(319)
<223> OTHER INFORMATION: This region may encompass 2, 3, 4, 5, 6, or 10
      nucleotides
<220> FEATURE:
<221> NAME/KEY: modified_base
<222> LOCATION: (320)..(320)
<223> OTHER INFORMATION: a, c, t, g, unknown or other
<220> FEATURE:
<221> NAME/KEY: misc_feature
<222> LOCATION: (321)..(330)
<223> OTHER INFORMATION: This region may encompass 2, 3, 4, 5, 6, or 10
      nucleotides
<220> FEATURE:
<221> NAME/KEY: misc_feature
<222> LOCATION: (1)..(330)
<223> OTHER INFORMATION: This sequence may encompass 2 to 30 'naa,'
      'naaa,' 'naaaa,' 'naaaaa,' 'naaaaaa,' or 'naaaaaaaaa' repeating
      units

<400> SEQUENCE: 4
```

-continued

```
naaaaaaaaa anaaaaaaaa aanaaaaaaa aaanaaaaaa aaaanaaaaa aaaaanaaaa        60
aaaaaanaaa aaaaaaanaa aaaaaaaana aaaaaaaaan aaaaaaaaaa naaaaaaaaa       120
anaaaaaaaa aanaaaaaaa aaanaaaaaa aaaanaaaaa aaaaanaaaa aaaaaanaaa       180
aaaaaaanaa aaaaaaaana aaaaaaaaan aaaaaaaaaa naaaaaaaaa anaaaaaaaa       240
aanaaaaaaa aaanaaaaaa aaaanaaaaa aaaaanaaaa aaaaaanaaa aaaaaaanaa       300
aaaaaaaana aaaaaaaaan aaaaaaaaaa                                        330
```

<210> SEQ ID NO 5
<211> LENGTH: 90
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(90)
<223> OTHER INFORMATION: This sequence may encompass 2 to 30 'caa'
      repeating units

<400> SEQUENCE: 5

```
caacaacaac aacaacaaca acaacaacaa caacaacaac aacaacaaca acaacaacaa        60
caacaacaac aacaacaaca acaacaacaa                                         90
```

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(60)
<223> OTHER INFORMATION: This sequence may encompass 2 to 30 'ca'
      repeating units

<400> SEQUENCE: 6

```
cacacacaca cacacacaca cacacacaca cacacacaca cacacacaca cacacacaca        60
```

<210> SEQ ID NO 7
<211> LENGTH: 120
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(120)
<223> OTHER INFORMATION: This sequence may encompass 2 to 30 'caaa'
      repeating units

<400> SEQUENCE: 7

```
caaacaaaca aacaaacaaa caaacaaaca aacaaacaaa caaacaaaca aacaaacaaa        60
caaacaaaca aacaaacaaa caaacaaaca aacaaacaaa caaacaaaca aacaaacaaa       120
```

<210> SEQ ID NO 8
<211> LENGTH: 90
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<221> NAME/KEY: misc_feature
<222> LOCATION: (1)..(90)
<223> OTHER INFORMATION: This sequence may encompass 2 to 30 'gaa'
      repeating units

<400> SEQUENCE: 8
gaagaagaag aagaagaaga agaagaagaa gaagaagaag aagaagaaga agaagaagaa        60
gaagaagaag aagaagaaga agaagaagaa                                        90

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt tttttttttt tttttttttt ttttt                                  35

<210> SEQ ID NO 10
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
tttttttttt tttttttttt ccactacgcc tccgctttcc tctctatggg cagtcggtga        60
ttcgtggaag acgggggcag tctataccccc tgtggcgacc actgcgcggt ggtttgctag      120
gagagaatga ggaacccggg gcag                                             144

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgccccggg ttcctcattc t                                                 21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtcggtgat tcgtggaaga c                                                 21

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcattctct cctagcaaac cac                                               23
```

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cccctgtggc gaccac                                                      16

<210> SEQ ID NO 15
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tttttttttt tttttttttt ccactacgcc tccgctttcc tctctatggg cagtcggtga      60
tgaaacagtt gatcatggac aaccatattc tgctgtacgg ccaaggcgga tgtacggtac     120
agcagatact aagatgatga agagaatgag gaacccgggg cag                       163

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaacagttg atcatggaca accat                                            25

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcatcttagt atctgctgta ccgtacat                                         28

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ccgccttggc cgtacag                                                     17

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 19
aaaaaaaaaa aaaaaaaaaa aaaaaaaaaa aaaaa                                   35

<210> SEQ ID NO 20
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
aaaaaaaaaa aaaaaaaaaa ccactacgcc tccgctttcc tctctatggg cagtcggtga        60
ttcgtggaag acggggcag tctataccc tgtggcgacc actgcgcggt ggtttgctag        120
gagagaatga ggaacccggg gcag                                              144

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaaaaaaaa aaaaaaaaaa                                                    20

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tttttttttt tttttttttt tttttttttt tt                                      32
```

METHODS, COMPOSITIONS, SYSTEMS, APPARATUSES AND KITS FOR NUCLEIC ACID AMPLIFICATION

This application claims the benefit of priority under 35 U.S.C. §119 to U.S. Provisional application No. 61/692,830, filed Aug. 24, 2012, and is (1) a continuation-in-part of U.S. application Ser. No. 13/328,844, filed Dec. 16, 2011, which claims priority to U.S. Provisional Application Nos. 61/424,599, filed Dec. 17, 2010; 61/445,324, filed Feb. 22, 2011; 61/451,919, filed Mar. 11, 2011; 61/526,478, filed Aug. 23, 2011; and 61/552,660, filed Oct. 28, 2011; and is also (2) a continuation-in-part of International PCT Application No. PCT/US2011/65535, filed Dec. 16, 2011, which claims priority to U.S. Provisional Application Nos. 61/424,599, filed Dec. 17, 2010; 61/445,324, filed Feb. 22, 2011; 61/451,919, filed Mar. 11, 2011; 61/526,478, filed Aug. 23, 2011; and 61/552,660, filed Oct. 28, 2011; the disclosures of all of which aforementioned applications are incorporated herein by reference in their entireties.

Throughout this application various publications, patents, and/or patent applications are referenced. The disclosures of these publications, patents, and/or patent applications in their entireties are hereby incorporated by reference into this application in order to more fully describe the state of the art to which this invention pertains.

BACKGROUND

Nucleic acid amplification is very useful in molecular biology and has wide applicability in practically every aspect of biology, therapeutics, diagnostics, forensics and research. Generally, multiple amplicons are generated from a starting template using one or more primers, where the amplicons are homologous or complementary to the template from which they were generated. Multiplexed amplification can also streamline processes and reduce overheads. A single set of primers can be mixed with different templates, or a single template can be contacted with multiple different primers, or multiple different templates can be contacted with multiple different primers. This application relates to methods and reagents for nucleic acid amplification and/or analysis.

SUMMARY

Methods, reagents and products of nucleic acid amplification and/or analysis are provided herein. Amplification can make use of immobilized and/or soluble primers. Amplicons generated from methods provided herein are suitable substrates for further analysis, e.g., sequence determination.

BRIEF DESCRIPTION OF THE DRAWINGS

FIG. 6: Table of the Ct values of the 96 duplex TaqMan qPCR reactions.

FIG. 8: Schematic depiction of an exemplary strand-flipping and walking strategy. (A) Template walking, (B) Strand flipping to generate flipped strands, (C) addition of new primer-binding sequence Pg' on final flipped strands.

DEFINITIONS

Figure 1:
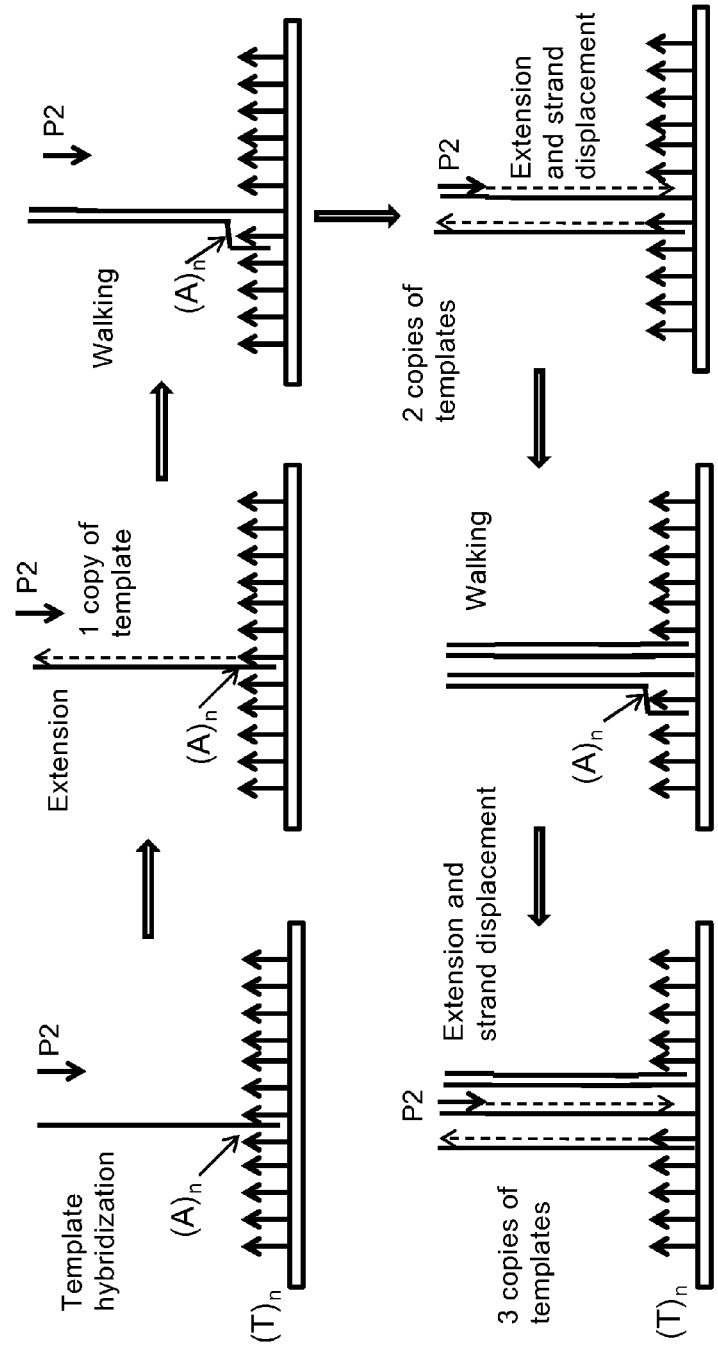
FIG. 1: Schematic showing an embodiment of template walking. In an alternative embodiment, the immobilized primer comprises an adenosine-rich sequence designated as $(A)_n$, e.g., $(A)_{30}$, (SEQ ID NO:1) and the primer binding site for the immobilized primer on the template comprises a complementary T-rich sequence, e.g., $(T)_{30}$ (SEQ ID NO:2)
Figure 2:
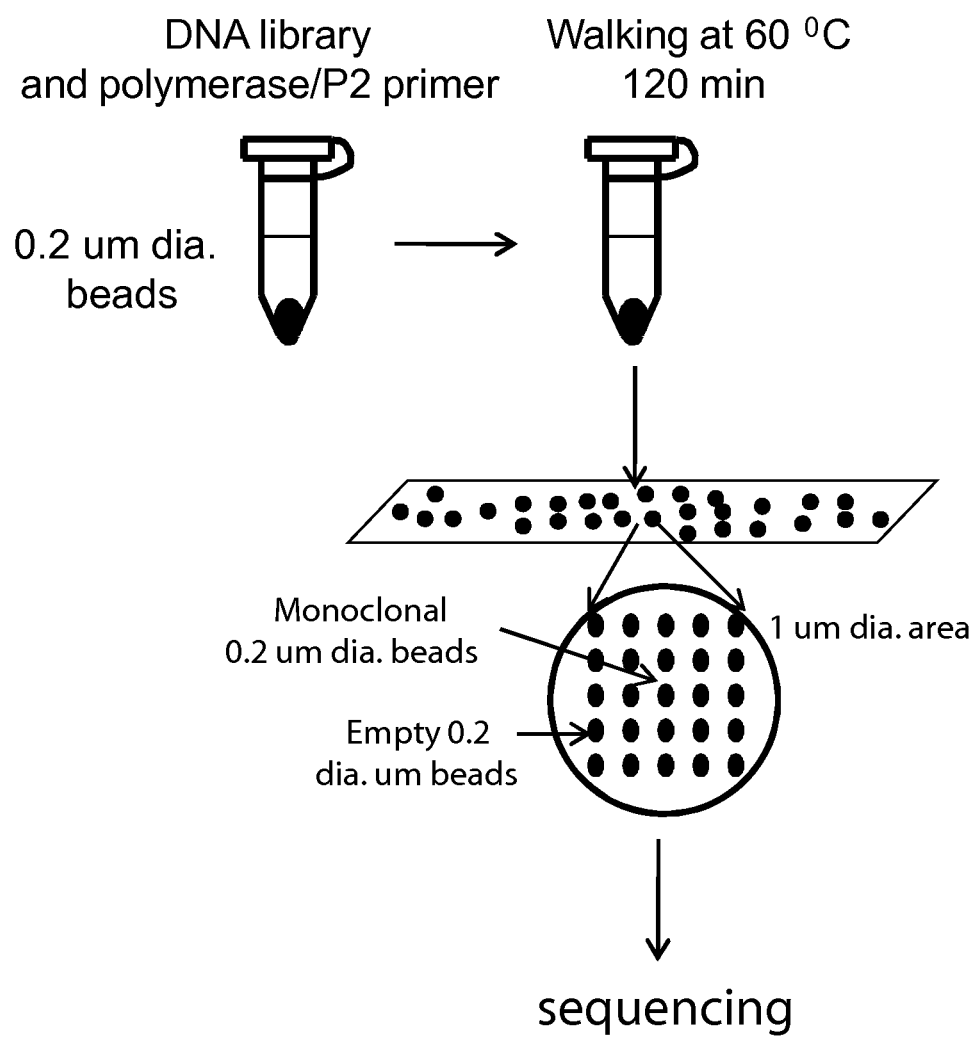
FIG. 2: Overview of amplification on beads by template walking and deposition of beads onto a planar array for sequencing

Any active verb (or its gerund) is intended to indicate that the corresponding action occurs at a specific, significant or substantial level (e.g., more than random, or more than an appropriate control). For example the act of "hybridizing" indicates that a significant or substantial level of specific hybridization takes place. For example in the case of hybridization of a primer to a template during an amplification process, hybridizing is optionally sufficient to achieve a desired fold of amplification—e.g., at least $10^3$ or $10^4$ or $10^5$ or $10^6$ amplicons from a single template. In another example, specific hybridization is more than would happen between two nucleic acids that share no significant amount of sequence homology. In yet another example, specific hybridization comprises binding of a nucleic acid to a target nucleotide sequence in the absence of substantial binding to other nucleotide sequences present in the hybridization mixture under defined stringency conditions. Optionally, the sample is derived from tissues or fluids taken from living or dead organisms (e.g., humans) for the purposes of diagnostics or forensics). Optionally, the same comprises a genomic library or an exome library.

Two sequences can be considered to be complementary if one sequence hybridizes substantially and specifically under the conditions of choice to the other sequence. Two sequences can be considered to be homologous if the reverse complement of one sequence can hybridize substantially and specifically under the conditions of choice to the other sequence.

Substantial hybridization for example is where more than 5%, optionally 10%, 30%, 50% or 80% of one of the nucleic acids is hybridized to the other nucleic acid. Hybridization between two single-stranded nucleic acids often but not necessarily involves the formation of a double stranded structure that is stable under conditions of choice. The conditions of choice are for example conditions in which hybridization is intended, e.g., during an annealing step of an amplification cycle. Two single-stranded polynucleotides are optionally considered to be hybridized if they are bonded to each other by two or more sequentially adjacent base pairings. Optionally, a substantial proportion of nucleotides in one strand of the double stranded structure undergo Watson-Crick base-pairing with a nucleoside on the other strand. Hybridization also includes the pairing of nucleoside analogs, such as deoxyinosine, nucleosides with 2-aminopurine bases, and the like, that may be employed to reduce the degeneracy of the probes, whether or not such pairing involves formation of hydrogen bonds.

A nucleic acid can be considered immobilized if it is attached to a support in a manner that is substantially stable, at least during conditions of choice (e.g., during the amplification reaction). The attachment can be by any mechanism, including but not limited to non-covalent bonding, ionic interactions, or covalent linkage. If a first nucleic acid is hybridized to a second nucleic acid immobilized on a support, then the first nucleic acid can also be considered to be immobilized to the support during amplification, if amplification conditions are such that substantial amounts of the first and second nucleic acids are associated or connected with each other at any or all times during amplification. For example the first and second nucleic acids can be associated together by hybridization involving Watson-Crick base pairing or hydrogen bonding. In an example, the amplification conditions of choice allow at least 50%, 80%, 90%, 95% or 99% of the first nucleic acid to remain hybridized with the second nucleic acid, or vice versa. A nucleic acid can be considered unimmobilized or non-immobilized if it is not directly or indirectly attached to or associated with a support.

A medium can be considered flowable under conditions of choice if the medium is under those conditions at least temporarily a fluid medium that does not substantially or completely restrain or impede transfer or movement of an unimmobilized molecule. The unimmobilized molecule is not itself immobilized to a solid support or surface or associated with another immobilized molecule. In an embodiment, the unimmobilized molecule is a solute (e.g., a nucleic acid) through the flowable medium. Exemplary transfer or movement in the medium can be by means of diffusion, convection, turbulence, agitation, Brownian motion, advection, current flows, or other molecular movements within the liquid) from any first point in the continuous phase to any other point in fluid communication or in the same continuous phase. For example, in a flowable medium a significant amount of an unimmobilized nucleic acid is transferred from one immobilization site to another immobilization site that is within the same continuous phase of the flowable medium, or in fluid communication with the first immobilization site. Optionally, the rate of transfer or movement of the nucleic acid in the medium is comparable to the rate of transfer or movement of the nucleic acid in water. In some instances, the conditions of choice are conditions that the medium is subjected to during amplification. The conditions of choice may or may not allow the flowable medium to remain substantially motionless. The conditions may or may not subject the flowable medium to active mixing, agitation or shaking. The medium is optionally flowable at least temporarily during amplification. For example the medium is flowable under at least one preamplification and/or amplification condition of choice. Optionally, a flowable medium does not substantially prevent intermingling of different unimmobilized nucleic acids or transfer of an unimmobilized nucleic acid between different zones of a continuous phase of the flowable medium. The movement or transfer of nucleic acids for example can be caused by means of diffusion or convection. A medium is optionally considered nonflowable if unimmobilized nucleic acids upon amplification fail to spread or move between different immobilization sites or over the entire continuous phase. Generally, a flowable medium does not substantially confine unimmobilized nucleic acids (e.g., the templates or amplicons) within limited zones of the reaction volume or at fixed locations during the period of amplification. Optionally, a flowable medium can be rendered non-flowable by various means or by varying its conditions. Optionally, a medium is flowable if it is liquid or is not semisolid. A medium can be considered flowable if its fluidity is comparable to pure water. In other embodiments, a medium can be considered flowable if it a fluid that is substantially free of polymers, or if its viscosity coefficient is similar to that of pure water.

In an embodiment, a support comprises one or more immobilization sites. A nucleic acid (e.g., a template or an amplicon) optionally associates with the support at its corresponding immobilization site. An immobilization site optionally comprises a specific portion or area of a support, or a position or location on a support. An immobilization site can have or optionally can lack any specific or predetermined location, position, dimension, size, area or structure on the support, or any other distinguishing parameter or characteristic. Optionally, one or more of such parameters are determined for an immobilization site at the time of association of the template with the support, and/or during or at the completion of amplification. In an embodiment, one or template-attachment moieties (e.g., amplification primers) are attached to the support, which optionally are or are not arranged on the support at pre-determined or defined positions or angles or distances from the center of a defined point. Optionally, an arrangement of template molecules over one or more immobilization sites on a support is or is not achieved through an intentional design or placement of individual attachment moieties. Such a "randomly-patterned" or "random" array of attachment moieties (e.g., primers) can be achieved by dropping, spraying, plating or spreading a solution, emulsion, aerosol, vapor or dry preparation comprising a pool of nucleic acid molecules onto a support and allowing the nucleic acid molecules to settle onto the support, with or without any intervention that would direct them to specific or predetermined immobilization sites thereon.

A support or immobilization site optionally comprises one or more oligonucleotides (e.g., amplification primers) attached to a support. Preferably but not necessarily, the attachment of the oligonucleotide to the support or immobilization site is stable during subsequent amplification or other assays (e.g., more than 10%, 30%, 50%, 70% or 90% of oligonucleotides remain attached after being subjected to the amplification conditions of choice).

Optionally, in any method described herein, all primers on at least one support or immobilization site comprise the same sequence. The support or immobilization site can optionally comprise other nucleic acids which do not hybridize to one strand of the template of interest or its complement. The support or immobilization site optionally does not comprise any other nucleic acid which hybridizes to one strand of the template of interest or its complement (i.e., the immobilization site optionally lacks any other primers). Optionally, a support or immobilization site comprises a plurality of primers having at least two different sequences. Optionally, the support or immobilization site comprises a species of immobilized primers that is complementary to a first portion of a single-stranded template, and does not comprise an immobilized primer that is homologous to a second non-overlapping portion of the template (or can hybridize to the template-complement). The two portions are non-overlapping if they do not contain any subportions that hybridize to each other or to a complement of the other portion.

Two or more different types of primer (e.g., different in sequence) can be present in substantially the same concentrations as one another, or alternatively in different concentrations. Optionally, the primers are substantially homogeneously dispersed over the support or immobilization site. Optionally, in any method described herein, two different immobilization sites are spatially separated subcomponents (e.g., portions or areas) of a single support and/or are on different (e.g., structurally disconnected) supports. Optionally, in any method described herein, at least one immobilization site includes the entire surface of the support or the entire volume of a support. The immobilized primers are optionally uniformly distributed over the one or more supports or immobilization sites.

Optionally, in any method described herein, the two different immobilization sites are located in a predetermined arrangement in or on a shared support (e.g. in a grid pattern). In other embodiments, the metes, bounds or positioning of one or more immobilization sites is not known or predetermined before immobilization of the template to the support. In an example, the support comprises multiple immobilized primers, and the primer to which a starting template hybridizes (e.g., before any amplification occurs) can be considered to be included within (e.g., a central point of) the immobilization site for that template. In such an embodiment, the positioning of an immobilization site is determined during or after hybridization of the primer to the template. The metes and bounds of an immobilization site can also be determined during or after extension and/or amplification.

A population of nucleic acids is considered clonal if a substantial portion of its members have substantially identical (or substantially complementary) sequence. It will be understood that members of a population need not be 100% identical or complementary, e.g., a certain number of "errors" may occur during the course of synthesis. In an embodiment, at least 50% of the members of a population are substantially identical (or complementary) to each other or to a reference nucleic acid molecule (i.e., a molecule of defined sequence used as a basis for a sequence comparison). More preferably at least 60%, at least 70%, at least 80%, at least 90%, at least 95%, at least 99%, or more of the members of a population are substantially identical (or complementary) to the reference nucleic acid molecule. Two molecules can be considered substantially identical if the percent identity between the two molecules is at least 75%, 80%, 85%, 90%, 95%, 98%, 99%, 99.9% or greater, when optimally aligned. Two molecules can be considered substantially complementary if the percent complementarity between the two molecules is at least 75%, 80%, 85%, 90%, 95%, 98%, 99%, 99.9% or greater, when optimally aligned. In addition, a low or insubstantial level of mixing of non-homologous nucleic acids may occur during methods described herein, and thus a clonal population may contain a minority of diverse nucleic acids (e.g., less than 30%, e.g., less than 10%).

As will be appreciated by one of ordinary skill in the art, references to templates, initializing oligonucleotides, extension probes, primers, etc., can refer to populations or pools of nucleic acid molecules that are substantially identical within a relevant portion, rather than single molecules. For example, a "template" can refer to a plurality of substantially identical template molecules; a "probe" can refer to a plurality of substantially identical probe molecules, etc. In the case of probes that are degenerate at one or more positions, it will be appreciated that the sequence of the probe molecules that comprise a particular probe will differ at the degenerate positions, i.e., the sequences of the probe molecules that constitute a particular probe may be substantially identical only at the nondegenerate position(s). These terms within this application are intended to provide support for either a population or a molecule. Where it is intended to refer to a single nucleic acid molecule (i.e., one molecule), the terms "template molecule", "probe molecule", "primer molecule", etc., may be used instead. In certain instances the plural nature of a population of substantially identical nucleic acid molecules will be explicitly indicated.

"Template", "oligonucleotide", "probe", "primer", "template", "nucleic acid" and the like are intended to be interchangeable terms herein. These terms refer to polynucleotides, not necessarily limited to any length or function. The same nucleic acid can be regarded as a "template", "probe" or "primer" depending on the context, and can switch between these roles with time. A "polynucleotide," also called a "nucleic acid," is a linear polymer of two or more nucleotides joined by covalent internucleosidic linkages, or variant or functional fragments thereof. In naturally occurring examples of these, the internucleoside linkage is typically a phosphodiester bond. However, other examples optionally comprise other internucleoside linkages, such as phosphorothiolate linkages and may or may not comprise a phosphate group. Polynucleotides include double- and single-stranded DNA, as well as double- and single-stranded RNA, DNA: RNA hybrids, peptide-nucleic acids (PNAs) and hybrids between PNAs and DNA or RNA, and also include known types of modifications. Polynucleotides can optionally be attached to one or more non-nucleotide moieties such as labels and other small molecules, large molecules such proteins, lipids, sugars, and solid or semi-solid supports, for example through either the 5' or 3' end. Labels include any moiety that is detectable using a detection method of choice, and thus renders the attached nucleotide or polynucleotide similarly detectable using a detection method of choice. Optionally, the label emits electromagnetic radiation that is optically detectable or visible. In some cases, the nucleotide or polynucleotide is not attached to a label, and the presence of the nucleotide or polynucleotide is directly detected. A "nucleotide" refers to a nucleotide, nucleoside or analog thereof. Optionally, the nucleotide is an N- or C-glycoside of a purine or pyrimidine base. (e.g., deoxyribonucleoside containing 2-deoxy-D-ribose or ribonucleoside containing D-ribose). Examples of other analogs include, without limitation, phosphorothioates, phosphoramidates, methyl phosphonates, chiral-methyl phosphonates, and 2-O-methyl ribonucleotides. Referring to a nucleic acid by any one of these terms should not be taken as implying that the nucleic acid has any particular activity, function or properties. For example, the word "template" does not indicate that the "template" is being copied by a polymerase or that the template is not capable of acting as a "primer" or a "probe".

It will be appreciated that in certain instances nucleic acid reagents involved in amplification such as a template, probe, primer, etc., may be a portion of a larger nucleic acid molecule that also contains another portion that does not serve the same function. Optionally, this other portion does not serve any template, probe, or primer function. In some instances, a nucleic acid that substantially hybridizes to an optionally-immobilized primer (e.g., on an immobilization site) is considered to be the "template". Any one or more nucleic acid reagents that are involved in template walking (template, immobilized strands, immobilized or unimmobilized primer, etc.) may be generated before or during amplification from other nucleic acids. The nucleic acid reagent is optionally generated from (and need not be identical to) an input nucleic acid by making one or more modifications to the nucleic acid that was initially introduced into the template walking medium. An input nucleic acid can for example be subjected to restriction digestion, ligation, one or more amplification cycles, denaturation, mutation, etc, to generate a nucleic acid that serves as the template, primer, etc, during amplification or further amplification. For example, a double-stranded input nucleic acid can be denatured to generate a first single-stranded nucleic acid which optionally is used to generate a second complementary strand. If so desired, the first single-stranded nucleic acid can be considered the "template" for our purposes herein. Alternatively, the second complementary strand generated from the first single-stranded nucleic acid can be considered the "template" for our purposes herein. In another example, a template is derived from an input nucleic acid and is not necessarily identical to the input nucleic acid. For example, the template can comprise additional sequence not present an input nucleic acid. In an embodiment the template can be an amplicon generated from an input nucleic acid using one or more primers with a 5' overhang that is not complementary to the input nucleic acid.

The term "amplifying" refers to production of copies of a nucleic acid molecule, for example via repeated rounds of primed enzymatic synthesis. Optionally, such amplifying takes place with an immobilized template nucleic acid molecule and/or one or more primers that are immobilized. An amplicon is for example a single-stranded or double-stranded nucleic acid that is generated by an amplification procedure from a starting template nucleic acid. The amplicon comprises a nucleic acid strand, of which at least a portion is substantially identical or substantially complementary to at least a portion of the starting template. Where the starting template is double-stranded, an amplicon comprises a nucleic acid strand that is substantially identical to at least a portion of one strand and is substantially complementary to at least a portion of either strand. The amplicon can be single-stranded or double-stranded irrespective of whether the initial template is single-stranded or double-stranded.

The term "support" includes any solid or semisolid article on which reagents such as nucleic acids can be immobilized. Nucleic acids may be immobilized on the solid support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube. A support includes any solid phase material upon which a oligomer is synthesized, attached, ligated or otherwise immobilized. A support can optionally comprise a "resin", "phase", "surface" and "support". A support may be composed of organic polymers such as polystyrene, polyethylene, polypropylene, polyfluoroethylene, polyethyleneoxy, and polyacrylamide, as well as copolymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to comprise one or more wells, depressions or other containers, vessels, features or locations. A plurality of supports may be configured in an array at various locations. A support is optionally addressable (e.g., for robotic delivery of reagents), or by detection means including scanning by laser illumination and confocal or deflective light gathering. An amplification support (e.g., a bead) can be placed within or on another support (e.g., within a well of a second support).

In an embodiment the solid support is a "microparticle," "bead" "microbead", etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymehtymethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments of the invention a population of microparticles having different shapes sizes and/or colors can be used. The microparticles can optionally be encoded, e.g., with quantum dots such that each microparticle can be individually or uniquely identified.

DETAILED DESCRIPTION

In some embodiments, the disclosure relates generally to methods, compositions, systems, apparatuses and kits for clonally amplifying one or more nucleic acid templates to form clonally amplified populations of nucleic acid templates. Any amplification method described herein optionally comprises repeated cycles of nucleic acid amplification. A cycle of amplification optionally comprises (a) hybridization of primer to a template strand, (b) primer extension to form a first extended strand, (c) partial or incomplete denaturation of the extended strand from the template strand. The primer that hybridizes to the template strand (designated "forward" primer for convenience) is optionally immobilized on or to a support. The support is for example solid or semi-solid. Optionally, the denatured portion of the template strand from step (c) is free to hybridize with a different forward primer in the next amplification cycle. In an embodiment, primer extension in a subsequent amplification cycle involves displacement of the first extended strand from the template strand. A second "reverse" primer can for example be included which hybridizes to the 3' end of the first extended strand. The reverse primer is optionally not immobilized.

In an embodiment, the templates are amplified using primers immobilized on/to one or more solid or semi-solid supports. Optionally the support comprises immobilized primers that are complementary to a first portion of a template strand. Optionally, the support does not significantly comprise an immobilized primer that is homologous to a second non-overlapping portion of the same template strand. The two portions are non-overlapping if they do not contain any subportions that hybridize to each other or to a complement thereof. In another example, the support optionally does not significantly comprise an immobilized primer that can hybridize to the complement of the template strand).

Optionally, a plurality of nucleic acid templates are amplified simultaneously in a single continuous liquid phase in the presence of one or more supports, where each support comprises one or more immobilization sites. In an embodiment, each template is amplified to generate a clonal population of amplicons, where individual clonal populations are immobilized within or on a different support or immobilization site from other amplified populations. Optionally, the amplified populations remain substantially clonal after amplification.

A template is for example amplified to generate clonal populations which comprise template-homologous strands (called "template strands" or "reverse strands" herein) and/or template-complementary strands (called "primer strands" or "forward strands" herein). In an embodiment clonality is maintained in the resulting amplified nucleic acid populations by maintaining association between template strands and its primer strands, thereby effectively associating or "tethering" associated clonal progeny together and reducing the probability of cross-contamination between different clonal populations. Optionally, one or more amplified nucleic acids in the clonal population is attached to a support. A clonal population of substantially identical nucleic acids can optionally have a spatially localized or discrete macroscopic appearance. In an embodiment a clonal population can resemble a distinct spot or colony (e.g., when distributed in a support, optionally on the outer surface of the support).

In some embodiments, the disclosure relates generally to novel methods of generating a localized clonal population of clonal amplicons, optionally immobilized in/to/on one or more supports. The support can for example be solid or semisolid (such as a gel or hydrogel). The amplified clonal population is optionally attached to the support's external surface or can also be within the internal surfaces of a support (e.g., where the support has a porous or matrix structure).

In some embodiments, amplification is achieved by multiple cycles of primer extension along a template strand of interest (also called a "reverse" strand). For convenience, a primer that hybridizes to the template strand of interest is termed a "forward" primer, and is optionally extended in template-dependent fashion to form a "forward" strand that is complementary to the template strand of interest. In some methods, the forward strand is itself hybridized by a second primer termed the "reverse" primer, which is extended to form a new template strand (also called a reverse strand). Optionally, at least a portion of the new template strand is homologous to the original template ("reverse") strand of interest.

As mentioned, one or more primers can be immobilized in/on/to one or more supports. Optionally, one primer is immobilized by attachment to a support. A second primer can be present and is optionally not immobilized or attached to a support. Different templates can for example be amplified onto different supports or immobilization sites simultaneously in a single continuous liquid phase to form clonal nucleic acid populations. A liquid phase can be considered continuous if any portion of the liquid phase is in fluid contact or communication with any other portion of the liquid body. In another example, a liquid phase can be considered continuous if no portion is entirely subdivided or compartmentalized or otherwise entirely physically separated from the rest of the liquid body. Optionally, the liquid phase is flowable. Optionally, the continuous liquid phase is not within a gel or matrix. In other embodiments, the continuous liquid phase is within a gel or matrix. For example the continuous liquid phase occupies pores, spaces or other interstices of a solid or semisolid support.

Where the liquid phase is within a gel or matrix, one or more primers are optionally immobilized on a support. Optionally the support is the gel or matrix itself. Alternatively the support is not the gel or matrix itself. In an example one primer is immobilized on a solid support contained within a gel and is not immobilized to gel molecules. The support is for example in the form of a planar surface or one or more microparticles. Optionally the planar surface or plurality of microparticles comprises forward primers having substantially identical sequence. In an embodiment, the support does not contain significant amounts of a second different primer. Optionally, a second non-immobilized primer is in solution within the gel. The second non-immobilized primer for example binds to a template strand (i.e., reverse strand), whereas the immobilized primer binds to a forward strand.

For convenience, the portion of a nucleic acid template strand that is hybridized by a primer will be referred to as the "primer-binding sequence" or PBS. Thus, a forward primer binds to a forward-primer binding sequence ("forward PBS") on a reverse strand, while a reverse primer binds to a reverse PBS on the forward strand.

An embodiment includes a method of primer extension, comprising: (a) a primer-hybridization step, (b) an extension step, and (c) a walking step. Optionally, the primer-hybridization step comprises hybridizing a first primer molecule ("first forward primer") to a complementary forward-primer-binding sequence ("forward PBS") on a nucleic acid strand ("reverse strand"). Optionally the extension step comprises generating an extended first forward strand that is a full-length complement of the reverse strand and is hybridized thereto. The extended first forward strand is for example generated by extending the first forward primer molecule in template-dependent fashion using the reverse strand as template. Optionally the walking step comprises hybridizing a second primer ("second forward primer") to the forward PBS where the reverse strand is also hybridized to the first forward strand. For example, the walking step comprises denaturing at least a portion of the forward PBS from the forward strand ("free portion"), where another portion of the reverse strand remains hybridized to the forward strand.

In an embodiment, the primer extension method is an amplification method, in which any one or more steps of primer-hybridization, extension and/or walking are repeated at least once. For example, the method can comprise amplifying the forward strand by one or more amplification cycles. An amplification cycle optionally comprises extension and walking. An exemplary amplification cycle comprises or consists essentially of extension followed by walking. Optionally, the second forward primer of a first amplification cycle acts as the first forward primer of a subsequent amplification cycle. For example, the second forward primer of a walking step in a first amplification cycle acts as the first forward primer of an extension step of a subsequent amplification cycle.

Optionally, the method of primer extension or amplification further comprises extending or amplifying the reverse strand by (a) hybridizing a first reverse primer molecule to a complementary reverse-primer-binding sequence ("reverse PBS") on an extended forward strand; (b) generating an extended first reverse strand that is a full-length complement of the forward strand and hybridized thereto, by extending the first reverse primer molecule in template-dependent fashion using the forward strand as template; and (c) hybridizing a second primer ("second reverse primer") to the reverse PBS where the forward strand is also hybridized to the first reverse strand. One or more repetitions of steps (b)-(c) are optionally performed, wherein the second reverse primer of step (c) is the first reverse primer of repeated step (b); and wherein a substantial proportion of forward strands are hybridized to reverse strands at all times during or between said one or more repetitions. In embodiments, the substantial proportion is optionally at least 30%, 40%, 50%, 60%, 65%, 70%, 75%, 80%, 85%, 90%, 95% or 99%.

Optionally, during amplification the reverse strand and/or forward strand is not exposed to totally-denaturing conditions that would result in complete separation of a significant fraction (e.g., more than 10%, 20%, 30%, 40% or 50%) of a large plurality of strands from their extended and/or full-length complements.

In an embodiment a substantial proportion of forward and/or reverse strands are optionally hybridized to extended and/or full-length complements at all times during or between one or more amplification cycles (e.g., 1, 5, 10, 20, or all amplification cycles performed). In embodiments, the substantial proportion of strands is optionally at least 60%, 65%, 70%, 75%, 80%, 85%, 90%, 95% or 99% of strands. In an embodiment this is achieved by maintaining the amplification reaction at a temperature higher than the $T_m$ of unextended primers, but lower than the $T_m$ of the primer-complementary strands. For example, amplification conditions are kept within a temperature that is higher than the $T_m$ of unextended forward primers, but lower than the $T_m$ of extended or full-length reverse strands. Also for example, amplification conditions are kept within a temperature that is higher than the $T_m$ of unextended reverse primers, but lower than the $T_m$ of extended or full-length forward strands.

Optionally, one or more forward primers, and/or one or more reverse primers are breathable, e.g., have a low $T_m$. In an example at least 60%, 65%, 70%, 75%, 80%, 85%, 90%, 95% or 99% of nucleotide bases of a breathable primer are adenine, thymine or uracil or are complementary to adenine, thymine or uracil.

The $T_m$ of a nucleic acid strand (e.g., a primer or template strand) is for example the temperature at which at least a desired fraction of a clonal population of duplexes are rendered completely single-stranded under the chosen reagent conditions, where an individual duplex comprises the nucleic acid strand in question hybridized to its full-length complement. By default, the desired fraction is 50%. In embodiments, the desired fraction is optionally at least 10%, 20%, 30%, 40%, 50%, 60%, 65%, 70%, 75%, 80%, 85%, 90%, 95% or 99%. In an embodiment the $T_m(N)$ is theoretically predicted using known methods, e.g., as discussed herein.

In another embodiment the $T_m$ is empirically measured by known methods. (e.g., Spink, Methods Cell Biol. 2008; 84:115-41; Meunier-Prest et al., Nucleic Acids Res. 2003 Dec. 1; 31(23): e150; Brewood et al., Nucleic Acids Res. 2008 September; 36(15): e98.)

The $T_m$ for a desired fraction can be depicted as $T_m(N)$ where N denotes the desired fraction in percentage terms. In an embodiment the $T_m(50)$ of the forward and/or reverse primer (at which 50% of all primer molecules are completely dissociated from their complementary PBSs) is not more than 50° C., 55° C., 60° C., 65° C., 70° C., 75° C. or 80° C. Optionally, the $T_m(50)$ of the extended or full-length forward and/or reverse strands (at which 50% of all strand molecules are completely dissociated from their complementary sequences) is not less than 80° C., 75° C., 70° C., 65° C., 60° C. or 55° C. In another embodiment the $T_m(80)$ of the forward and/or reverse primer is not more than 50° C., 55° C., 60° C., 65° C., 70° C., 75° C. or 80° C. Optionally, the $T_m(80)$ of the extended or full-length forward and/or reverse strands is not less than 80° C., 75° C., 70° C., 65° C., 60° C. or 55° C. In another embodiment the $T_m(90)$ of the forward and/or reverse primer is not more than 50° C., 55° C., 60° C., 65° C., 70° C., 75° C. or 80° C. Optionally, the $T_m(90)$ of the extended or full-length forward and/or reverse strands is not less than 80° C., 75° C., 70° C., 65° C., 60° C. or 55° C. In another embodiment the $T_m(95)$ of the forward and/or reverse primer is not more than 50° C., 55° C., 60° C., 65° C., 70° C., 75° C. or 80° C. Optionally, the $T_m(95)$ of the extended or full-length forward and/or reverse strands is not less than 80° C., 75° C., 70° C., 65° C., 60° C. or 55° C. Optionally, the $T_m(99)$ of the extended or full-length forward and/or reverse strands is not less than 80° C., 75° C., 70° C., 65° C., 60° C. or 55° C. In another embodiment the $T_m(95)$ of the forward and/or reverse primer is not more than 50° C., 55° C., 60° C., 65° C., 70° C., 75° C. or 80° C. Optionally, the $T_m(99)$ of the extended or full-length forward and/or reverse strands is not less than 80° C., 75° C., 70° C., 65° C., 60° C. or 55° C.

Optionally, one or more amplification cycles (e.g., 1, 5, 10, 20, or substantially all amplification cycles) are performed at temperature that is higher than the $T_m(70)$ of an unextended primer and lower than the $T_m(20)$ of the complementary full-length strand. For example, the temperature is higher than the $T_m(80)$ of an unextended primer and lower than the $T_m(20)$ or $T_m(15)$ or $T_m(10)$ or $T_m(5)$ or $T_m(1)$ of the complementary full-length strand. Also for example the temperature is higher than the $T_m(90)$ of an unextended primer and lower than the $T_m(20)$ or $T_m(15)$ or $T_m(10)$ or $T_m(5)$ or $T_m(1)$ of the complementary full-length strand. Also for example the temperature is higher than the $T_m(95)$ of an unextended primer and lower than the $T_m(20)$ or $T_m(15)$ or $T_m(10)$ or $T_m(5)$ or $T_m(1)$ of the complementary full-length strand. Also for example the temperature is higher than the $T_m(98)$ of an unextended primer and lower than the $T_m(20)$ or $T_m(15)$ or $T_m(10)$ or $T_m(5)$ or $T_m(1)$ of the complementary full-length strand. Also for example the temperature is higher than the $T_m(99)$ of an unextended primer and lower than the $T_m(20)$ or $T_m(15)$ or $T_m(10)$ or $T_m(5)$ or $T_m(1)$ of the complementary full-length strand. Optionally, the one or more amplification cycles are performed at temperature that is at least 5, 10, 15, 20, 25, 30, 35, or 45° C. higher than the $T_m(50)$ of an unextended primer. Optionally, the temperature is at least 5, 10, 15, 20, 25, 30, 35, or 45° C. lower than the $T_m(50)$ of a full-length primer-complementary strand. In an embodiment the unextended primer is a forward primer and the complementary full-length strand is a reverse strand, or vice versa.

Optionally, template-dependent extension of a forward primer using a reverse strand as template in the extension step results in displacement of another forward strand that was already hybridized to the reverse strand. Optionally, template-dependent extension of a reverse primer using a forward strand as template in the extension step results in displacement of another reverse strand that was already hybridized to the forward strand.

In an embodiment the method further comprises completely separating the extended forward strands from reverse strands after performing primer extension or a desired number of amplification cycles, and optionally removing separated forward strands from the presence of separated immobilized reverse strands, or vice versa.

Optionally, one or more nucleic acid reagents are not in contact with a recombinase and/or reverse transcriptase and/or helicase and/or nicking enzyme and/or any other enzyme that is not a polymerase during any one or more steps. For example the primers and/or template are not in contact with one or more such enzymes at any time.

Denaturation is optionally achieved non-enzymatically, e.g., by raising the temperature. In an embodiment amplification is performed under substantially isothermal conditions, as described herein.

Optionally, any one or more nucleic acids, e.g., primers are attached (e.g., covalently attached) to a support. In an embodiment the first and/or second forward primers are immobilized to a single (same) support.

In an embodiment, first and second forward primers are closely immobilized to the same support, whereby amplification generates an immobilized clonal population of extended forward strands. Optionally, the distance between the first and second forward primers is not more than twice the length of the primer or the PBS.

Optionally, a plurality of template nucleic acids are individually hybridized to spatially-separated immobilization sites, whereby amplification generates spatially-separated clonal populations corresponding to individual template nucleic acids.

In an embodiment, first forward primer is hybridized to a forward PBS on a "reverse" template strand. Optionally, the first forward primer is immobilized on a support. The first forward primer can be extended along the reverse strand to form (an extended) first forward strand. The extension is optionally template-dependent, using the reverse strand as a template. After extension, the first forward strand and the reverse strand are optionally hybridized to each other in a duplex. Optionally, at least part of the PBS of the first reverse strand and the forward-primer portion of the first forward strand are separated from one another (e.g., via denaturation or melting), but the first reverse strand and the first forward strand remain associated with (e.g., hybridized to) each other over another portion. The separated portion of the reverse strand including at least part of the forward-PBS can then be annealed (e.g., by hybridization) to a second, different forward primer. Optionally, the second forward primer is immobilized on a support. The second forward primer can for example be immobilized on the same support as the first forward primer, and is optionally situated sufficiently close to the first primer so that the a portion of the reverse strand can hybridize to the first forward strand while another portion of the reverse strand is hybridized to the second forward primer simultaneously. The second forward primer can then be extended in turn to form an extended second forward strand. Optionally, the second forward primer is extended along the reverse strand in a template-dependent fashion. Extension of the second forward primer optionally displaces the first forward strand from the reverse strand. As before, the primer binding sequence of the reverse strand can be separated from the primer portion of the second forward strand, where another portion of the reverse strand remains associated (e.g., by hybridization) with the second forward strand. These steps can be repeated to with further forward primers to form further extended forward strands (for example, extended third, fourth, fifth, sixth, seventh, eighth, ninth, tenth or higher order extended strands). The process can optionally be repeated for a desired number of amplification cycles to provide a population of amplified, immobilized nucleic acid molecules. The population can be substantially clonal in nature. For example, the amplified nucleic acid molecules of the amplified clonal population can include a plurality of nucleic acids that are substantially identical and/or substantially complementary to each other.

Optionally, the extended forward strands comprise a reverse-primer-binding sequence ("reverse PBS"), to which a reverse primer hybridizes. The reverse PBS on the forward strand optionally comprises or is near the 3' end of the forward strands. In some embodiments, amplification involves dissociating least part of the reverse PBS from any hybridized or associated sequence, such as sequence on a reverse strand. The reverse PBS on the forward strand is optionally contacted with a reverse primer which hybridizes to it. The reverse primer is then extended using the forward strand as template to form an extended reverse strand. Optionally, the newly-generated reverse strand acts as template for forward primer extension. The reverse strand can also participate as template, primer, or probe in another reaction, including any method described herein.

The amplified nucleic acid populations can be used for many different purposes, including sequencing, screening, diagnosis, in situ nucleic acid synthesis, monitoring gene expression, nucleic acid fingerprinting, etc.

Optionally, any one or more primer extension and/or amplification methods herein generate one or more immobilized nucleic-acid extension products. In a variation, a solid support comprises primers that all identical or substantially identical. The solid support can comprise other nucleic acids. Optionally, these other nucleic acids do not hybridize to a template strand of interest or its complement. The solid support optionally does not comprise any other nucleic acid which hybridizes to the template strand of interest or its complement.

In some embodiments, the disclosure relates generally to methods, compositions, systems, apparatuses and kits for clonally amplifying a nucleic acid template onto a support in an amplification reaction solution. Optionally, the nucleic acid template is contacted with a support in a solution comprising a continuous liquid phase. The support can include a population of primers, including at least a first primer and a second primer. The population of primers can be immobilized on the support, for example by covalent attachment to the support. In some embodiments, the nucleic acid template includes a primer binding sequence adjacent to a target sequence. The primer binding sequence can by complementary to a sequence of the first primer and optionally a sequence of the second primer. The target sequence can be noncomplementary to the primers in the population. In some embodiments, the primer binding sequence of the nucleic acid template is hybridized to the first primer. The first primer can be extended along the template using a polymerase, thereby forming an extended first primer. At least a portion of the primer binding sequence of the template can be separated (e.g., denatured or melted) from the extended first primer. The separating is optionally performed while maintaining hybridization between a portion of the template and the extended first primer. The separated portion of the primer binding sequence can be subsequently hybridized to the second primer. Optionally, such hybridization is performed while maintaining hybridization between the other portion of the template and the extended first primer. The second primer can be extended along the template using a polymerase, thereby forming a support including an extended first primer and an extended second primer. The extended portion of the extended first primer and/or the extended second primer can include sequence complementary to the target sequence.

In some embodiments, the disclosure relates generally to methods for clonally amplifying a nucleic acid template onto a support in an amplification reaction solution, comprising: contacting a nucleic acid template with a support in a liquid solution, wherein the support includes a population of immobilized primers including at least a first primer and a second primer, and wherein the nucleic acid template includes a primer binding sequence adjacent to a target sequence, where the primer binding sequence is complementary to a sequence of the first primer and a sequence of the second primer, and the target sequence is noncomplementary to the primers in the population; hybridizing the primer binding sequence of the nucleic acid template to the first primer; extending the first primer along the template using a polymerase, thereby forming an extended first primer; denaturing at least a portion of the primer binding sequence of the template from the extended first primer while maintaining hybridization between another portion of the template and the extended first primer; hybridizing the denatured portion of the primer binding sequence to the second primer while maintaining hybridization between the other portion of the template and the extended first primer; and extending the second primer along the template using a polymerase, thereby forming a support including an extended first primer and an extended second primer, where the extended first primer and the extended second primer each include sequence complementary to the target sequence. The population of primers can be comprised of substantially identical primers that differ in sequence by no more than one, two, three, four or five nucleotides. In some embodiments, the primer population is comprised of different primers, at least some of which include a sequence that is complementary to the primer binding sequence of the template. In some embodiments, the primers of population are noncomplementary to the sequence of the 5' terminal half of the template. In some embodiments, the primers of the population are noncomplementary to the sequence of the 3' terminal half of any of the extended primers of the support. In some embodiments, the primers of the population are noncomplementary to any sequence of the template other than the primer binding sequence.

In some embodiments, the disclosure relates generally to methods for clonally amplifying a population of nucleic acid templates onto a population of supports in an amplification reaction solution, comprising: clonally amplifying a first template onto a first nucleic acid template onto a first support according to any of the methods disclosed herein, and clonally amplifying a second nucleic acid template onto a second support according to the same method, wherein both supports are included within a single continuous liquid phase during the amplifying.

As will be appreciated by one of ordinary skill in the art, references to templates, initializing oligonucleotides, extension probes, primers, etc., can in some embodiments refer to populations or pools of nucleic acid molecules that are substantially identical within a relevant region rather than single molecules. Thus, for example, a "template" can in some embodiments refer to a plurality of substantially identical templates; a "probe" can in some embodiments refer to a plurality of substantially identical probe molecules, etc. In the case of probes that are degenerate at one or more positions, it will be appreciated that the sequence of the probe molecules that comprise a particular probe will differ at the degenerate positions, i.e., the sequences of the probe molecules that constitute a particular probe may be substantially identical only at the nondegenerate position(s). For purposes of description the singular form can be used to refer not only to single molecules but also to populations of substantially identical molecules. In certain instances the singular nature of a nucleic acid molecule, or the plural nature of a population of substantially identical nucleic acid molecules, will be explicitly indicated.

It will be understood that members of a population need not be 100% identical. For example, all members of a clonally amplified population of nucleic acid sequence need not be identical since a certain number of "errors" may occur during the course of synthesis; similarly, not all primers within a population of primers may be identical to each other. In some embodiments, at least 50% of the members of a population are identical to a reference nucleic acid molecule (i.e., a molecule of defined sequence used as a basis for a sequence comparison). In some embodiments, at least 50% of the members of a population are at least 70%, 75%, 85%, 90%, or more preferably at least 95% identical to a reference nucleic acid molecule. More preferably at least 60%, at least 70%, at least 80%, at least 90%, at least 95%, at least 99%, or more of the members of a population are at least 85%, 90%, or more preferably at least 95% identical, or yet more preferably at least 99% identical to the reference nucleic acid molecule. Preferably the percent identity of at least 95% or more preferably at least 99% of the members of the population to a reference nucleic acid molecule is at least 98%, 99%, 99.9% or greater. Percent identity may be computed by comparing two optimally aligned sequences, determining the number of positions at which the identical nucleic acid base (e.g., A, T, C, G, U, or I) occurs in both sequences to yield the number of matched positions, dividing the number of matched positions by the total number of positions, and multiplying the result by 100 to yield the percentage of sequence identity. It will be appreciated that in certain instances a nucleic acid molecule such as a template, probe, primer, etc., may be a portion of a larger nucleic acid molecule that also contains a portion that does not serve a template, probe, or primer function. In that case individual members of a population need not be substantially identical with respect to that portion.

A nucleic acid optionally comprises one or more nucleotides. In an embodiment a nucleotide comprises any one or more of a nucleobase (nitrogenous base), a five-carbon sugar (either ribose or 2'-deoxyribose), and a phosphate group. Optionally, a nucleotide comprises all three components or derivatives thereof. Optionally, the nucleobases is a purine or a pyrimidine base. Exemplary purine bases include adenine and guanine, while exemplary pyrimidines are thymine, uracil and cytosine As used herein, the term "complementary" and its variants, when used in reference to individual nucleotides, include nucleotides that are efficiently incorporated by DNA polymerases opposite each other during DNA replication under physiological conditions. In an typical embodiment, complementary nucleotides can form base pairs with each other, such as the A-T/U and G-C base pairs formed through specific Watson-Crick type hydrogen bonding between the nucleobases of nucleotides and/or polynucleotides positions antiparallel to each other; other types of base pairing can also occur. For example, the complementarity of other artificial base pairs can be based on other types of hydrogen bonding and/or hydrophobicity of bases and/or shape complementarity between bases.

As used herein, the term "complementary" and its variants, when used in reference to nucleic acid sequences, refers to nucleic acid sequences that can undergo cumulative base pairing with each other at two or more individual corresponding positions in antiparallel orientation, as in a hybridized duplex. Optionally there can be "complete" or "total" complementarity between a first and second nucleic acid sequence where each nucleotide in the first nucleic acid molecule or sequence can undergo a stabilizing base pairing interaction with a nucleotide in the corresponding antiparallel position on the second nucleic acid sequence; alternatively, two nucleic acid sequences can be complementary when at least 50% of the nucleotide residues of one nucleic acid sequence are complementary to nucleotide residues in the other nucleic acid sequence. The complementary residues within a particular complementary nucleic acid sequence need not always be contiguous with each other, and can be interrupted by one or more noncomplementary residues within the complementary nucleic acid sequence. In some embodiments, at least 50%, but less than 100%, of the residues of one of the two complementary nucleic acid sequences are complementary to residues in the other nucleic acid sequence. In some embodiments, at least 70%, 80%, 90%, 95% or 99% of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence.

As used herein, "complementary" when used in reference to two or more nucleic acid molecules, can include any nucleic acid molecules where each molecule comprises a sequence that is complementary to a sequence in the other nucleic acid molecules. The complementary nucleic acid molecules need not be complementary across their entire length, and each molecule can include one or more regions that is noncomplementary to the other molecules. For example, a template and a primer molecule can be referred to as "complementary" even when they are of different lengths; in some embodiments, the template can be longer than the primer and include sequence that is noncomplementary to any sequence of the primer, or vice versa.

The term "noncomplementary" and its variants, as used herein with reference to two nucleic acid molecules or sequences, typically refers to nucleic acid molecules or sequences in which less than 50% of the residues of one nucleic acid molecule or sequence are complementary to residues in the other nucleic acid molecule or sequence. A "mismatch" is present at any position in the nucleic acid molecule molecules or sequences where the two opposed nucleotides are not complementary. Similarly, two nucleotide sequences or portions thereof are considered to match each other if the sequences or portions are identical or complementary to each other.

As used herein, the term "hybridization" refers to the process of base pairing between any two nucleic acid molecules including complementary nucleotides at one or more positions. Typically, such base pairing can occur according to established paradigms, for example the Watson-Crick paradigm wherein A-T/U and G-C base pairs are formed through specific Watson-Crick type hydrogen bonding between the nucleobases of nucleotides and/or polynucleotides positions antiparallel to each other. In some embodiments, hybridization can occur according to non-Watson Crick paradigms as well; for example, artificial base pairs can be formed through other types of hydrogen bonding and/or hydrophobicity of bases and/or shape complementarity between bases. The hybridized nucleic acid molecules need not be hybridized across their entire length, and each molecule can include one or more regions not hybridized to the other molecule. For example, a template and a primer molecule can be described as hybridized to each other even when a substantial region of the template, primer or both remain non-hybridized to each other. Furthermore, a region of hybridization can include one or more contiguous nucleotides that are not base paired with each other. Nucleic acid molecules (or sequences within nucleic acid molecules) that are base paired with each other in this manner are referred to as "hybridized". In some embodiments, a single nucleic acid molecule may undergo self-hybridization (e.g., hairpin formation) with itself.

Typically, hybridizing nucleic acid molecules (for example, hybridizing a primer with a template) includes contacting nucleic acid molecules with each other under conditions where one or more nucleotide residues within each nucleic acid molecule base pairs with one or more nucleotides of another nucleic acid molecule. The contacting can be performed using any suitable conditions, depending on the desired application. In one exemplary assay, two nucleic acid molecules are contacted in a buffered solution comprising salts and/or detergents, e.g., SDS, for a desired length of time and for a desired period. For example, the hybridization can be performed using low stringency, medium stringency or high stringency hybridization conditions. The stringency of hybridization can be adjusted by varying various hybridization parameters, including for example temperature, salt concentration, SDS concentration, at the like. Methods of hybridization and of controlling the stringency of hybridization are well known in the field.

Among other things, a method is provided of generating a localized clonal population of immobilized clonal amplicons of a single-stranded template sequence, comprising: (a) attaching the single-stranded template sequence ("template 1") to an immobilization site ("IS1"), wherein IS1 comprises multiple copies of an immobilized primer ("IS1 primer") which can hybridize substantially to template 1, and template 1 is attached to IS1 by hybridization to an IS1 primer, and (b) amplifying template 1 using IS1 primer and a non-immobilized primer ("SP1 primer") in solution, wherein amplified strands that are complementary to the single-stranded template 1 cannot hybridize substantially when single-stranded to primers on IS1, wherein amplification generates a localized clonal population of immobilized clonal amplicons around the point of initial hybridization of template 1 to IS1.

Also provided is a method of generating separated and immobilized clonal populations of a first template sequence ("template 1") and a second template sequence ("template 2"), comprising amplifying the first and second template sequence to generate a population of clonal amplicons of template 1 substantially attached to first immobilization site ("IS1") and not to a second immobilization site ("IS2"), or a population of clonal amplicons of template 2 substantially attached to IS2 and not to IS1, wherein: (a) both templates and all amplicons are contained within the same continuous liquid phase, where the continuous liquid phase is in contact with a first and second immobilization site (respectively, "IS1" and "IS2"), and where IS1 and IS2 are spatially separated, (b) template 1 when in single-stranded form comprises a first subsequence ("T1-FOR") at one end, and a second subsequence ("T1-REV") at its opposite end, (c) template 2 when in single-stranded form comprises a first subsequence ("T2-FOR") at one end, and a second subsequence ("T2-REV") at its opposite end, (d) IS1 comprises multiple copies of an immobilized nucleic acid primer ("IS1 primer") that can hybridize substantially to T1-FOR and T2-FOR when T1 and T2 are single-stranded, (e) IS2 comprises multiple copies of an immobilized primer ("IS2 primer") that can hybridize substantially to both T1-FOR and T2-FOR when T1 and T2 are single-stranded, (f) the reverse complement of T1-REV when single-stranded cannot hybridize substantially to primers on IS1, but can hybridize substantially to a non-immobilized primer ("SP1") in the continuous liquid phase; and (g) the reverse complement of T2-REV when single-stranded cannot hybridize substantially to primers on IS2, but can hybridize substantially to a non-immobilized primer ("SP2") in the continuous liquid phase.

In addition, a method is provided of generating separated and immobilized clonal populations of a first template sequence ("template 1") and a second template sequence ("template 2"), comprising amplifying the first and second template sequence, wherein: (a) both templates are in single-stranded form and are both contained within the same continuous liquid phase, where a first and second immobilization site (respectively, "IS1" and "IS2") are in contact with said continuous liquid phase, and where IS1 and IS2 are spatially separated, (b) template 1 comprises a first subsequence ("T1-FOR") at its 3' end, and a second subsequence ("T1-REV") that is non-overlapping with T1-FOR and at its 5' end, (c) template 2 comprises a first subsequence ("T2-FOR") at its 3' end, and a second subsequence ("T2-REV") that is non-overlapping with T2-FOR and at its 5' end, (d) IS1 comprises an immobilized primer ("IS1 primer") that can hybridize to both T1-FOR and T2-FOR, (e) IS2 comprises an immobilized primer ("IS2 primer") that can hybridize to both T1-FOR and T2-FOR, and (f) the reverse complement of T1-REV cannot hybridize substantially to primers on IS1, and/or the reverse complement of T2-REV cannot hybridize substantially to primers on IS2, but can each hybridize substantially to a non-immobilized primer in the continuous liquid phase; whereby amplification results in a population of clonal amplicons of template 1 substantially attached to IS1 and not to IS2, and/or a population of clonal amplicons of template 2 substantially attached to IS2 and not to IS1.

Optionally, in any method described herein, the continuous medium is flowable. Optionally, intermixing of non-immobilized nucleic acid molecules is substantially unretarded in the continuous liquid phase during at least a portion of the amplification process, e.g., during any one or more steps or cycles described herein.

Optionally, in any method described herein, intermixing is substantially unretarded for a period of time during amplification. For example, intermixing is substantially unretarded during the entire duration of amplification.

Optionally, in any method described herein, any nucleic acid that has dissociated from one immobilization site is capable of substantially hybridizing to both immobilization sites and any movement (e.g., movement by diffusion, convection) of said dissociated nucleic acid to another immobilization site is not substantially retarded in the continuous liquid phase.

Optionally, in any method described herein, the continuous liquid phase is in simultaneous contact with IS1 and IS2.

Optionally, in any method described herein, a first portion of a template that is bound by an immobilized primer does not overlap with a second portion of the template whose complement is bound by a non-immobilized primer.

Optionally, in any method described herein, at least one template to be amplified is generated from an input nucleic acid after the nucleic acid is placed in contact with at least one immobilization site.

Optionally, any method described herein comprising the steps of: (a) contacting a support comprising immobilized primers with a single-stranded nucleic acid template, wherein: hybridizing a first immobilized primer to a primer-binding sequence (PBS) on the template (b) extending the hybridized first primer in template-dependent extension to form an extended strand that is complementary to the template and at least partially hybridized to the template; (c) partially denaturing the template from the extended complementary strand such that at least a portion of the PBS is in single-stranded form ("free portion"); (d) hybridizing the free portion to a non-extended, immobilized second primer (e) extending the second primer in template-dependent extension to form an extended strand that is complementary to the template (f) optionally, separating the annealed extended immobilized nucleic acid strands from one another.

Optionally, in any method described herein (a) during amplification, nucleic acid duplexes are formed comprising a starting template and/or amplified strands; which duplexes are not subjected during amplification to conditions that would cause complete denaturation of a substantial number of duplexes.

Optionally, in any method described herein, the single-stranded templates are produced by taking a plurality of input double-stranded or single-stranded nucleic acid sequences to be amplified (which sequence may be known or unknown) and appending or creating a first universal adaptor sequence and a second universal adaptor sequence onto the ends of at least one input nucleic acid; wherein said first universal adaptor sequence hybridizes to IS1 primer and/or IS2 primer, and the reverse complement of said second universal adaptor sequence hybridizes to at least one non-immobilized primer. The adaptors can be double-stranded or single-stranded.

Optionally, in any method described herein, first and second nucleic acid adaptor sequences are provided at first and second ends of said single-stranded template sequence.

Optionally, in any method described herein, a tag is also added to one or more nucleic acid sequences (e.g., a template or a primer or an amplicons), said tag enabling identification of a nucleic acid containing the tag.

Optionally, in any method described herein, all primers on at least one immobilization site or support have the same sequence. Optionally, an immobilization site or support comprises a plurality of primers having at least two different sequences. Optionally, two or more different types of primer (e.g., different in sequence) are present in substantially the same concentrations as one another, or alternatively in different concentrations. Optionally, the primers of at least one immobilization site or support are substantially homogeneously dispersed over the immobilization site or support. Optionally, in any method described herein, two different immobilization sites are spatially separated subcomponents of a single support and/or are on different unconnected supports.

Optionally, in any method described herein, the support forms a three-dimensional matrix and the two different immobilization sites are two different three-dimensional portions of the support that are not completely overlapping. Optionally, in any method described herein, the two different immobilization sites are two different areas on the surface of a support that are not completely overlapping. Optionally, in any method described herein, the two different immobilization sites are on different supports.

At least one support can be a bead, e.g., a microbead or nanobead. In an embodiment, the bead is a "scaffolded nucleic acid polymer particle" or SNAPP, described in U.S. Publ. App. No. 2010-0304982, incorporated by reference.

Optionally, in any method described herein, at least one immobilization site includes the entire surface of the support or the entire volume of the support. Optionally, in any method described herein, the two different immobilization sites are located in a predetermined arrangement (e.g. in a grid pattern). In other embodiments, one or more immobilization sites are not predetermined (e.g., the support comprises immobilized primers at non-predetermined locations), and the primer to which a starting template hybridizes (e.g., before any amplification occurs) can be considered to be the immobilization site for that template.

Optionally, in any method described herein, heating is used to partially separate annealed nucleic acid strands. Optionally, primer extension is achieved by hybridizing the primer to a template, and contacting with a polymerase and nucleotides. The contacting and hybridizing can be achieved simultaneously or sequentially. Optionally, one or more nucleotides are detectably labeled.

Optionally, in any method described herein, the method further includes the step of treating one or more extended immobilized nucleic acid strands so as to release a nucleic acid molecule or a part thereof. The treating for example can optionally consist of nucleic acid cleavage, e.g., with a restriction endonuclease or with a ribozyme. For example, one or more of said primers has a restriction endonuclease recognition site or a ribozyme recognition site or has part of such a site, which part becomes complete when primer extension occurs.

Optionally, in any method described herein, the method is used to amplify a plurality of different nucleic acid sequences, e.g., sequentially or simultaneously. The plurality is for example more than $10^3$, $10^5$, $10^7$, $10^9$, $10^{11}$, $10^{14}$, or $10^{20}$ target nucleic acids.

Any method herein can be used to provide amplified nucleic acid molecules for diagnosis or for screening or for genotyping, or to provide amplified nucleic acid molecules to be used as a support for other components, or to generate additional nucleic acid molecules in free (e.g., non-immobilized rather than immobilized) form. For example any method can be used to monitor gene expression, or to identify nucleic acid molecules with gene products that are rarely expressed, identifying heterozygous individuals, nucleic acid fingerprinting.

Optionally, in any method described herein, said different nucleic acid sequences are each provided with a first and second nucleic acid "adaptor" sequence as described anywhere herein, said first and second "adaptor" sequences being the same for the each of the different nucleic acid sequences.

Optionally, in any method described herein, said different nucleic acid sequences are each provided with a different tag so that the different sequences can be distinguished from one another.

In an embodiment, amplification is achieved using RPA, i.e., recombinase-polymerase amplification (see, e.g., WO2003072805, incorporated by reference herein). RPA optionally is carried out without substantial variations in temperature or reagent conditions. In an embodiment herein, partial denaturation and/or amplification, including any one or more steps or methods described herein, can be achieved using a recombinase and/or single-stranded binding protein. Suitable recombinases include RecA and its prokaryotic or eukaryotic homologues, or functional fragments or variants thereof, optionally in combination with single-strand binding proteins (SSBs). In an embodiment, the recombinase agent optionally coats single-stranded DNA (ssDNA) such as an amplification primer to form a nucleoprotein filament strand which invades a double-stranded region of homology on a template. This optionally creates a short hybrid and a displaced strand bubble known as a D-loop. In an embodiment, the free 3'-end of the filament strand in the D-loop is extended by DNA polymerases to synthesize a new complementary strand. The complementary strand displaces the originally-paired partner strand of the template as it elongates. In an embodiment, one or more of a pair of amplification primers are contacted with one or more recombinase agents before be contacted with a template which is optionally double-stranded.

In any method described herein, amplification of a template (target sequence) comprises contacting a recombinase agent with one or more of at least one pair of amplification primers, thereby forming one or more "forward" and/or "reverse" RPA primers. Any recombinase agent that has not associated with the one or more primers is optionally removed. Optionally, one or more forward RPA primers are then contacted with a template strand, which optionally has a region of complementarity to at least one RPA primer. The template strand can be hybridized to a Contacting of a RPA primer with a complementary template optionally results hybridization between said primer and the template. Optionally, the 3' end of the primer is extended along the template with one or more polymerases (e.g., in the presence of dNTPs) to generate a double stranded nucleic acid and a displaced template strand. The amplification reaction can comprise repeated cycles of such contacting and extending until a desired degree of amplification is achievable. Optionally the displaced strand of nucleic acid is amplified by a concurrent RPA reaction. Optionally, the displaced strand of nucleic acid is amplified by contacting it in turn with one or more complementary primers; and (b) extending the complementary primer by any strategy described herein.

In an embodiment the one or more primers comprise a "forward" primer and a "reverse" primer. Placing both primers and the template in contact optionally results in a first double stranded structure at a first portion of said first strand and a double stranded structure at a second portion of said second strand. Optionally, the 3' end of the forward and/or reverse primer is extended with one or more polymerases to generate a first and second double stranded nucleic acid and a first and second displaced strand of nucleic acid. Optionally the second displaced strand is at least partially complementary to each other and can hybridize to form a daughter double stranded nucleic acid which can serve as double stranded template nucleic acid in a subsequent amplification cycles.

Optionally said first and said second displaced strands is at least partially complementary to said first or said second primer and can hybridize to said first or said second primer.

In an alternative embodiment of any method or step or composition or array described herein, the support optionally comprises immobilized primers of more than one sequence. After a template nucleic acid strand hybridizes to first complementary immobilized primer, the first primer can then be extended and the template and the primer can be separated partially or completely from one another. The extended primer can then be annealed to a second immobilised primer that has different sequence from the first, and the second primer can be extended. Both extended primers can then be separated (e.g., fully or partially denatured from one another) and can be used in turn as templates for extension of additional immobilized primers. The process can be repeated to provide amplified, immobilised nucleic acid molecules. In an embodiment, this amplification results in immobilized primer extension products of two different sequences that are complementary to each other, where all primer extension products are immobilized at the 5' end to the support.

The amplified nucleic acids generated from any method herein can be used for many different purposes, including sequencing, screening, diagnosis, in situ nucleic acid synthesis, monitoring gene expression, nucleic acid fingerprinting, etc.

Optionally, the template concentration is adjusted such that immobilized templates are generally spaced as a sufficient distance from each other that the clonal clusters generated from individual templates have little or substantially no overlap with each other, or do not contaminate one another during or after amplification or replication. Optionally, any of the amplification methods herein involve a step of adjusting the concentration of template nucleic acid before it is contacted with a solid support so that individual template molecules hybridize to primers immobilized on the solid support at a density of at least 10000, 100000, 400000, 500000, 1,000,000 or $10^7$ molecules per mm$^2$. Optionally, individual template molecules are amplified in-situ on the support, giving rise to clonal populations that are spatially-centered around the point of hybridization of the initial template.

Strand Flipping

In a "flipping" embodiment described below, two or more primers are extended to form two or more corresponding extended strands. Optionally, the two or more primers that are extended comprise or consist essentially of substantially identical sequence, and the extended portions of corresponding extended strand are at least partly non-identical and/or complementary to each other.

One exemplary embodiment of flipping is as follows. A starting template is amplified, e.g., by template walking, to generate a plurality of primer-extended strands (which for convenience will be designated as "forward" strands). Optionally, the forward strands are complementary to the starting template. Optionally, the forward strands are immobilized on the support. Optionally, the forward strands comprise substantially identical sequence, e.g., the forward strands are substantially identical to each other. In an embodiment the forward strands are formed by extension of one or more primers immobilized on a support ("forward" primers). The forward primers and/or the forward strands are optionally attached to the support at or near their 5' ends. Optionally, one or more of the primer-extended forward strands comprises a 3' sequence (called a self-hybridizing sequence) that is absent in the unextended primer and can hybridize under the conditions of choice to a 5' sequence (this process will be termed "self-hybridization"). The 5' sequence is optionally part of the unextended forward primer. In an example, the forward extension product forms a "stem-loop" structure upon such hybridization. Optionally, the unextended forward primer comprises a "cleavable" nucleotide at or near its 3'terminus that is susceptible to cleavage. In an embodiment, the cleavable nucleotide is linked to at least one other nucleotide by a "scissile" internucleoside linkage that can be cleaved under conditions that will not substantially cleave phosphodiester bonds.

After extension, the forward-primer extension product (i.e., the forward strand) is optionally allowed to self-hybridize. In a further embodiment, after allowing for self-hybridization the forward strand is cleaved at a scissile linkage of a cleavable nucleotide (for example a nucleotide which forms a scissile linkage with a neighboring nucleotide). The cleavage results in two fragments of the primer-extension product (i.e., the extended forward strand). In an embodiment, a first fragment comprises at least a portion of the original unextended forward primer. Optionally, the first fragment does not comprise any extended sequence. Optionally, the first fragment is immobilized (e.g., because the unextended forward primer was already immobilized). In an embodiment, a second fragment comprises extended sequence. Optionally the second fragment comprises any 3' portion of the unextended primer beyond the cleavable nucleotide or does not comprise any portion of the unextended primer. Optionally, the second fragment is hybridized to the first portion through its self-hybridizing sequence.

In an example, the cleavable nucleotide is one that is removed by one or more enzymes. The enzyme can for instance be a glycosylase. The glycosylase optionally has N-glycosylase activity which releases the cleavable nucleotide from double stranded DNA. Optionally, the removal of the cleavable nucleotide generates an abasic, apurinic or apyrimidinic site. The abasic site can optionally be further modified, for example by another enzymatic activity. Optionally, the abasic site is modified by a lyase to generate a base gap.

The lyase for example cleaves 3' and/or 5' to the abasic site. Cleavage optionally occurs at both the 5' and 3' end by the lyase, resulting in removing the abasic site and leaving a base gap. Exemplary cleavable nucleotides such as 5-hydroxyuracil, 7,8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine can be recognized and removed by various glycosylases to form an apurinic site. One suitable enzyme is formamidopyrimidine [fapy]-DNA glycosylase, also known as 8-oxoguanine DNA glycosylase or FPG. FPG acts both as a N-glycosylase and an AP-lyase. The N-glycosylase activity optionally releases damaged purines from double stranded DNA, generating an apurinic (AP site), where the phosphodiester backbone is optionally intact. The AP-lyase activity cleaves both 3' and 5' to the AP site thereby removing the AP site and leaving a one-base gap. In an example the cleavable nucleotide is 8-oxoadenine, which is coverted to a one-base gap by FPG with both glycosylase and lyase activities.

In another embodiment the cleavable nucleotide is uridine. Optionally, the uridine is cleaved by "USER" reagent, which includes Uracil DNA glycosylase (UDG) and the DNA glycosylase-lyase Endonuclease VIII, where UDG catalyses the excision of a uracil base, forming an abasic (apyrimidinic) site while leaving the phosphodiester backbone intact, and where the lyase activity of Endonuclease VIII breaks the phosphodiester backbone at the 3' and 5' sides of the abasic site so that base-free deoxyribose is released; after which kinase is optionally used to convert the phosphate group on the 3' end of cleaved product to an —OH group).

At least one cleaved fragment is optionally contacted with a polymerase. Optionally the first immobilized fragment can be extended by the polymerase. If so desired the second hybridized fragment can act as template for extension of the first fragment. In an embodiment a "flipped" double-stranded extension product is formed. This flipped product can optionally be subjected to template walking in any manner described herein. When both flipped and unflipped are subjected to template walking, a cluster of two different extension products is formed, where both extension products have an identical portion (corresponding to the unextended primers) and portion complementary to each other, corresponding to the extended portions of the extension products.

In an embodiment, a sequence of interest, such as a self-hybridizing sequence or a new primer-binding site, can be optionally be added at the 3' ends of extended forward strands by contacting the extended forward strands with a single-stranded "splice" adaptor sequence in the presence of extension reagents (e.g., a polymerase and dNTPs). This splice sequence optionally comprises a 3' portion that is substantially complementary to a 3' end portion of the extended forward strand, and a 5' portion that is substantially complementary to the sequence of interest to be added. After hybridizing the splice adaptor to the 3' end of the extended forward strand, the forward strand is subjected to template-dependent polymerase extension using the splice adaptor as template. Such extension results in the addition of the sequence of interest to the 3' end of the extended forward strand.

Thus, any method of primer extension and/or amplification described herein can include any one or more of the following steps:

a) extension of immobilized forward primers by template walking to generate a plurality of extended forward strands which are optionally identical;

b) optionally hybridizing a splice adaptor to a 3' end of the extended forward strands and subjecting the forward strands to template-dependent extension using the splice adaptor as a template, thereby adding a further 3' sequence to the further-extended forward strands, wherein a portion of the added 3' sequence is complementary to a portion of the unextended forward primer and hybridizes thereto to form a stem-loop structure c) cleaving the forward strands at a scissile linkage of a cleavable nucleotide located at or near the junction of unextended forward primer sequence and extended forward strand sequence; and optionally removing the cleavable nucleotide, thereby generating two cleaved fragments, the first fragment comprising a portion of an unextended forward primer hybridized to a 3' primer-complementary sequence on the second fragment;

d) optionally subjecting the first fragment to polymerase extension using the second fragment as template to generate a flipped forward strand;

e) optionally hybridizing a second splice adaptor to a 3' end of the flipped forward strand, and subjecting the forward strands to template-dependent extension using the splice adaptor as a template, thereby adding a further 3' sequence to the flipped forward strands, wherein a portion of the added 3' sequence is a new primer-binding sequence that is absent in the flipped strands;

f) selectively extending or amplifying the flipped strands which comprise the new primer-binding sequence by contacting with the new primer and extending or amplifying by any method, e.g., as described herein. The new primer will not bind to unflipped strands or to flipped strands that were not further extended in step (e).

Figure 8A:
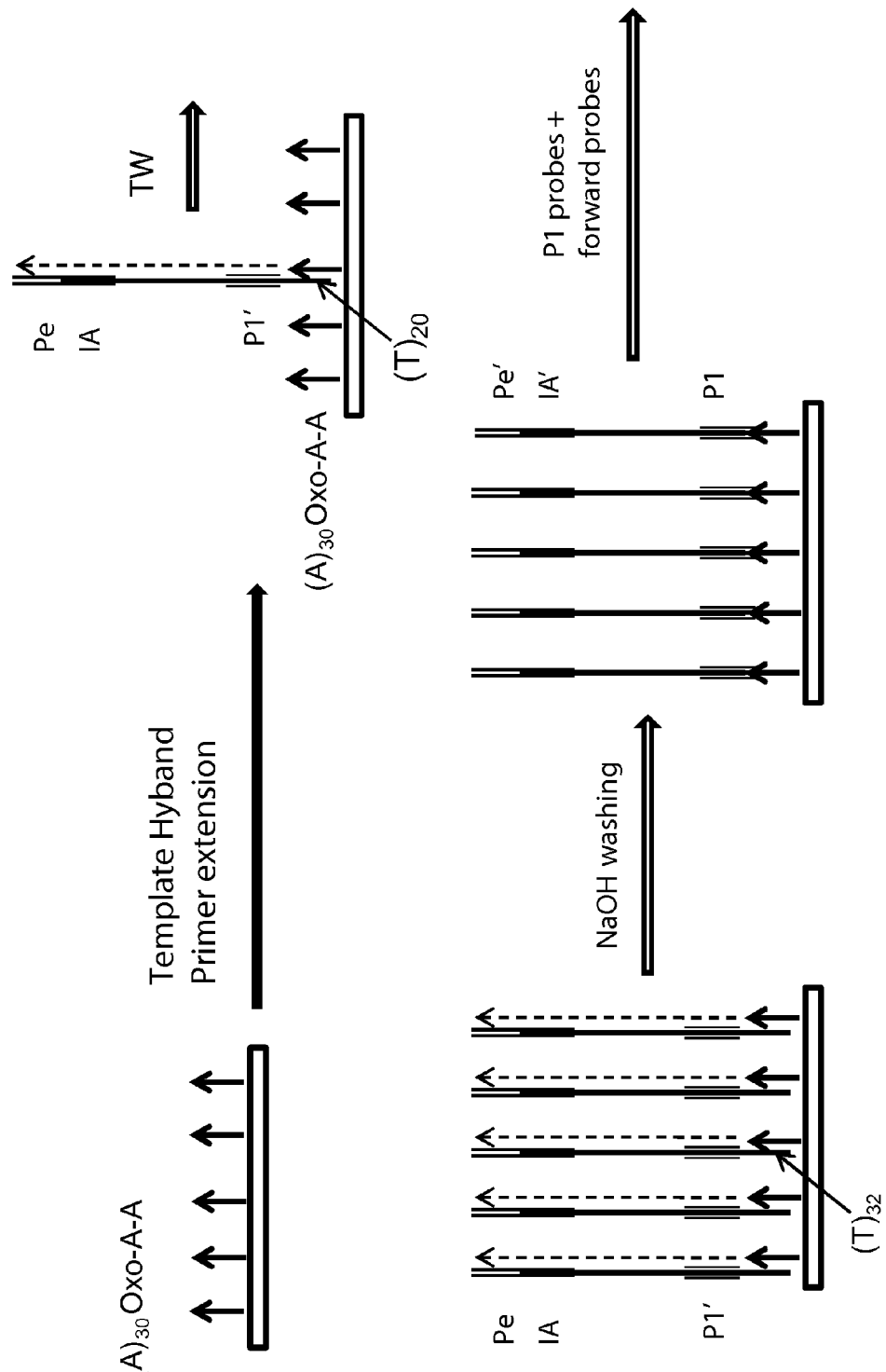
FIGS. 8A-C disclose "$(A)_{30}$", "$(T)_{30}$", "$(T)_{20}$", and "$(T)_{32}$" as SEQ ID NOS:1-3 and 22, respectively.
Figure 8B:
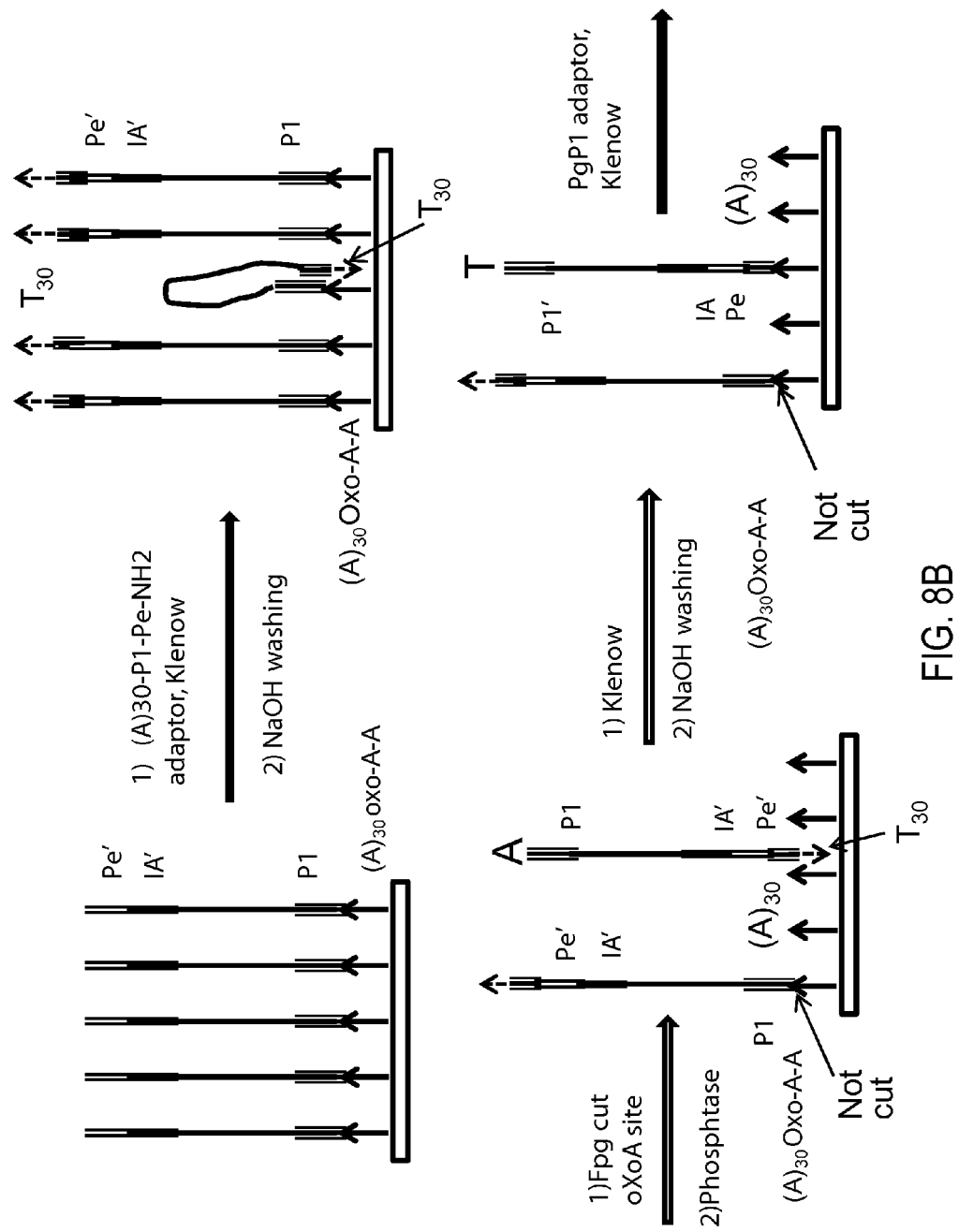
Figure 8C:
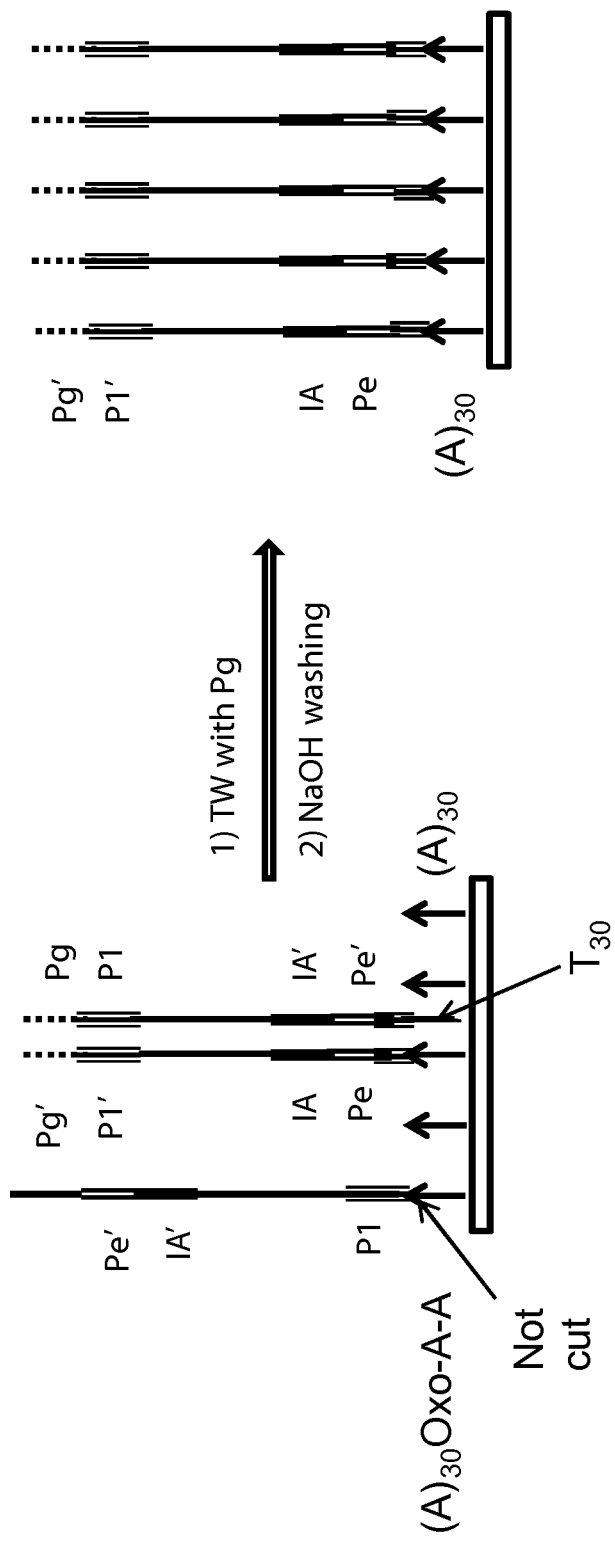

FIG. 8 shows a schematic depiction of an exemplary strand-flipping and walking strategy. (A) Template walking, (B) Strand flipping to generate flipped strands, (C) addition of new primer-binding sequence Pg' on final flipped strands.

I. Methods of Clonal Amplification

Overview

A nucleic acid is associated with (e.g., hybridized to) an appropriate primer, which is optionally immobilized. The hybridized nucleic acid may for convenience be designated as the "template" strand or "reverse strand." This word "template" is not intended to imply any particular functional, structural or sequence relationship with an input nucleic acid that was originally introduced into solution or with a final nucleic acid product that is generated by the amplification process. In an embodiment, a forward primer can hybridize to a first portion of the reverse strand. Another "reverse" primer is optionally present, which is substantially identical to a second non-overlapping portion of the reverse strand. The two portions are for example non-overlapping if they do not contain any subportions that are identical or complementary to each other.

In an embodiment the template strand is optionally single-stranded over at least a portion that is complementary to the forward primer, which portion is designated the forward "primer-binding sequence" or forward PBS. The forward primer is optionally extended using the reverse strand as template to form an extended forward strand, resulting in a duplex between the hybridized template (reverse strand) and the forward strand. At least part of the primer portion of the forward strand can be separated from the hybridized reverse strand. The forward strand comprises a reverse PBS portion that can hybridize to a "reverse" primer and this reverse primer can in turn be extended to form an extended reverse strand. Both the forward and reverse strand can then be separated from each other and the process can be repeated to provide a clonal population of amplified, immobilized nucleic acid molecules.

Optionally, any one or more steps of separating forward and reverse strands from each other involves partial separation, e.g., separation that dissociates a portion of the forward strand from a portion of the reverse strand, but does not abolish all association between the two strands. Optionally, a portion of a forward strand is dissociated from a reverse strand, while another portion of the same forward strand remains associated (e.g., by hybridization) with a reverse strand.

During partial separation, at least a portion of the forward PBS on the reverse strand is dissociated from the first forward strand. However, separation is "partial" because the forward strand and reverse strand remain associated with each other overall. For example, another portion of the reverse strand remains hybridized to the forward strand. Optionally, the denatured portion of the reverse strand re-hybridizes with a second forward primer. Thus a portion of the reverse strand is hybridized to the first forward strand, while another portion of the same reverse strand is hybridized to the second forward primer. The second forward primer is then extended along the reverse strand (using the reverse strand as template) to generate a second forward strand. Repeated cycles of amplification, where an amplification cycle optionally comprises hybridization, =extension and (partial) separation, generate a clonal population of nucleic acids.

Optionally, one or more forward primers are immobilized on a support which lacks any immobilized reverse primers, or vice versa. In an embodiment, the first and second forward primers are immobilized close together or adjacent to each other. The resulting clonal population of nucleic acids comprises forward strands that are immobilized close to or adjacent to each other. In an embodiment, at least $10^6$, $10^8$, $10^{10}$, $10^{12}$, or $10^{14}$ primers are immobilized on a cm$^2$ or a cm$^3$ of an individual support or immobilization site. Optionally, all forward primers are identical in sequence, or have an identical 3' portion.

In alternative embodiments, both the forward and/or reverse primer are optionally immobilized on a support. Alternatively both primers are non-immobilized.

Generally, a nucleic acid is clonally amplified onto a support on which multiple copies of a primer are immobilized. An exemplary nucleic acid is one of a collection of nucleic acids. Individual nucleic acids of the collection for example can have one or more adaptor sequences at their 5' and/or 3' ends and variable sequences in between, such as gDNA or cDNA. In an embodiment, the 3' adaptor has a low $T_m$ region (where $T_m$ is the temperature at which half of the DNA molecules are in non-denatured or double-stranded state and half are in denatured, e.g., random coil, state), and the 5' adaptor optionally has a higher Tm region, or vice versa. The low $T_m$ region is for example an A-rich, T-rich or pyrimidine-rich region, such as an AT (or U)-rich sequence, such as polyT, polyA, polyU and any combinations of A, T and U bases. Exemplary methods are described herein.

The methods described herein can be used for many different purposes, including sequencing, screening, diagnosis, in situ nucleic acid synthesis, monitoring gene expression, nucleic acid fingerprinting, etc.

Non-limiting exemplary methods of clonal nucleic acid amplification on a support are as follows.

A) Amplification on a Support

In some embodiments, the disclosed methods, compositions, systems, apparatuses and kits include nucleic acids (e.g., primers, templates etc.,) that are attached to a support. The nucleic acids can be attached using any suitable method. In some embodiments, the attachment between the nucleic acid molecule and the support is mediated by covalent bonding, by hydrogen bonding (for example attachment of a template nucleic acid to a support mediated by hybridization of the template to another nucleic acid, e.g., primer, which is covalently attached to the support), Van Der Waal's forces, affinity interactions, and the like. Any suitable method for attachment of the nucleic acid sequence to the support can be used, including the use of binding pairs (e.g., avidin/biotin; antigen/antibody). In some embodiments, one member of the binding pair is attached to the support, the other member of a binding pair is attached to the nucleic acid, and the nucleic acid is attached to the support via interaction of the two members of the binding pair.

The support can be comprised of any material and have any dimensions or shape. The support can be selected to have properties or reactivities that interfere only minimally with the amplification process. In some embodiments, the support is comprised of solid material; alternatively, it can be comprised at least partially of semi-solid, fluid or liquid material. In some embodiments, the support is spherical, spheroidal, tubular, pellet-shaped, rod-shaped, octahedral, hexagonal, square or trapezoidal in shape. In some embodiments, the support is porous. In some embodiments, the support can be comprised of a hydrophilic porous matrix such as a hydrogel. See, e.g., U.S. Patent Publication No. 2010-0304982, Hinz et al.; and US Patent Publication No. 2010-0136544, Agresti et al.; all of which foregoing applications are incorporated by reference herein.

Among other things, novel methods of generating a localized clonal population of immobilized clonal amplicons in or on a support are provided. The support can for example be solid or semisolid. The amplified clonal population is optionally immobilized to the support's external surface or can also be within the internal surfaces of a support (e.g., where the support is semisolid, e.g., with a gel or matrix structure). Exemplary supports can be solid or semi-solid. Optionally, the semi-solid support comprises polyacrylamide, cellulose, polyamide (nylon) and cross-linked agarose, dextran and -polyethylene glycol.

Optionally, the disclosed methods and compositions include the attachment of one or more individual members of a collection (e.g., a collection) of nucleic acids to one or more supports of a population of supports. For example, different nucleic acids of the collection can be attached to different supports. The resulting population of supports includes a plurality of supports each comprising a single nucleic acid. In some embodiments, the nucleic acids of the collection are double stranded, and the collection is denatured to form a population of single-stranded nucleic acids. In some embodiments, the support includes primers, and one or more of the single stranded nucleic acids can be attached to the support through hybridization to primers on the surface.

Optionally before amplification the collection of nucleic acids can be appropriately diluted and contacted with the population of supports in solution, such that at least 40%, 50%, 60%, 70%, 80%, 90% or 95% of the supports (or immobilization sites where the population of supports consists of one or a few supports) become attached to no more than one nucleic acid. In some embodiments, the ratio of the number of nucleic acids to the total number of supports can be set to facilitate mono-clone formation by, e.g., maximizing the number of resulting supports (or number of immobilization sites on a single support) that include only a single nucleic acid, or choosing a ratio that is statistically predicted to give more clonal supports (e.g., beads) than lower or higher ratios.

Optionally, a single support is used in any of the amplification methods herein, where the single support has a plurality of primers that can hybridize to the templates. In such an embodiment, the concentration of the template collection is adjusted before it is contacted with a solid support so that individual template molecules in the collection get attached or associated (e.g., by hybridization to primers immobilized on the solid support) at a density of at least $10^2$, $10^3$, $10^4$, $10^5$, $4\times10^5$, $5\times10^5$, $6\times10^5$, $8\times10^5$, $10^6$, $5\times10^6$ or $10^7$ molecules per $mm^2$.

Optionally, individual template molecules are amplified in-situ on the support, giving rise to clonal populations that are spatially-centered around the point of hybridization of the initial template. Optionally, the amplification generates no more than about $10^2$, $10^3$, $10^4$, $10^5$, $10^6$, $10^7$, $10^8$, $10^9$, $10^{10}$, $10^{11}$, $10^{12}$, $10^{15}$, or $10^{20}$ amplicons from a single amplified template. Optionally, the colonies of clonal amplicons are situated on the solid support at a density of at least $10^2$, $10^3$, $10^4$, $10^5$, $4\times10^5$, $5\times10^5$, $6\times10^5$, $8\times10^5$, $10^6$, $5\times10^6$ or $10^7$ molecules per $mm^2$.

In some embodiments, the nucleic acid collection can be contacted with one or more supports under conditions where multiple nucleic acids bind to the same support. Such contacting can be particularly useful in methods that involve parallel clonal amplification of nucleic acids in different regions of the same support. The ratio of the number of nucleic acids to the surface area of the support can be adjusted to facilitate mono-clone formation by, e.g., ensuring that the nucleic acids are appropriately spaced in the support to favor formation of monoclonal populations of amplified nucleic acids without substantial cross-contamination between different clonal populations. For example where a single support us used, the collection of nucleic acids to be amplified is adjusted to such a dilution that the resulting amplified clonal populations generated from individual nucleic acids are generally discrete or distinct, e.g., without overlap. For example, individual nucleic acids within 50%, 70%, 80% or 90% or more of the amplified clonal populations are not interspersed with substantially non-identical nucleic acids. Optionally, different amplified populations are not in contact or completely overlapping with other amplified populations, or are distinguishable from each other using a detection method of choice.

In some embodiments, the nucleic acids are attached to the surface of a support. In some embodiments, the nucleic acids can be attached within the support. For example, for supports comprised of hydrogel or other porous matrices, the nucleic acids can be attached throughout the volume of the support including on the surface and within the support.

In some embodiments, the support (or at least one support in a population of supports) can be attached to at least one primer, optionally to a population of primers. For example, the support (or at least one support) can include a population of primers. The primers of the population can be substantially identical each other, or may include a substantially identical sequence. One, some or all of the primers can include a sequence that is complementary to a sequence within one or more nucleic acid templates. In some embodiments, the population of primers can include at least two noncomplementary primers.

The primers can be attached to the support through their 5' end, and have free 3' ends. The support can be the surface of a slide or the surface of a bead. The primers have low melting temperature, such as oligo $(dT)_{20}$ (SEQ ID NO:3), and can hybridize to the low $T_m$ region of the collection adaptor. The distances between the primers need to be shorter than the adapter length to allow templates waking, or alternatively, a long primer with 5' end long linker will increase the chance of walking.

In some embodiments, the support is attached to and/or contacted with a primer and a template (or reverse strand) under conditions where the primer and template hybridize to each other to form a nucleic acid duplex. The duplex can include a double stranded portion that comprises complementary sequences of the template and primer, where at least one nucleotide residue of the complementary sequences are base paired with each other. In some embodiments, the duplex can also include a single stranded portion. The duplex can also include a single stranded portion. The single stranded portion can include any sequence within the template (or primer) that is not complementary to any other sequence in the primer (or template).

A non-limiting exemplary method of clonal nucleic acid amplification on a support is as follows. A nucleic acid (which shall be designated for convenience as the reverse strand) is clonally amplified onto a support on which multiple copies of a complementary forward primer are attached. An exemplary nucleic acid is one of a plurality of DNA collection molecules, that for example the plurality of nucleic acid members have one or more common ("adaptor") sequences at or near their 5' and/or 3' ends and variable sequences in between, such as gDNA or cDNA. In an embodiment, the 3' common portion, e.g., adaptor, has a breathable (e.g., low $T_m$) region, and the 5' common sequence (e.g., adaptor) optionally has a less breathable (e.g., higher $T_m$) region, or vice versa. In another embodiment, both the 5' and 3' common sequences are breathable. The breathable (e.g., low $T_m$) region is for example a region that is rich in A, T and/or U, such as an AT (or U)-rich sequence, such as polyT, polyA, polyU and any combinations of A, T and U bases, or bases complementary to such bases. Exemplary methods are described herein.

One non-limiting exemplary method of clonal nucleic acid amplification on a support is shown in FIG. 1. A non-limiting description of an exemplary method is as follows.

A double stranded DNA library molecule is denatured and the single stranded DNA is attached to the support through hybridization to the primers on the surface. The ratio of number of DNA molecules to support area or number of beads is set to facilitate mono-clone formation.

Primers are attached on a support through their 5' and have free 3'. The support can be the surface of a slide or the surface of a bead. The primers have low melting temperature, such as oligo $(dT)_{20}$ (SEQ ID NO:3) or oligo $(dA)_{30}$ (SEQ ID NO:1) and can hybridize to the low Tm region of the library adaptor. The distances between the primers can be shorter than the adapter length to allow templates waking, or alternatively, a long primer with 5' end long linker will increase the chance of walking.

A nucleic acid is clonally amplified onto a support on which multiple copies of a primer are attached. An exemplary nucleic acid is one of a plurality of DNA library molecules, which for example have one or more common (e.g., "adaptor") sequences at their 5' and/or 3' ends and variable sequences in between, such as gDNA or cDNA. In an embodiment, the 3' adaptor has a low Tm region, and the 5' adaptor optionally has a higher Tm region, or vice versa. The low Tm region is for example a pyrimidine-rich region, such as an AT (or U)-rich sequence, such as polyT, polyA, polyU and any combinations of A, T and U bases or bases complementary to such bases. Exemplary methods are described herein.

B) Primer Extension

One or more primers, whether in soluble form or attached to a support, is incubated with a DNA polymerization or extension reaction mix, which optionally comprises any one or more of reagents such as enzyme, dNTPs and buffers. The primer (e.g., a forward primer) is extended. Optionally, the extension is a template-dependent extension of a primer along a template comprising the successive incorporation of nucleotides that are individually complementary to successive nucleotides on the template, such that the extended or non-extended forward primer is complementary to the reverse strand (also termed antiparallel or complementary). Optionally, the extension is achieved by an enzyme with polymerase activity or other extension activity, such as a polymerase. The enzyme can optionally have other activities including 3'-5' exonuclease activity (proofreading activity) and/or 5'-3' exonuclease activity. Alternatively, in some embodiments the enzyme can lack one or more of these activities. In an embodiment the polymerase has strand-displacing activity. Examples of useful strand-displacing polymerases include Bacteriophage 029 DNA polymerase and Bst DNA polymerase. Optionally, the enzyme is active at elevated temperatures, e.g., at or above 45° C., above 50° C., 60° C., 65° C., 70° C., 75° C., or 85° C.

An exemplary polymerase is Bst DNA Polymerase (Exonuclease Minus), is a 67 kDa *Bacillus stearothermophilus* DNA Polymerase protein (large fragment), exemplified in accession number 2BDP_A, which has 5'-3' polymerase activity and strand displacement activity but lacks 3'-5' exonuclease activity. Other polymerases include Taq DNA polymerase I from *Thermus aquaticus* (exemplified by accession number 1TAQ), Eco DNA polymerase I from *Echerichia coli* (accession number P00582), Aea DNA polymerase I from *Aquifex aeolicus* (accession number 067779), or functional fragments or variants thereof, e.g., with at least 80%, 85%, 90%, 95% or 99% sequence identity at the nucleotide level.

Generally, the extension step produces a nucleic acid, which comprises a double-stranded duplex portion in which two complementary strands are hybridized to each other. In one embodiment, walking involves subjecting the nucleic acid to partially-denaturing conditions that denature a portion of the nucleic acid strand but are insufficient to fully denature the nucleic acid across its entire length. In an embodiment, the nucleic acid is not subjected to fully-denaturing conditions during a portion or the entire duration of the walking procedure. As intended herein, a nucleic acid molecule can be considered partially-denatured when a portion of at least one strand of the nucleic acid remains hybridized to a complementary strand, while another portion is in an unhybridized state (even if it is in the presence of a complementary sequence). The unhybridized portion is optionally at least 5, 7, 8, 10, 12, 15, 17, 20, or 50 nucleotides long. The hybridized portion is optionally at least 5, 7, 8, 10, 12, 15, 17, 20, or 50 nucleotides long.

Optionally, a nucleic acid can be considered to be partially denatured when a substantial fraction of individual molecules of the nucleic acid (e.g., above 20%, 30%, 50%, or 70%) are in a partially denatured state. Optionally less than a substantial amount of individual molecule are fully denatured, e.g., not more than 5%, 10%, 20%, 30% or 50% of the nucleic acid molecules in the sample. Similarly a nucleic acid is optionally considered fully denatured when it lacks any double-strandedness (or lacks any hybridization to a complementary strand) in more than 80% or 90% of individual molecules of the nucleic acid. Under exemplary conditions at least 50% of the nucleic acid is partly denatured, but less than 20% or 10% is fully denatured. In other situations, at least 30% of the nucleic acid is partly denatured, but less than 10% or 5% is fully denatured. Similarly, a nucleic acid can be considered to be non-denatured when a minority of "breathable" portions of interest in the nucleic acid, e.g., a PBS, are denatured. In exemplary annealing conditions at least 10%, 30%, 50%, 60%, 70%, 80% or 90% of PBSs of nucleic acid molecules in the sample are hybridized to corresponding primers.

In an embodiment, partially denaturing conditions are achieved by maintaining the duplexes as a suitable temperature range. For example, the nucleic acid is maintained at temperature sufficiently elevated to achieve some heat-denaturation (e.g., above 45° C., 50° C., 55° C., 60° C., 65° C., or 70° C.) but not high enough to achieve complete heat-denaturation (e.g., below 95° C. or 90° C. or 85° C. or 80° C. or 75° C.). Complete heat-denaturation conditions are for example conditions that would result in complete separation of a significant fraction (e.g., more than 10%, 20%, 30%, 40% or 50%) of a large plurality of strands from their extended and/or full-length complements. In an embodiment the nucleic acid is subjected to isothermal conditions, where temperature variation is constrained within a limited range during at least some portion of the amplification (e.g., the temperature variation is within 20° C., optionally within 10° C., for example within 5° C., or 2° C.). Optionally, the temperature is maintained at or around 50° C., 55° C., 60° C., 65° C., or 70° C. for at least about 10, 15, 20, 30, 45, 60 or 120 minutes. Optionally, any temperature variation is not more than 20° C., optionally within 10° C., for example within 5° C., or 2° C. during one or more amplification cycles (e.g., e.g., 1, 5, 10, 20, or all amplification cycles performed). Optionally, thermocycling can be performed (where temperature variance is within isothermal or non-isothermal ranges). In an example, the temperature variation is constrained between the denaturation step and another step such as annealing and/or extension. In an example, the difference between the denaturation temperature and the annealing or extension temperature is not more than 20° C., optionally within 10° C., for example within 5° C., or 2° C., for one or more cycles of amplification. The temperature is for example constrained for at least 5, 10, 15, 20, 30, 35 or substantially all cycles of amplification.

Partial denaturation can also be achieved by other means, e.g., chemical means using chemical denaturants such as urea or formamide, with concentrations suitably adjusted, or using high or low pH (e.g., pH between 4-6 or 8-9). In an embodiment, partial denaturation and amplification is achieved using recombinase-polymerase amplification (RPA). Exemplary RPA methods are described herein.

In an embodiment, the sequence of the negative and/or positive strand designed such that a primer-binding sequence or a portion thereof is breathable, i.e., is susceptible to denaturation under the conditions of choice (e.g., amplification conditions). The breathable portion is optionally more susceptible than a majority of nucleic acids of similar length with randomized sequence, or more susceptible than at least another portion of the strand comprising the breathable sequence. Optionally, the breathable sequence shows a significant amount of denaturation (e.g., at least 10%, 20%, 30%, 50%, 70%, 80%, 90% or 95% of molecules are completely denatured across the breathable sequence) at the amplification conditions of choice. For example the breathable sequence is designed to be fully-denatured in 50% of strand molecules at 30, 35, 40, 42, 45, 50, 55, 60, 65 or 70° C. under the conditions of choice (e.g., amplification conditions).

Optionally, the $T_m$ of a nucleic acid strand (e.g., a primer or template strand) is the temperature at which at least a desired fraction of a clonal population of duplexes are rendered completely single-stranded under the chosen reagent conditions, where an individual duplex comprises the nucleic acid strand in question hybridized to its full-length complement. By default, the desired fraction is 50% if the fraction is not specified. In alternative embodiments, the desired fraction is optionally at least 10%, 20%, 30%, 40%, 50%, 60%, 65%, 70%, 75%, 80%, 85%, 90%, 95% or 99%. Also for example a sequence can be considered breathable if the theoretically-predicted melting temperature of the breathable sequence is not more than 20, 30, 35, 40, 45, 50, 55, 60 or 65° C. under the amplification conditions of choice, using known theoretical calculations for predicted melting temperature ($T_m$). In an example, the thermal stability, melting behavior and/or $T_m$ is a theoretically-predicted temperature according to the teachings of Breslauer et al., Proc. Nat. Acad. Sci. 83, 3746-50 (1986). In an exemplary calculation, $T_m$ is predicted as follows:

$$T_m = \frac{\Delta H \frac{\text{kcal}}{C*\text{Mol}}}{\Delta S + R \ln([\text{primer}]/2)} - 273.15° \text{ C.}$$

where $\Delta H$ is the enthalpy of base stacking interactions adjusted for helix initiation factors; $\Delta S$ is the entropy of base stacking adjusted for helix initiation factors, and for the contributions of salts to the entropy of the system, and R is the universal gas constant (1.987 Cal/° C.*Mol). Further details and assumptions are set forth in SantaLucia, J. (1998) Proc. Nat. Acad. Sci. USA 95, 1460); Rychlik, W. and Rhoads, R. E. (1989) Nucl. Acids Res. 17, 8543; and Borer P. N. et al. (1974) J. Mol. Biol. 86, 843.

In another embodiment the $T_m$ is empirically measured by known methods. (e.g., Spink, Methods Cell Biol. 2008; 84:115-41; Meunier-Prest et al., Nucleic Acids Res. 2003 Dec. 1; 31(23): e150; Brewood et al., Nucleic Acids Res. 2008 September; 36(15): e98.)

In an embodiment, at least one PBS on each strand is breathable—e.g., the forward PBS and the reverse PBS are both breathable. Optionally, a nucleic acid such as a forward or reverse strand comprises two breathable sequences. For example, a 5' portion and a 3' portion can be breathable.

Where partial denaturation is achieved by heating or elevated temperatures, an exemplary breathable PBS may be pyrimidine-rich (e.g., with a high content of As and/or Ts and/or Us). The PBS comprises for example a poly-A, poly-T or poly-U sequence, or a polypyrimidine tract. One or more amplification or other primers (e.g., an immobilized primer) are optionally designed to be correspondingly complementary to these primer-binding sequences. An exemplary PBS of a nucleic acid strand comprises a poly-T sequence, e.g., a stretch of at least 10, 15, 20, 25 or 30 thymidine nucleotides, while the corresponding primer has a complementary sequence to the PBS, e.g., a stretch of at least 10, 15, 20, 25 or 30 adenosine nucleotides. Exemplary low-melt primers optionally have a high proportion (e.g., at least 50%, 60%, 65%, 70%, 75%, 80%, 85% 90% 95% or 100%) of nucleobases that generally (e.g., under amplification conditions of choice) form no more than two hydrogen bonds with a complementary base when the primer is hybridized to a complementary template. Examples of such nucleobases include A (adenine), T (thymine) and U (uracil). Exemplary low-melt primers optionally have a high proportion of any one or more of A (adenine), T (thymine) and/or U (uracil) nucleotides or derivatives thereof. In an embodiment, the derivatives comprise nucleobases that are complementary to A (adenine), T (thymine) and/or U (uracil). The portion of the primer that hybridizes to the PBS optionally has at least 50%, 60%, 65%, 70%, 75%, 80%, 85%, 90% 95% or 100% of A (adenine), T (thymine) or U (uracil) nucleotides, or any combination thereof. In another example, the portion of the primer that hybridizes to the PBS comprises a polyA sequence (e.g., at least 5, 10, 15, 20, 25 or 30 nucleotides long). Other exemplary primers comprise $(NA_x)_n$ (SEQ ID NO:4) repeats. Optionally, n (in lower case) is from 2 to 30, e.g., from 3 to 10, for example 4 to 8. "N" (in upper case) is any nucleotide—and optionally, N is C or G. "A" is the shorthand convention for adenine, and "x" denotes the number of adenine residues in the repeat, for example 2, 3, 4, 5, 6, 10 or more. Exemplary primers comprise multiple repeats of $(CAA)_n$ (SEQ ID NO:5), $(CA)_n$ (SEQ ID NO:6), $(CAAA)_n$ (SEQ ID NO:7) or even $(GAA)_n$ (SEQ ID NO:8).

Optionally only one strand (e.g., the forward or the reverse strand) has a breathable PBS. In another embodiment, both the forward and reverse strands have a breathable PBS. The breathable PBS is optionally complementary to a primer that is either immobilized to a support or is not immobilized (e.g., in soluble form). Optionally the strand comprising the breathable PBS is either immobilized to a support or is not immobilized (e.g., in soluble form). Optionally both primers are immobilized, or both strands are immobilized. Optionally neither primer is immobilized, or neither strand is immobilized.

An amplification cycle optionally comprises breathing, annealing and extension. The nucleic acid to be amplified is optionally subjected to conditions which are suitable for or optimized for at least one of these steps. In an embodiment, the nucleic acid is subjected to conditions which are suitable for more than one of these steps, (e.g., annealing and extension, or breathing and extension). In some instances, all three of these steps can take place simultaneously under the same conditions.

In an exemplary method the nucleic acid can be subjected to conditions which permit or facilitate breathing. In an embodiment, "breathing" is said to occur when the two strands of a double-stranded duplex are substantially hybridized to each other, but are denatured across a local portion of interest (e.g., the terminal ends or primer-binding sites). One or more breathable sequences (e.g., a forward and/or reverse PBS having a low Tm portion) of the nucleic acid gets locally denatured ("breathes") from a first complementary strand (e.g., a forward or reverse strand) which it is hybridized to, and is thus made available to hybridize to another second strand. An exemplary first strand is a primer extension product from a first primer. An exemplary second strand is for example a second unextended primer (e.g., a PBS-complementary oligonucleotide comprising, e.g., a dT or dA sequence). Optionally, the first and second strands are immobilized on a support, and can be closely situated (e.g., in close enough proximity to allow walking). The conditions for breathing are optionally partially-denaturing conditions under which the PBS is generally denatured but another portion of nucleic acid remains in a hybridized or double-stranded state. Optionally, DNA helicase can be included in the reaction mix to facilitate the partial denaturing.

Optionally, the nucleic acid is then subjected to conditions which facilitate annealing, e.g., the temperature is decreased, to enable hybridization between the breathable PBS and the second strand. In an embodiment, the same conditions are used to facilitate both breathing and extension. In another embodiment, annealing conditions are different from breathing conditions—for example, the annealing conditions are nondenaturing conditions or conditions that favor denaturation less than the breathing conditions. In an example, annealing conditions involve a lower temperature (such as 37° C.) than breathing conditions, in which a higher temperature (e.g., 60-65° C.) is used. Optionally, fully denaturing conditions are avoided during one or more cycles of amplification (e.g., the majority of amplification cycles or substantially all amplification cycles).

Extension conditions are generally permissive or highly suitable for primer extension. In an embodiment, the extension conditions of choice are the same as or different from annealing and/or breathing conditions. In an embodiment, the same set of conditions is used for all three steps (e.g., isothermal amplification), such that subjecting the sample to a single set of conditions for a sustained period enables multiple amplification cycles of breathing, annealing and extension to take place.

In an embodiment, strand extension is performed for example by a strand displacing DNA polymerase, such as Bst DNA polymerase large fragment, Klenow DNA polymerase, phi29 DNA polymerase, Vent DNA polymerase, any functional fragments and/or variants, or any combination of such enzymes. The strand-displacement capability optionally facilitates extension through duplex portions of partially-denatured nucleic acids.

Optionally, one or more of the PBS-breathing and primer extension steps are repeated multiple times to amplify an initial nucleic acid. Where one or more nucleic acid reagents (e.g., primers) are immobilized to a support, the primer-extension products remain substantially attached to the support, e.g., by virtue of attachment of an unextended extended primer to the support prior to amplification, or by hybridization to such a primer). Optionally, a localized clonal population of clonal amplicons is formed around a discrete site on the support. An exemplary discrete site is a point of attachment of an initial nucleic acid strand to the support, and from which other nucleic acids within the clonal population are directly or indirectly generated by primer extension, using the initial nucleic acid or its copies as a template.

Optionally, a sample is prepared of a population of one or more nucleic acids to be amplified. The population of nucleic acids can be in single-stranded or double-stranded form; optionally one or more nucleic acids individually comprises a nucleic acid strand with a known 3' end sequence and a known 5' end sequence which are substantially identical or complementary to the one or more primers used in the amplification. A 3' portion of the nucleic acid strand can for example be complementary to an immobilized primer, whereas a 5' portion can be identical to a soluble primer. The 5' and/or 3' portions can be common ("universal") or invariant between individual nucleic acids within the population. Optionally, the nucleic acids within the population individually comprise variant (e.g., unknown) sequence between the common portions, such as genomic DNA, cDNAs, mRNAs, mate-pair fragments, exomes. etc. The collection can for example have enough members to ensure over 50%, 70%, or 90% coverage of the corresponding genetic source (e.g., the genome or the exome).

II. Compositions, Arrays and Kits

Also provided herein is a composition comprising any one or any subset or all of the following: at least one reverse nucleic acid strand, a plurality of forward primers immobilized on at least one support, a plurality of reverse primers in solution, and a polymerase. The forward and/or reverse primers are optionally low-melt or rich in adenine, thymine or uracil as described herein. An exemplary composition comprises clonal populations of nucleic acid strands ("reverse strands"), where individual reverse strands of each clonal population comprise a low-melt (e.g., breathable) primer-binding sequence at the 3' end and/or a low-melt primer sequence on the 5' end. The composition optionally includes a plurality of reverse primers that are substantially identical to the low-melt primer sequence on a 5' portion or end of the reverse strand. The composition optionally includes a plurality of forward primers that are substantially complementary to the low-melt primer-binding sequence on a 3' portion or end of the reverse strand. In an embodiment the forward primer and/or the reverse primer is immobilized by attachment to a support. For example the forward primer is immobilized and the reverse primer is not immobilized, or vice versa. An exemplary composition comprises any one or more of: (1) a reverse nucleic acid strand, (2) a plurality of low-melt forward primers immobilized on a support, (3) a plurality of low-melt reverse primers in solution, and (4) a polymerase.

Optionally, the composition further comprises one or more extended forward strands that are longer than unextended forward primers and are optionally full-length complements of one or more reverse strands. In an embodiment one or more extended forward strands are hybridized to a complementary reverse strand, where the reverse strand is optionally also hybridized to another different forward primer or to a different forward strand. The different forward strand is optionally a less-than-full-length complement of the reverse strand. The composition can contain any one or more reagents described herein, and/or be subjected to any one or more procedures or conditions (e.g., temperatures) described herein.

Optionally, the composition comprises a plurality of spatially-separated clonal populations are attached to one or more solid supports. For example, a plurality of spatially-separated clonal populations are attached to the same support. The composition is optionally free of another enzyme that is not a polymerase, e.g., a recombinase or reverse transcriptase or helicase or nicking enzyme.

Optionally the composition comprises a collection of nucleic acids producible by any one or more methods described herein. For example, the collection can comprise immobilized nucleic acids which occupy one or more distinct areas on a surface, each area comprising a plurality of identical nucleic acid strands and optionally, a plurality of identical complementary strands hybridized thereto, where the complementary strands have no attachment or linkage or association with the solid support except by virtue of hybridization to the immobilized nucleic acid. Optionally, an individual nucleic acid strand within such an area is located so that another nucleic acid strand is located on the surface within a distance of the length of that strand. Optionally there is at least one distinct area present per $mm^2$ of surface on which the nucleic acids are immobilized. For example the number of distinct areas/$mm^2$ of surface on which the nucleic acids are immobilized is greater than $10^2$, greater than $10^3$, greater than $10^4$, greater than $10^5$, greater than $10^6$, greater than $10^7$, or greater than $10^8$.

The collections of amplified clonal populations can form arrays, which can be one-dimensional (e.g., a queue of generally monoclonal microbeads) or two-dimensional (e.g., the amplified clonal populations are situated on a planar support), or three-dimensional. The individual clonal populations of an array are optionally but not necessarily situated or arranged such that they are addressed or addressable. Optionally, different clonal populations are spaced at an appropriate distance from one another, which distance is generally sufficient to permit different clonal populations to be distinguished from each other. In an embodiment, localized clonal populations are scattered in an ordered or disordered, e.g., random, pattern over a planar substrate.

The features of an exemplary array are individual distinguishable clonal populations of nucleic acids, where optionally the features are distributed over one or more supports. In an exemplary microbead embodiment, an array comprises a plurality of microbeads, where an individual microbead generally comprises a monoclonal population of nucleic acids, and different microbeads generally comprise different clonal populations (e.g., which differ in sequence). Optionally, the microbeads are distributed or packed in a monolayer over a planar substrate. In other embodiments, the array comprises a single (e.g., planar) support, the single support comprising a plurality of spatially discrete clonal populations of nucleic acids, where different clonal populations optionally differ in sequence.

Optionally, one or more nucleic acids within individual clonal populations can be attached to the planar substrate directly. In another example, the nucleic acids of individual clonal populations are attached to microbeads, for example as discussed herein. The clonal microbeads are optionally packed closely together over a planar substrate, in random or ordered fashion. Optionally, more than 20%, 30%, 50%, 70%, 80%, 90%, 95% or 99% of the microbeads are in contact with at least one, two, four or six other microbeads. Optionally, less than 10%, 20%, 30%, 50%, 70%, 80%, 90%, 95% or 99% of the microbeads are in contact with one, two, four or six other microbeads.

Optionally the features of an array (such as immobilization sites or amplified DNA clonal populations) are generally discrete or distinct from each other. For example, 50%, 70%, 80% or 90% or more of the features of an array are not in contact or not completely overlapping with other features on the same array, or are distinguishable from each other using a detection method of choice. Optionally, the features can partially overlap with each other as long as they remain distinguishable from each other.

Also provided herein are kits comprising any one or more reagents (e.g., nucleic acids or enzymes or supports) described herein. For example a kit can contain one or more primers, optionally immobilized. An exemplary kit comprises two primers, where the denaturation temperature of one primer is optionally at least 10, 20, 30 or 40° C. from the other. Optionally the lower-melting primer comprises a adenine/thymine/uracil-rich portion such as a polyA tract such as those described herein, e.g., a polyA, T or U sequence that is at least 10, 15, 20, 25 or 30 nucleotides long. The lower-melting primer is optionally immobilized, where the higher-melting primer is optionally non-immobilized.

Optionally, the kit further contains one or more supports described herein, comprising the immobilized primers. An exemplary support comprises a planar surface. Where multiple supports are used, the kit can comprise microbeads bearing identical primers.

The kit optionally contains one or more polymerases, e.g., a strand-displacing polymerase, and/or any combination of amplification reagents described herein.

The kit can also comprise instructions for diluting an initial population of templates to be amplified, and/or a dilution medium.

III. Uses

The amplified and/or immobilized nucleic acid molecules generated from methods described herein can be subjected to many different applications, including sequencing, screening, diagnosis, in situ nucleic acid synthesis, monitoring gene expression, nucleic acid fingerprinting, forensics, diagnostics, etc.

Any method or plurality of nucleic acids described herein can be used in providing nucleic acid molecules for sequence analysis. For example, one or more nucleic acid molecules (e.g., amplicons) produced by any method described herein can be contacted with at least one sequencing analysis primer and/or at least one probe. Optionally, at least one sequencing analysis primer is or comprises an oligonucleotide. In an embodiment, at least one probe comprises one or more nucleotides or one or more oligonucleotides. Oligonucleotides used as sequence analysis primers or probes for example can hybridize to at least one of the same sequences as at least one immobilization primer, e.g., the oligonucleotides optionally have the same sequences as the immobilization primers.

In an embodiment, sequence analysis is performed by contacting one or more target nucleic acid molecules to be analyzed with one or more sequence analysis primers and/or probes, removing any unhybridized probes and determining the label of the ligated probe.

In another embodiment, sequence analysis is performed by contacting one or more target nucleic acid molecules to be analyzed with one or more sequence analysis primers and/or probes, and detecting any resulting hybridization between at least one target nucleic acid and at least one labeled sequence analysis primer and/or probe. In an embodiment the sequence analysis method comprises extending one or more sequence analysis primers hybridized to target nucleic acid molecules by ligating any adjacently-hybridized oligonucleotides probes to the sequence analysis primer, removing any unligated probes and determining the label of the ligated probe.

In another embodiment, sequence analysis is performed by contacting one or more target nucleic acid molecules to be analyzed with one or more sequence analysis primers and labeled nucleotide probes and a template-dependent polymerase, allowing the polymerase to incorporate a labeled nucleotide into a polymerase extension product of the sequence analysis primer, removing any unincorporated nucleotides, and determining the identity of the incorporated nucleotide. The nucleotide probes are for example fluorescently-labeled, and/or the identity of the incorporated nucleotide is determined from its label. In another embodiment the nucleotide probe is not labeled and the presence or incorporation of the nucleotide into a polymerase extension product is measured by virtue of a by-product generated by incorporation. For example, incorporation of a nucleotide into an extension product is optionally detected by measuring changes in pH or ions or an electric current, for example by using a field-effect transistor.

In any method described herein, the probe (e.g., a nucleotide or an oligonucleotide) is optionally further extendable by polymerase or ligase. Alternatively, the probe is optionally not extendable by a polymerase or ligase. Such non-extendable probes are optionally rendered extendable during the sequence analysis process (e.g., after their identity is determined). Optionally, nucleotide probes include A, G, C, T bases, where nucleotide probes with a different base at the interrogation position of the probe have a different fluorescent label.

Optionally, all or less than all (e.g., at least one) sequencing analysis primer or sequencing analysis probe comprises a labeled nucleotides/oligonucleotides. Optionally, the labeled nucleotides/oligonucleotides all have the same label or are differentially labeled. In an embodiment the labeled nucleotides/oligonucleotides are fluorescence labeled. For example a mixture of labeled and non-labeled nucleotides is used.

Optionally a plurality of different sequences are determined in parallel. For example, the sequence analysis is parallel sequence analysis of nucleic acid molecules present in at least 2, e.g., at least 10, 1000, 1000, 106, 109 or 1012 different distinct areas. The sequence analysis technology can be polymerase-based sequence analysis, for example Sanger sequence analysis. Examples of sequence analysis technology include sequence analysis by synthesis, or sequence analysis using reversible terminators, or ligation based sequence analysis, e.g., two-base encoding using SOLiD.

Also provided is an apparatus for performing any method described herein, comprising any one or more reagents or devices mentioned herein. For example the apparatus can comprise one or more supports, each support comprising a plurality of immobilized primers (which are optionally identical). For example the apparatus can comprise a nucleic acid polymerase or ligase, and/or a plurality of nucleotides (optionally labeled) and means for partially separating annealed nucleic acid strands. Exemplary means for separating annealed nucleic acid strands comprises a controlled heating means, e.g., a heating means that can maintain the reagents at a constant temperature. The apparatus optionally comprises a source of one or more reactants described herein and detector means for detecting one or more signals produced after one or more of said reactants have been applied to said nucleic acid molecules. The means for detecting optionally has sufficient resolution to distinguish between the distinct immobilization sites of the support, or between multiple supports (if in the form of microbeads). Optionally, the apparatus comprises a support which has primers immobilized on a planar surface.

In an embodiment the apparatus comprises a charge coupled device (CCD), which optionally is operatively connected with an imaging device.

In an embodiment each immobilization site is a separate bead, and wherein each bead comprises a clonal population of amplicons after amplification. Optionally, each bead can be distributed into or on an array before, during or after amplification. The array for example is any array of wells, where beads bearing amplicons are distributed individually into separate wells. Optionally the array is a large-scale FET array.

Optionally, at least some of the clonal populations generated by any method herein appear discrete from each other when detected or analyzed (e.g., by optical or electrochemical detection) and/or spatially separated. In an embodiment where nucleotide incorporation is detected by the generation of H+ ions, such ions can only diffuse a short distance, for example <100 nm in a buffer solution. This limited capacity for diffusion ensures H+ generated in one clonal population will generally not interfere with nearby clonal populations and will only be significantly detectable by the sensor directly under the clonal population.

Paired End Sequencing

In some embodiments, the present teachings provide methods for paired end sequencing. In some embodiments, a paired end sequencing reaction can include conducting a sequencing reaction in both directions (e.g., forward and reverse directions). In some embodiment, paired end sequencing can be conducted on any template polynucleotide which comprises at least one scissile moiety. Optionally, the template polynucleotide also comprises at least one cross linking moiety. In some embodiments, a template polynucleotide comprises at least one scissile moiety, or comprises at least one scissile moiety and at least one cross linking moiety.

In some embodiments, a paired end sequencing reaction comprises: (a) a forward sequencing step; (b) a cleavage step, and (c) a reverse sequencing step.

Figure 9:
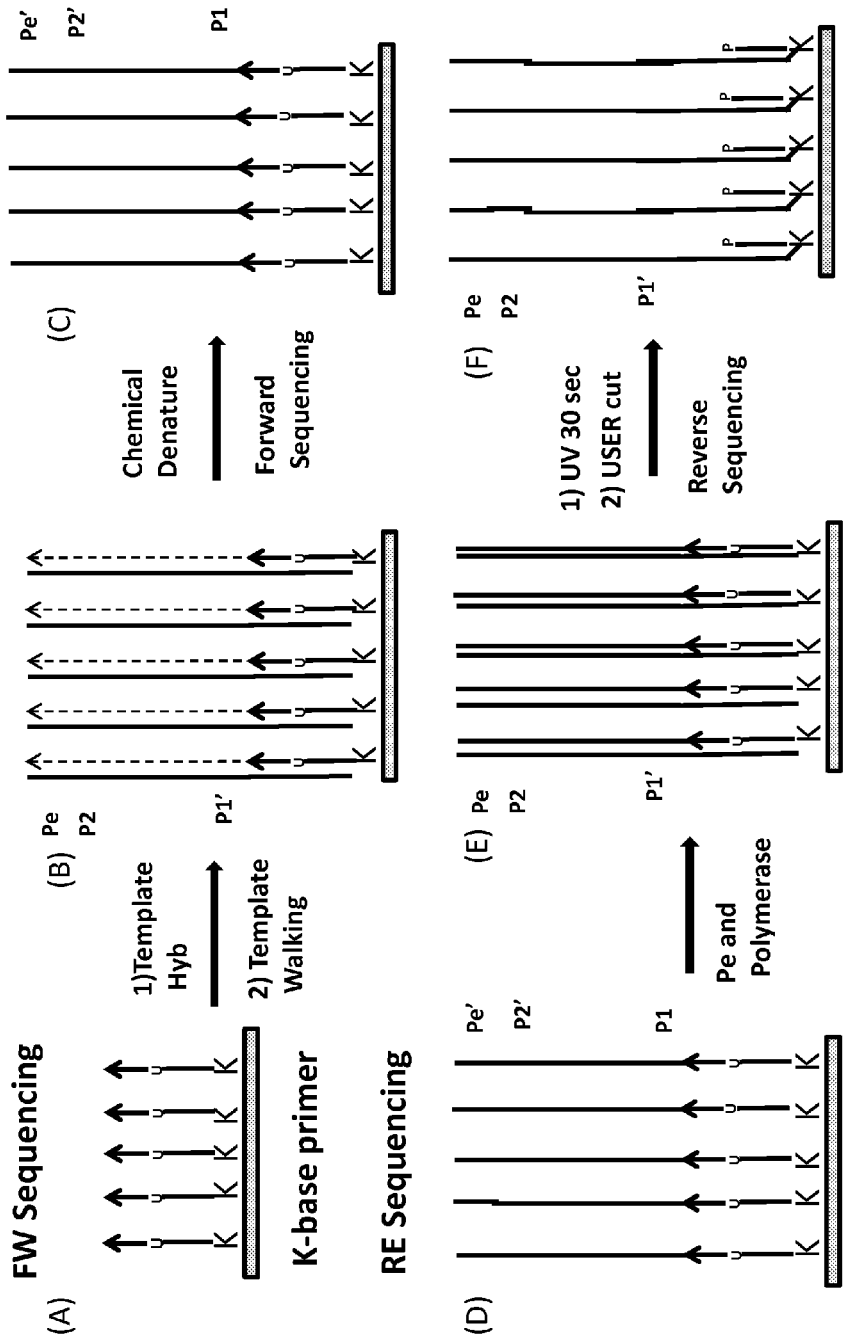
FIG. 9: A non-limiting schematic depiction of a paired end sequencing method.

In some embodiments, a paired end sequencing reaction comprises: (a) a forward sequencing step; (b) a cross-linking step, (c) a cleavage step, and (d) a reverse sequencing step (FIG. 9).

Sequencing Templates

In some embodiments, one or more template polynucleotides can be generated using any method, and then subjected to paired end sequencing. For example, template polynucleotides can be a fragment library construct (U.S. Ser. No.

13/482,542) or a mate pair library construct (U.S. Ser. No. 12/350,837 and International publication No. WO/2012/044847) all of which applications are incorporated by reference herein in their entireties. For example, template polynucleotides (generated using any method) can be denatured using chemical or heat to produce single-stranded template polynucleotides for paired end sequencing. Optionally, any template walking method according to the present teachings (or taught in U.S. Ser. No. 13/328,844, filed Dec. 16, 2011, this application is incorporated by reference herein in its entirety) can be used to generate duplex template polynucleotides (FIGS. 9 A, B and C), and the duplexes can denatured using chemical or heat to produce single-stranded template polynucleotides for paired end sequencing. For convenience sake, the term "template polynucleotides" will be used to describe a nucleic acid generated by any method, to be used for paired end sequencing.

Scissile Moieties

In some embodiments, a template polynucleotide comprises at least one scissile moiety. In some embodiments, a scissile moiety can be cleaved with heat, irradiation, at least one chemical or at least one enzyme. Optionally, a scissile moiety can be incorporated into a template polynucleotide during chemical synthesis or amplification (e.g., PCR) using a nucleoside or nucleotide analog having a scissile moiety. Optionally, a scissile moiety can be incorporated into a template polynucleotide by conducting a primer extension reaction using a primer having a scissile moiety. Optionally, a scissile moiety can be added to a pre-formed template polynucleotide by chemical or enzymatic reaction.

In some embodiments, a scissile moiety can be cleaved with a glycosylase enzyme. A glycosylase optionally has N-glycosylase activity which releases the cleavable nucleotide from double stranded DNA. Optionally, the removal of the cleavable nucleotide generates an abasic, apurinic or apyrimidinic site. The abasic site can optionally be further modified, for example by another enzymatic activity. Optionally, the abasic site is modified by a lyase to generate a base gap. The lyase for example cleaves 3' and/or 5' to the abasic site. Cleavage optionally occurs at both the 5' and 3' end by the lyase, resulting in removing the abasic site and leaving a base gap. Exemplary cleavable moieties (e.g., cleavable nucleotides) include 5-hydroxy-uracil, 7, 8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine can be recognized and removed by various glycosylases to form an apurinic site. One suitable enzyme is formamidopyrimidine [fapy]-DNA glycosylase, also known as 8-oxoguanine DNA glycosylase or FPG. FPG acts both as a N-glycosylase and an AP-lyase. The N-glycosylase activity optionally releases damaged purines from double stranded DNA, generating an apurinic (AP site), where the phosphodiester backbone is optionally intact. The AP-lyase activity cleaves both 3' and 5' to the AP site thereby removing the AP site and leaving a one-base gap. In an example the cleavable nucleotide is 8-oxoadenine, which is converted to a one-base gap by FPG with both glycosylase and lyase activities.

In some embodiments, the template polynucleotide can include at least one uracil base or derivative thereof. In some embodiment, a uracil base can be cleaved with uracil DNA glycosylase. Optionally, a uracil can be cleaved with a USER™ (uracil-specific excision reagent) enzyme system (e.g., from New England Biolabs), which includes a mixture of enzymes including uracil DNA glycosylase (UDG) and a DNA glycosylase-lyase Endonuclease VIII, where UDG catalyses the excision of a uracil base, forming an abasic (apyrimidinic) site while leaving the phosphodiester backbone intact, and where the lyase activity of Endonuclease VIII breaks the phosphodiester backbone at the 3' and 5' sides of the abasic site so that base-free deoxyribose is released. In some embodiments, a kinase can be used to convert the phosphate group on the 3' end of cleaved product to an —OH group. In some embodiments, a template polynucleotide can include other scissile nucleosides, including 5-hydroxy-uracil, 7,8-dihydro-8-oxoguanine (8-oxoguanine), 8-oxoadenine, fapy-guanine, methyl-fapy-guanine, fapy-adenine, aflatoxin B1-fapy-guanine, or 5-hydroxy-cytosine. In some embodiments, a scissile nucleoside can be recognized and removed by various glycosylases to form an apurinic site.

In some embodiments, a 5' or 3' portion of a template polynucleotide comprises an A-rich or T-rich sequence, and may or may not include at least one scissile moiety. For example, a 5' or 3' portion of a template polynucleotide comprises $(A)_N dU(A)_N$, where N is 2-30.

Cross Linking Moieties

In some embodiments, a template polynucleotide comprises at least one cross-linking moiety. In some embodiments, a cross linking moiety can form a covalent bond between two nucleic acids. Optionally, a cross-linking moiety can be located at any position of the template polynucleotide, including at the 5' or 3' end, or internally. Optionally, a cross linking moiety can bond two nucleic acids together at any positions, including bonding together any combination of their 5', 3' and/or internal positions. Optionally, a cross linking moiety can be induced to form a bond by heat, chemical or photochemical conditions. Optionally, the cross link can be reversible or non-reversible. Optionally, a cross linking moiety can be induced to undergo inter-strand or intra-strand cross-linking. Optionally, a cross linking moiety can bond together any type of nucleoside, including a purine or pyrimidine nucleoside, such as for example adenosine, guanosine, cytidine, thymidine, or uridine nucleosides or analogs thereof. Optionally, a cross linking moiety on one nucleic acid can form a bond with another nucleic acid in close proximity. For example, two nucleic acid strands hybridized together to form a duplex are in close proximity with each other to permit linking with a cross linking moiety. Optionally, a cross linking moiety can form a bond between any sugar or base group on two nucleic acids. Optionally, a cross linking moiety can be incorporated into a template polynucleotide during chemical synthesis or amplification (e.g., PCR) using a nucleoside or nucleotide analog having a cross linking moiety. Optionally, a cross linking moiety can be incorporated into a template polynucleotide by conducting a primer extension reaction using a primer having a cross linking moiety. Optionally, a cross linking moiety can be added to a pre-formed template polynucleotide by chemical or enzymatic reaction. Optionally, a cross linking moiety comprises a coumarin (including substitute coumarins), furocoumarin, isocoumarin, bis-coumarin, pyrene, benzodipyrone, psoralen, quinone, $\alpha,\beta$-unsaturated acid, ester, ketone, nitrile, azido, or any derivatives thereof. Optionally, the 5' or 3' end of a template polynucleotide (having at least one cross linking moiety) can be attached to a surface. In FIG. 9, the symbol "K" represents a cross-linking moiety. In some embodiments, a cross linking moiety can be induced to form a bond using any appropriate wavelength of light in a UV-visible-IR spectrum, including about 190-800 nm. In some embodiments, a photo-inducible cross linking moiety can be irradiated for an appropriate amount of time, including about 0.1-10 seconds, or about 0.5-5 seconds, or about 1-2 seconds.

In some embodiments, a template polynucleotide can include one or more cross linking moieties (e.g., nucleoside analogs) that can undergo ultra-fast photo-cross linking. In some embodiments, a cross linking nucleoside comprises a carbazole nucleoside. In some embodiments, a cross linking nucleoside comprises a 3-cyanovinylcarbazole nucleoside (Yoshimura and Fujimoto 2008 Organic Letters 10(15):3227-3230). In some embodiments, in FIG. 9, the symbol "K" represents a 3-cyanovinylcarbazole nucleoside. In some embodiments, a cross linking nucleoside can be photo-irradiated at about 345-375 nm, or about 350-370 nm, or about 355-365 nm. In some embodiments, a photo-cross linking nucleoside can be photo-irradiated at about 366 nm.

Sequencing Platforms

In some embodiments, the sequencing reaction comprises a paired end sequencing reaction using any type of sequencing platform, including any next-generation sequencing platform such as: sequencing by oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeq™, from Illumina), pyrophosphate sequencing (e.g., Genome Sequencer FLX from 454 Life Sciences), single molecule sequencing platforms (e.g., HeliScope™ from Helicos™), and ion-sensitive sequencing (e.g., Personal Genome Machine and Proton from Ion Torrent Systems, Inc.) (U.S. Ser. No. 13/482,542, U.S. Ser. No. 12/350,837, International publication No. WO/2012/044847, U.S. Pat. No. 7,948,015, and U.S. Ser. No. 12/002,781, all of which applications and patents are incorporated by reference herein in their entireties).

Paired End Sequencing

In some embodiments, a paired end sequencing reaction comprises: (a) a forward sequencing step; (b) a cleavage step, and (c) a reverse sequencing step.

In some embodiments, a paired end sequencing reaction comprises: (a) a forward sequencing step; (b) a cross-linking step, (c) a cleavage step, and (d) a reverse sequencing step (FIG. 9).

Forward Sequencing Step

In some embodiments, a forward sequencing steps comprises (i) hybridizing a first primer to a portion of a template polynucleotide, (ii) extending the first primer by conducting primer extension reactions (e.g., polymerase-catalyzed successive nucleotide incorporations), and (iii) identifying the incorporated nucleotides. In some embodiments, in a paired end sequencing reaction, the template polynucleotides can be immobilized to a surface, and comprise a cross linking moiety and a scissile moiety (FIG. 9). In some embodiments, a forward sequencing reaction occurs in a direction towards or away from the surface. FIG. 9E depicts a non-limiting embodiment of a forward sequencing reaction occurring in a direction towards the surface.

In some embodiments, the forward sequencing reaction comprises a polymerase and a plurality of nucleotides. Optionally, the nucleotides can be labeled with a detectable reporter moiety (e.g., a fluorophore) or can be unlabeled. In some embodiments, the primer extension reaction produces a first extension strand. In some embodiments, the primer extension reaction produces a duplex having a template polynucleotide hybridized to a first extension strand. In some embodiments, the template polynucleotide and first extension strand are in close proximity with each other to permit cross linking to two strands together (FIG. 9F). In some embodiments, the primer extension reaction continues beyond the position of the at least one scissile moiety which is located on the template polynucleotide. In some embodiments, the 3' end of the first extension strand overlaps with the position of the at least one scissile moiety which is located on the template polynucleotide.

Cleavage Step

In some embodiments, a cleavage step comprises cleaving the template polynucleotide at the scissile moiety with at least one enzyme. In some embodiments, the scissile moiety can be cleaved with a uracil DNA glycosylase (UDG) and a DNA glycosylase-lyase Endonuclease VIII. For example, a template polynucleotide containing a uracil base can be cleaved with a USER™ enzyme system (New England Biolabs). In some embodiments, cleavage of a template polynucleotide can generate a truncated template polynucleotide having a phosphate group at the end of the cleaved strand. In some embodiments, a kinase can be used to convert the phosphate group on the 3' end of cleaved product to an —OH group. In some embodiments, the newly created 3' OH terminus on the truncated template polynucleotide can be used as an initiation site for a primer extension reaction. Optionally, a portion of a cleaved template polynucleotide can be removed (e.g., denatured) from the duplex so that a portion of the first extension strand is single-stranded (FIG. 9F).

Cross-Linking Step

In some embodiments, a cross-linking step comprises treating the duplex (e.g., template polynucleotide hybridized to a first extension strand) with a compound or with irradiation to induce cross-linking a nucleoside on the template polynucleotide with a nucleoside on the first extension strand (FIG. 9F).

Reverse Sequencing Step

In some embodiments, a reverse sequencing step comprises (i) initiating primer extension from a terminal 3'OH on a truncated template polynucleotide, (ii) extending the 3'OH by conducting primer extension reactions (e.g., polymerase-catalyzed successive nucleotide incorporations), and (iii) identifying the incorporated nucleotides.

In some embodiments, a reverse sequencing step comprises (i) hybridizing a second primer to a portion of a first extension strand, (ii) extending the first primer by conducting primer extension reactions (e.g., polymerase-catalyzed successive nucleotide incorporations), and (iii) identifying the incorporated nucleotides.

In some embodiments, a reverse sequencing reaction occurs in a direction away from or towards the surface. FIG. 9E depicts a non-limiting embodiment of a forward sequencing reaction occurring in a direction away from the surface. In some embodiments, the forward sequencing reaction comprises a polymerase and a plurality of nucleotides. Optionally, the nucleotides can be labeled with a detectable reporter moiety (e.g., a fluorophore) or can be unlabeled. In some embodiments, the primer extension reaction produces a second extension strand. In some embodiments, a reverse sequencing step produces a duplex having a first extension strand hybridized to a second extension strand and cross-linked together. In some embodiments, the reverse sequencing reaction comprises a polymerase and a plurality of nucleotides. Optionally, the nucleotides can be labeled with a detectable reporter moiety (e.g., a fluorophore) or can be unlabeled.

Embodiments

In some embodiments, a paired end sequencing reaction comprises: (a) conducting a forward sequencing reaction on a template polynucleotide attached to a surface and having at least one cleavable scissile moiety by (i) hybridizing a first primer to the template polynucleotide, (ii) extending the first primer by conducting primer extension reactions (e.g., polymerase-catalyzed successive nucleotide incorporations) and forming a first extension strand hybridized to the template polynucleotide, and (iii) identifying the incorporated nucleotides in the first extension strand; (b) cleaving the template polynucleotide by reacting the scissile moiety with heat, irradiation, at least one chemical, or at least one enzyme, to form a truncated template polynucleotide and optionally forming a terminal 3' phosphate group, and optionally converting the terminal 3' phosphate group to an —OH group, and optionally removing a portion of the cleaved template polynucleotide; and (c) conducting a reverse sequencing reaction on the first extension strand (now cross linked to the truncated template polynucleotide) by extending the terminal 3' OH group on the truncated template polynucleotide with primer extension reactions (e.g., polymerase-catalyzed successive nucleotide incorporations) and forming a second extension strand, and (iii) identifying the incorporated nucleotides in the second extension strand.

In some embodiments, a paired end sequencing reaction comprises: (a) conducting a forward sequencing reaction on a template polynucleotide attached to a surface (e.g., immobilized at its 5' end) and having at least one enzymatically cleavable scissile moiety (e.g., uracil base) by (i) hybridizing a first primer to the template polynucleotide, (ii) extending the first primer by conducting primer extension reactions (e.g., polymerase-catalyzed successive nucleotide incorporations in a direction towards the surface) and forming a first extension strand hybridized to the template polynucleotide, and (iii) identifying the incorporated nucleotides in the first extension strand; (b) cleaving the template polynucleotide by reacting the scissile moiety with at least one enzyme (e.g., glycosylase and a lyase) to form a truncated template polynucleotide and forming a terminal 3' phosphate group, and optionally converting the terminal 3' phosphate group to an —OH group (e.g., with a kinase), and optionally removing a portion of the cleaved template polynucleotide (e.g., by denaturation); and (c) conducting a reverse sequencing reaction on the first extension strand (now cross linked to the truncated template polynucleotide) by extending the terminal 3' OH group on the truncated template polynucleotide with primer extension reactions (e.g., polymerase-catalyzed successive nucleotide incorporations in a direction away from the surface) and forming a second extension strand, and (iii) identifying the incorporated nucleotides in the second extension strand.

In some embodiments, a paired end sequencing reaction comprises: (a) conducting a forward sequencing reaction on a template polynucleotide attached to a surface and having at least one cleavable scissile moiety by (i) hybridizing a first primer to the template polynucleotide, (ii) extending the first primer by conducting primer extension reactions (e.g., polymerase-catalyzed successive nucleotide incorporations) and forming a first extension strand hybridized to the template polynucleotide, and (iii) identifying the incorporated nucleotides in the first extension strand; (b) cleaving the template polynucleotide by reacting the scissile moiety with heat, irradiation, at least one chemical, or at least one enzyme, to form a truncated template polynucleotide and optionally forming a terminal 3' phosphate group, and optionally converting the terminal 3' phosphate group to an —OH group, and optionally removing a portion of the cleaved template polynucleotide; and (c) conducting a reverse sequencing reaction on the first extension strand (now cross linked to the truncated template polynucleotide) by conducting a reverse sequencing reaction on the first extension strand (now cross linked to the truncated template polynucleotide) by (i) hybridizing a second primer to the first extension strand, (ii) extending the second primer by conducting primer extension reactions (e.g., polymerase-catalyzed successive nucleotide incorporations) and forming a second extension strand hybridized to the template polynucleotide, and (iii) identifying the incorporated nucleotides in the second extension strand.

In some embodiments, a paired end sequencing reaction comprises: (a) conducting a forward sequencing reaction on a template polynucleotide attached to a surface (e.g., immobilized at its 5' end) and having at least one enzymatically cleavable scissile moiety (e.g., uracil base) by (i) hybridizing a first primer to the template polynucleotide, (ii) extending the first primer by conducting primer extension reactions (e.g., polymerase-catalyzed successive nucleotide incorporations in a direction towards the surface) and forming a first extension strand hybridized to the template polynucleotide, and (iii) identifying the incorporated nucleotides in the first extension strand; (b) cleaving the template polynucleotide by reacting the scissile moiety with at least one enzyme (e.g., glycosylase and a lyase) to form a truncated template polynucleotide and forming a terminal 3' phosphate group, and optionally converting the terminal 3' phosphate group to an —OH group (e.g., with a kinase), and optionally removing a portion of the cleaved template polynucleotide (e.g., by denaturation); and (c) conducting a reverse sequencing reaction on the first extension strand (now cross linked to the truncated template polynucleotide) by (i) hybridizing a second primer to the first extension strand, (ii) extending the second primer by conducting primer extension reactions (e.g., polymerase-catalyzed successive nucleotide incorporations in a direction away from the surface) and forming a second extension strand hybridized to the template polynucleotide, and (iii) identifying the incorporated nucleotides in the second extension strand.

In some embodiments, a paired end sequencing reaction comprises: (a) conducting a forward sequencing reaction on a template polynucleotide attached to a surface and having at least one cross linking moiety and at least one cleavable scissile moiety by (i) hybridizing a first primer to the template polynucleotide, (ii) extending the first primer by conducting primer extension reactions (e.g., polymerase-catalyzed successive nucleotide incorporations) and forming a first extension strand hybridized to the template polynucleotide, and (iii) identifying the incorporated nucleotides in the first extension strand; (b) inducing cross linking between the template polynucleotide and the first extension strand with a heat, chemical or photochemical condition; (c) cleaving the template polynucleotide by reacting the scissile moiety with heat, irradiation, at least one chemical, or at least one enzyme, to form a truncated template polynucleotide and optionally forming a terminal 3' phosphate group, and optionally converting the terminal 3' phosphate group to an —OH group, and optionally removing a portion of the cleaved template polynucleotide; and (d) conducting a reverse sequencing reaction on the first extension strand (now cross linked to the truncated template polynucleotide) by extending the terminal 3' OH group on the truncated template polynucleotide with primer extension reactions (e.g., polymerase-catalyzed successive nucleotide incorporations) and forming a second extension strand, and (iii) identifying the incorporated nucleotides in the second extension strand.

In some embodiments, a paired end sequencing reaction comprises: (a) conducting a forward sequencing reaction on a template polynucleotide attached to a surface (e.g., immobilized at its 5' end) and having at least one photo cross linking moiety (e.g., 3-cyanovinylcarbazole nucleoside) and at least one enzymatically cleavable scissile moiety (e.g., uracil base) by (i) hybridizing a first primer to the template polynucleotide, (ii) extending the first primer by conducting primer extension reactions (e.g., polymerase-catalyzed successive nucleotide incorporations in a direction towards the surface) and forming a first extension strand hybridized to the template polynucleotide, and (iii) identifying the incorporated nucleotides in the first extension strand; (b) cross linking the template polynucleotide to the first extension strand by irradiating the cross linking moiety with an appropriate wavelength of light (e.g., 366 nm); (c) cleaving the template polynucleotide by reacting the scissile moiety with at least one enzyme (e.g., glycosylase and a lyase) to form a truncated template polynucleotide and forming a terminal 3' phosphate group, and optionally converting the terminal 3' phosphate group to an —OH group (e.g., with a kinase), and optionally removing a portion of the cleaved template polynucleotide (e.g., by denaturation); and (d) conducting a reverse sequencing reaction on the first extension strand (now cross linked to the truncated template polynucleotide) by extending the terminal 3' OH group on the truncated template polynucleotide with primer extension reactions (e.g., polymerase-catalyzed successive nucleotide incorporations in a direction away from the surface) and forming a second extension strand, and (iii) identifying the incorporated nucleotides in the second extension strand.

In some embodiments, a paired end sequencing reaction comprises: (a) conducting a forward sequencing reaction on a template polynucleotide attached to a surface and having at least one cross linking moiety and at least one cleavable scissile moiety by (i) hybridizing a first primer to the template polynucleotide, (ii) extending the first primer by conducting primer extension reactions (e.g., polymerase-catalyzed successive nucleotide incorporations) and forming a first extension strand hybridized to the template polynucleotide, and (iii) identifying the incorporated nucleotides in the first extension strand; (b) inducing cross linking between the template polynucleotide and the first extension strand with a heat, chemical or photochemical condition; (c) cleaving the template polynucleotide by reacting the scissile moiety with heat, irradiation, at least one chemical, or at least one enzyme, to form a truncated template polynucleotide and optionally forming a terminal 3' phosphate group, and optionally converting the terminal 3' phosphate group to an —OH group, and optionally removing a portion of the cleaved template polynucleotide; and (d) conducting a reverse sequencing reaction on the first extension strand (now cross linked to the truncated template polynucleotide) by conducting a reverse sequencing reaction on the first extension strand (now cross linked to the truncated template polynucleotide) by (i) hybridizing a second primer to the first extension strand, (ii) extending the second primer by conducting primer extension reactions (e.g., polymerase-catalyzed successive nucleotide incorporations) and forming a second extension strand hybridized to the template polynucleotide, and (iii) identifying the incorporated nucleotides in the second extension strand.

In some embodiments, a paired end sequencing reaction comprises: (a) conducting a forward sequencing reaction on a template polynucleotide attached to a surface (e.g., immobilized at its 5' end) and having at least one photo cross linking moiety (e.g., 3-cyanovinylcarbazole nucleoside) and at least one enzymatically cleavable scissile moiety (e.g., uracil base) by (i) hybridizing a first primer to the template polynucleotide, (ii) extending the first primer by conducting primer extension reactions (e.g., polymerase-catalyzed successive nucleotide incorporations in a direction towards the surface) and forming a first extension strand hybridized to the template polynucleotide, and (iii) identifying the incorporated nucleotides in the first extension strand; (b) cross linking the template polynucleotide to the first extension strand by irradiating the cross linking moiety with an appropriate wavelength of light (e.g., 366 nm); (c) cleaving the template polynucleotide by reacting the scissile moiety with at least one enzyme (e.g., glycosylase and a lyase) to form a truncated template polynucleotide and forming a terminal 3' phosphate group, and optionally converting the terminal 3' phosphate group to an —OH group (e.g., with a kinase), and optionally removing a portion of the cleaved template polynucleotide (e.g., by denaturation); and (d) conducting a reverse sequencing reaction on the first extension strand (now cross linked to the truncated template polynucleotide) by (i) hybridizing a second primer to the first extension strand, (ii) extending the second primer by conducting primer extension reactions (e.g., polymerase-catalyzed successive nucleotide incorporations in a direction away from the surface) and forming a second extension strand hybridized to the template polynucleotide, and (iii) identifying the incorporated nucleotides in the second extension strand.

In some embodiments, a first extension strand can be generated according any paired end sequencing reaction of the present teachings. Optionally, the first extension strand can be hybridized to the template polynucleotide and can be generated according any paired end sequencing reaction of the present teachings. Optionally, the first extension strand can be cross-linked to the template polynucleotide and can be generated according any paired end sequencing reaction of the present teachings.

In some embodiments, the second extension strand can be generated according any paired end sequencing reaction of the present teachings. Optionally, the second extension strand can be hybridized to the template polynucleotide and can be generated according any paired end sequencing reaction of the present teachings. Optionally, the second extension strand can be cross-linked to the template polynucleotide and can be generated according to any paired end sequencing reaction of the present teachings.

Compositions and Systems

In some embodiments, the present teachings provide compositions and systems comprising a template polynucleotide attached to a surface and having at least one cleavable scissile moiety. In some embodiments, compositions and systems comprise a template polynucleotide attached to a surface and having at least one cleavable scissile moiety, where the template polynucleotide is hybridized to a first extension strand. In some embodiments, compositions and systems comprise a second extension product which includes a truncated template polynucleotide attached to a surface, where the truncated template polynucleotide is hybridized to a first primer extension strand.

In some embodiments, the present teachings provide compositions and systems comprising a template polynucleotide attached to a surface and having at least one cross linking moiety and at least one cleavable scissile moiety. In some embodiments, compositions and systems comprise a template polynucleotide attached to a surface and having at least one cross linking moiety and at least one cleavable scissile moiety, where the template polynucleotide is hybridized to a first extension strand. In some embodiments, compositions and systems comprise a truncated template polynucleotide attached to a surface and having at least one cross linking moiety, where the truncated template polynucleotide is cross linked to a first primer extension strand. In some embodiments, compositions and systems comprise a second extension product which includes a truncated template polynucleotide attached to a surface and having at least one cross linking moiety, where the truncated template polynucleotide is cross linked to a first primer extension strand.

The following examples are provided purely for illustrative purposes and are not intended to limit the scope of the present disclosure or claims.

EXAMPLES

Example 1

5'-dual-biotin labeled oligo(dT)35 (SEQ ID NO:9) were bound to DynaBeads MyOne streptavidin C1 magnetic beads. 80 million oligo(dT)$_{35}$-bound beads ("(dT)35" disclosed as SEQ ID NO:9) and 800 ul DNA template at 0.01 pg/ul were mixed in hybridization buffer. The DNA template sequence was as follows:
TTTTTTTTTTTTTTTTTTTT CCACTACGCCTC-CGCTTTC CTC TCT ATG GGC AGT CGG TGA TTC GTG GAA GAC GGG GGC AGT CTA TAC CCC TGT GGC GAC CAC TGC GCG GTG GTT TGC TAG GAG AGA ATG AGG AAC CCG GGG CAG (SEQ ID NO:10). The following amplification protocol was performed to hybridize the DNA templates to the beads: 95° C. 2 min, 50° C. 1 min, 40° C. 1 min, 30° C. 1 min, 25° C. 2 min. Beads were washed with washing buffer and the primer was extended with Exo-Klenow by adding to the washed beads 10×NEB buffer2 (40 ul), 25 mM dNTP, 4 ul, Exo-Klenow 40 u/ul, 4 ul, and water, 352 ul, and incubating at room temperature for 10 minutes. The beads were washed again and a template-walking reaction was performed as follows. First, the following reaction mixture was prepared:

5 million beads
10× ThermoPol buffer 10 ul
25 mM dNTP 1 ul
P2 primer (CTG CCC CGG GTT CCT CAT TCT) (SEQ ID NO:11) 50 uM 2 ul
100×BSA 10 ul
Bst DNA polymerase large fragment 8 u/ul 10 ul
H2O 67 ul This reaction mix was incubated at 60° C. for 45 minutes and 90 minutes with shaking. Beads were washed and the amplified DNA on the beads quantified with TaqMan qPCR, using the following reactants:

```
TaqMan forward primer:
                                    (SEQ ID NO: 12)
AGTCGGTGATTCGTGGAAGAC TaqMan reverse primer:
                                    (SEQ ID NO: 13)
CTCATTCTCTCCTAGCAAACCAC
```

```
TaqMan probe:
                                    (SEQ ID NO: 14)
Fam-CCCCTGTGGCGACCAC-NFQ
```

The fold of amplification before and after the template walking reaction was calculated and plotted against reaction time. Sufficient amplification for detection purposes was seen by 30 minutes or less.

Example 2

Binding of template to bead was done as described in Example 1, using the following template: TTTTTTTTTTTTTTTTTTTT CCACTACGCCTC-CGCTTTC CTC TCT ATG GGC AGT CGG TGA TTC GTG GAA GAC GGG GGC AGT CTA TAC CCC TGT GGC GAC CAC TGC GCG GTG GTT TGC TAG GAG AGA ATG AGG AAC CCG GGG CAG (SEQ ID NO:10).

A template-walking reaction was performed as described in Example 1, except that 5 ul of 1 uM P2 primer (CTG CCC CGG GTT CCT CAT TCT) (SEQ ID NO:11) and 5 ul of 8 u/ul Bst DNA polymerase large fragment was added to the reaction, and the beads were incubated at a range of temperatures—specifically, 46° C., 51° C., 58° C., 60° C., 63° C., 65° C. for 45 minutes with shaking.

The DNA templates on the beads with TaqMan qPCR as described in Example 1, using the following reagents:

```
TaqMan forward primer:
                                    (SEQ ID NO: 12)
AGTCGGTGATTCGTGGAAGAC TaqMan reverse primer:
                                    (SEQ ID NO: 13)
CTCATTCTCTCCTAGCAAACCAC TaqMan probe:
                                    (SEQ ID NO: 14)
Fam-CCCCTGTGGCGACCAC-NFQ
```

Figure 5:
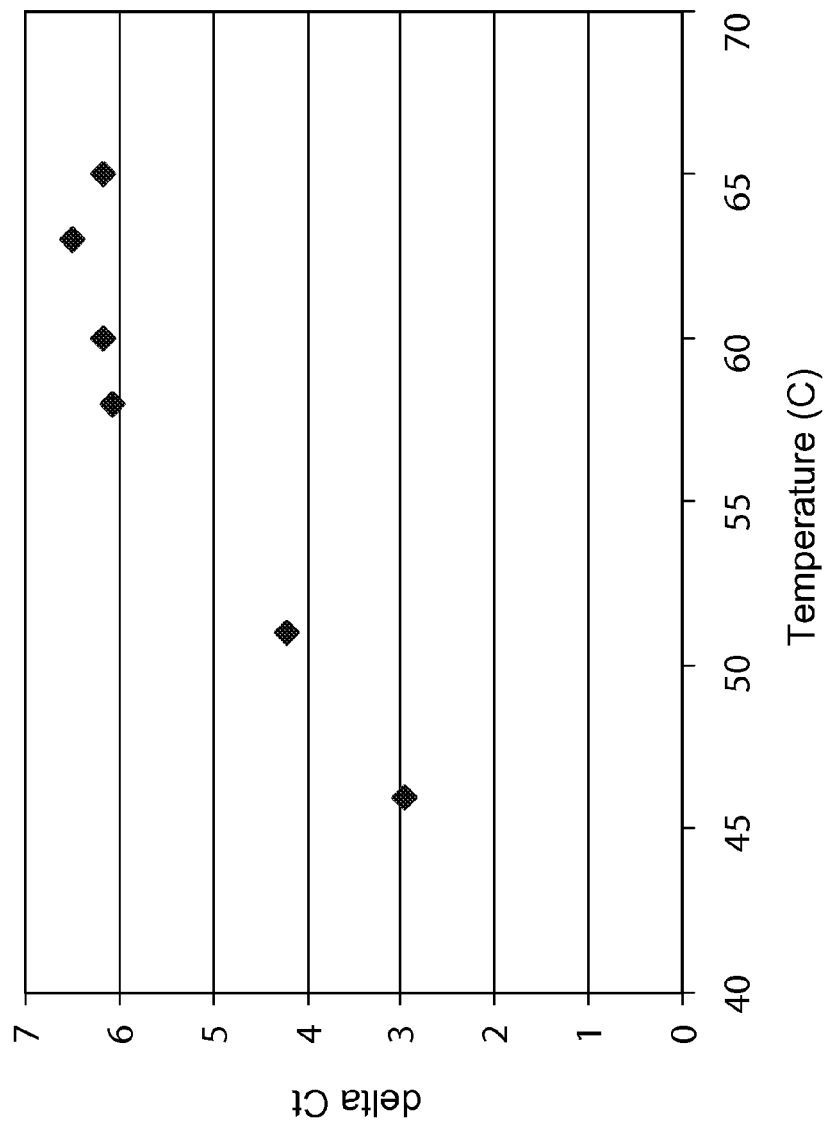
FIG. 5: Influence of temperature on the template walking reaction. A graphical plot of the delta Ct before and after the template walking amplification was calculated and plotted against reaction temperature.

The delta Ct before and after the template walking reaction was calculated and plotted against reaction temperature, as shown in FIG. 5. This figure shows the influence of temperature on the template walking reaction.

Example 3

Oligo(dT)35 (SEQ ID NO:9) beads were prepared as in Example 1, and 80 million oligo(dT)$_{35}$-bound beads ("(dT)$_{35}$" disclosed as (SEQ ID NO:9) were incubated with 800 ul of a mixture of two DNA templates (at equal molar ratio) at 0.04 pg/ul in hybridization buffer. The DNA template sequence is as following.

```
DNA template 1:
                                    (SEQ ID NO: 10)
TTTTTTTTTTTTTTTTTTTT CCACTACGCCTCCGCTTTC CTC TCT ATG GGC

AGT CGG TGA TTC GTG GAA GAC GGG GGC AGT CTA TAC CCC TGT GGC GAC CAC

TGC GCG GTG GTT TGC TAG GAG AGA ATG AGG AAC CCG GGG CAG.

DNA template 2:
                                    (SEQ ID NO: 15)
TTTTTTTTTTTTTTTTTTTTTCCACTACGCCTCCGCTTTCCTCTCTATGGGCAG

TCGGTGATGAAACAGTTGATCATGGACAACCATATTCTGCTGTACGGCCAAGGCGG

ATGTACGGTACAGCAGATACTAAGATGATGAAGAGAATGAGGAACCCGGGGCAG.
```

Binding of template to beads and template-walking was performed as described in Example 1, except that 20 ul of 8 u/ul Bst DNA polymerase large fragment was added, and beads were incubated at 60° C. for 45 minutes with shaking. The beads were washed and diluted in a 96-well qPCR plate to approximately 5 beads per well. 96 duplex TaqMan qPCR reactions were performed with the following primers and probes.

```
TaqMan forward primer1:
                            (SEQ ID NO: 12)
AGTCGGTGATTCGTGGAAGAC.

TaqMan reverse primer1:
                            (SEQ ID NO: 13)
CTCATTCTCTCCTAGCAAACCAC.

TaqMan probe1:
                            (SEQ ID NO: 14)
Vic-CCCCTGTGGCGACCAC-NFQ.

TaqMan forward primer2:
                            (SEQ ID NO: 16)
GAAACAGTTGATCATGGACAACCAT.

TaqMan reverse primer2:
                            (SEQ ID NO: 17)
TCATCTTAGTATCTGCTGTACCGTACAT.

TaqMan probe2:
                            (SEQ ID NO: 18)
Fam-CCGCCTTGGCCGTACAG-NFQ.
```

FIG. 6 shows the Ct values of the 96 duplex TaqMan qPCR reactions.

The following Table 1 summarizes the Ct values. The experimental percentages of beads populations are consistent with calculated probabilities based on monoclonal amplification model and Poison distribution.

TABLE 1

| 96 wells 100 copies cut off | Positive counts | percentages (%) | Probability (%) |
|---|---|---|---|
| FAM Ct < 37 | 7.00 | | |
| Vic Ct < 34 | 8.00 | | |
| FAM Ct < 37 and Vic Ct < 34 | 1.00 | | |
| empty wells or beads | 81.00 | 84.38 | 84.98 |
| single template beads | 14.00 | 14.58 | 14.41 |
| FAM and Vic | 1.00 | 1.04 | 0.61 |

Example 4

Beads were prepared as in Example 1, except 5'-dual-biotin labeled oligo(dA)35 was used instead of Oligo(dT)35 (SEQ ID NO:9) as the bead-immobilized primer.

The following DNA template was bound to the prepared beads as described in

Example 1

The primer was not extended with Exo Klenow. Template walking was performed as in Example 1 except that 20 ul of 120 u/ul Bst DNA polymerase large fragment was added and the beads incubated at 37 C for 3 minutes and then at 60 C for 45 minutes and 90 minutes with shaking. The amplified DNA on the beads were quantified using TaqMan qPCR and the following reagents:

```
TaqMan forward primer:
                            (SEQ ID NO: 12)
AGTCGGTGATTCGTGGAAGAC TaqMan reverse primer:
                            (SEQ ID NO: 13)
CTCATTCTCTCCTAGCAAACCAC TaqMan probe:
                            (SEQ ID NO: 14)
Fam-CCCCTGTGGCGACCAC-NFQ
```

Figure 7:
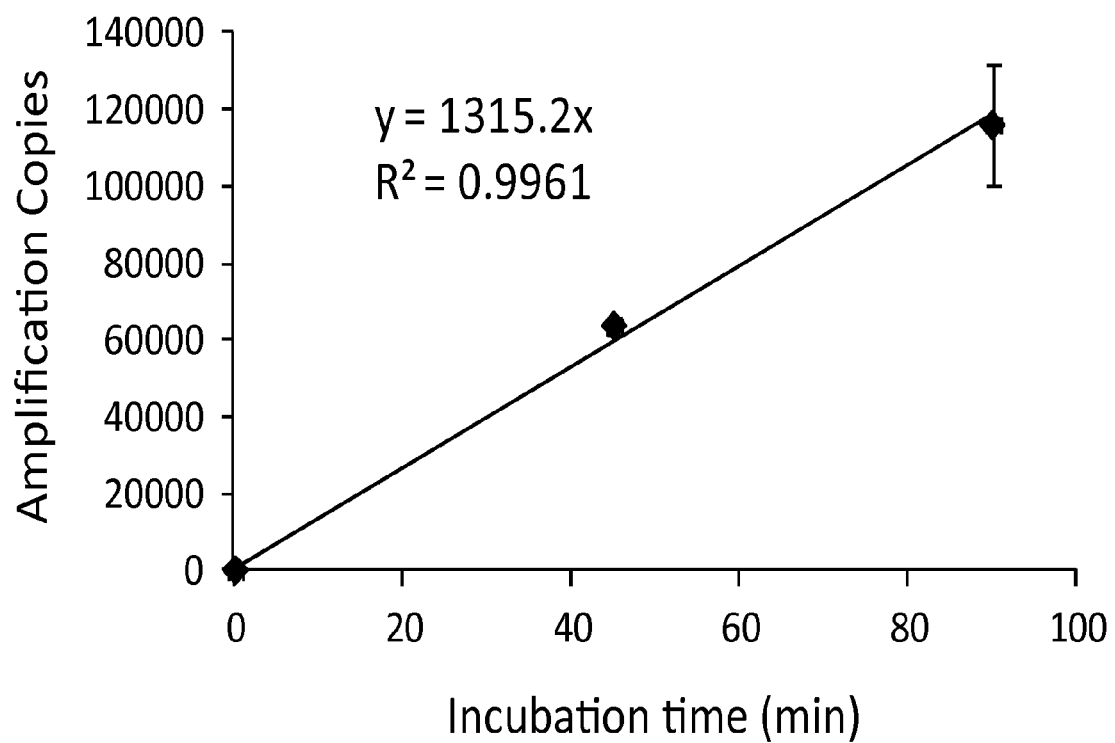
FIG. 7: 100,000-fold amplification by template walking on beads. Delta Ct before and after the template walking reaction and fold of amplification before and after the template walking reaction was calculated and plotted against reaction time.

The fold of amplification before and after the template walking reaction was calculated and plotted against reaction time, as shown in FIG. 7. After 90 minutes of template walking reaction, the DNA templates on beads were amplified about 100,000 fold.

Example 5

5'-dual-biotin labeled oligo(dA)35 (SEQ ID NO:19) were bound to DynaBeads MyOne streptavidin C1 magnetic beads. 80 million oligo(dA)35-bound beads ("(dA)35" disclosed as (SEQ ID NO:19) were mixed with 800 ul E coli DH10B genomic DNA fragment library at 0.1 pg/ul in hybridization buffer. Hybridization buffer was used as a negative control. The DH10B fragment library had the following structure.

AAAAAAAAAAAAAAAAAAAA (SEQ ID NO:21)—P1 adaptor—150 bp to 200 bp DH10B genomic DNA fragments—P2 adaptor The following program was run on a thermo cycler to hybridize the DNA templates to the beads: 95 C 2 min, 50 C 1 min, 40 C 1 min, 30 C 1 min, 25 C 2 min. The beads were washed and a template walking reaction was done as follows:

5 million beads with DH10B library hybridized, or negative control beads
10× ThermoPol buffer 10 ul
25 mM dNTP 1 ul
P2 primer (CTG CCC CGG GTT CCT CAT TCT) (SEQ ID NO:11) 50 uM 2 ul
100×BSA 10 ul
Bst DNA polymerase large fragment 120 u/ul 10 ul
H2O 67 ul The beads were incubated at 37 C for 3 minutes and then at 60 C for 45 minutes with shaking. The beads were then washed and stained with fluorescent label by hybridizing a cy5 labeled oligonucleotide targeting the P1 adaptor sequence in the DH10B fragment library. The stained beads were laid on a microscope slide and imaged on a fluorescent microscope.

(SEQ ID NO: 20)
AAAAAAAAAAAAAAAAAAAA CCACTACGCCTCCGCTTTC CTC TCT ATG

GGC AGT CGG TGA TTC GTG GAA GAC GGG GGC AGT CTA TAC CCC TGT GGC

GAC CAC TGC GCG GTG GTT TGC TAG GAG AGA ATG AGG AAC CCG GGG CAG.

A shifted overlay of the white light image of the beads and the cy5 fluorescent image of the beads revealed the white light images of the beads as black dots and the cy5-labeled beads as red dots. About 15% of the beads were seen to be positively stained with cy5 and the rest were negative.

Another exemplary protocol for template walking was performed as follows:

Hybridization and primer extension: template was diluted in 1×NEB Buffer 2 to a final concentration of 100 pM. Template was heated at 95° C. for 3 min and then keep on ice. Hybridization/reaction mixes were prepared as follows:

| 100 pM denatured template: | 48.5 µl |
| 100 mM dNTP: | 0.5 µl |
| 5 U/µl Klenow: | 1 µl |
| Total volume: | 50 µl |

10 µl of reaction mixture was added to chosen lanes of StarLight flow cell and the flow cell at 37° C. for 20 minutes. Each lane was washed twice with 1 ml 1×TMAX buffer Template walking: A walking reaction mixture was prepared was follows:

| 10× NEB ThermoPol Buffer: | 5 µl |
| 100 mM dNTP: | 1 µl |
| 50 µM Primer Pe: | 0.5 µl |
| 120 U/µl Bst (from NEB): | 20 µl |
| H$_2$O: | 23.5 µl |
| Total volume: | 50 µl |

10 µl of reaction mixture was added to each lane, and the flow cell incubated at 60° C. for 20 minutes. Each lane was washed twice with 1 ml 1×TMAX buffer, and the nucleic acid subjected to analysis as desired.

Example 6

Figure 3:
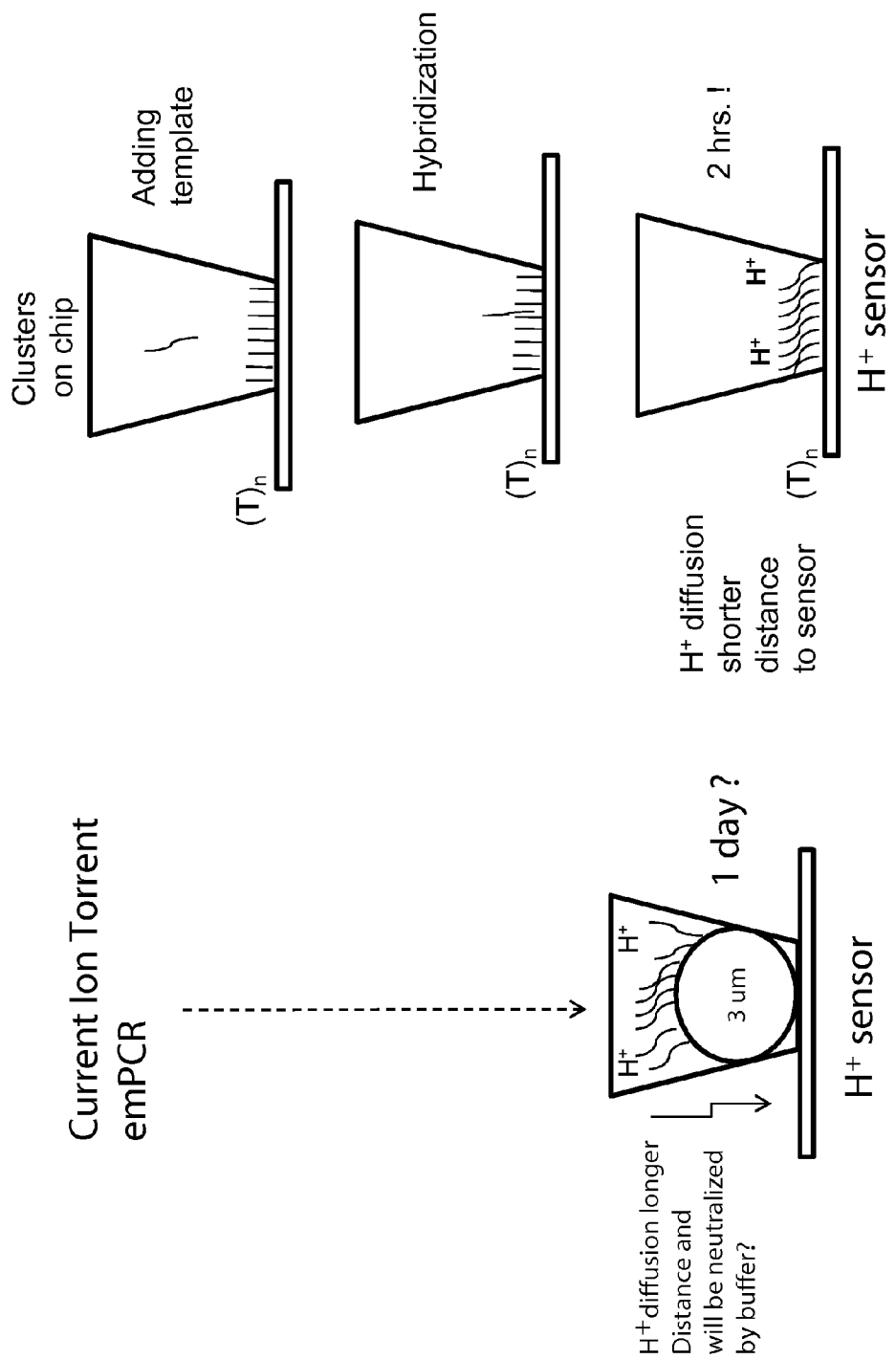
FIG. 3: Alternative embodiments using semiconductor-based detection of sequencing by synthesis. Template walking can be used to generate a population of clonal amplicons on a bead or on the base or bottom of a reaction chamber. In an alternative embodiment, the immobilized primer comprises an adenosine-rich sequence designated as $(A)_n$, e.g., $(A)_{30}$ (SEQ ID NO:1), and the primer binding site for the immobilized primer on the template comprises a complementary T-rich sequence, e.g., $(T)_{30}$ (SEQ ID NO:2).
Figure 4:
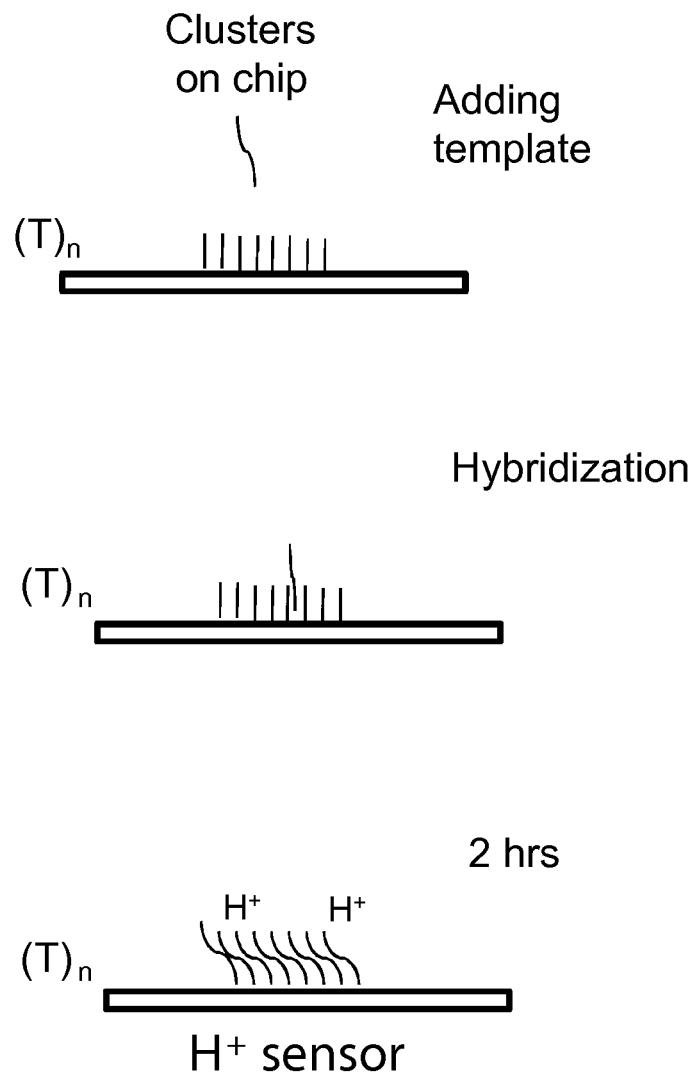
FIG. 4: Alternative embodiments of immobilization sites in the form of primer lawns on planar substrates. Arrays of separated immobilization sites can be used or else a single continuous lawn of primers can be considered to be a random array of immobilization sites. Optionally, the location of one or more immobilization sites in the continuous lawn of primers can be undetermined as yet, where the location is determined at the time of attachment of the initial template before walking or is determined by the space occupied by the amplified cluster. In an alternative embodiment, the immobilized primer comprises an adenosine-rich sequence designated as $(A)_n$, e.g., $(A)_{30}$ (SEQ ID NO:1), and the primer binding site for the immobilized primer on the template comprises a complementary T-rich sequence, e.g., $(T)_{30}$ (SEQ ID NO:2).

This example describes clonal amplification of nucleic acids onto supports in the form of matrices, followed by sequencing of the resulting amplified population using the Ion Torrent PGM™ sequencer, which is an ion-based sequencing system that detects byproducts of nucleotide incorporation using a chemically sensitive field effect transistor (chemFET). Exemplary embodiments are shown in FIG. 3. In an embodiment, at least one primer for template walking is immobilized on a surface (e.g., the floor) of individual wells, where an individual well is operatively connected to a corresponding transistor.

Template Preparation:

Libraries were prepared as described in the Life Technologies SOLiD 4.0 User Manual. Briefly, 2 ug of genomic DNA isolated from the *E. coli* strain DH10B was sheared using a Covaris S2 system. The sheared DNA was end-repaired and was purified with the SOLiD Library Column Purification Kit.

A double-stranded adapter ("ION Adaptor 1") was prepared by hybridizing the single-stranded complementary oligonucleotides ION Adaptor Oligo 1 and ION Adaptor Oligo 1' to each other according to the procedure in Appendix C of the User Manual for the SOLiD™ 4 System (Applied Biosystems, Life Technologies). ION Adaptor Oligo 1 included a priming sequence that was 30 mer long (i.e., was 30 nucleotides in length) and ION Adaptor Oligo 1' included the complement of this 30mer priming sequence at the 5' end, plus an additional two thymidine residues ("TT") at the 3' end. Hybridization of ION Adaptor Oligo 1 with ION Adaptor Oligo 1' forms the double-stranded adaptor "Ion Adaptor 1", which includes a 30-mer double-stranded priming sequence and has one blunt end and one "sticky" end including a 3' overhang of two additional T residues. A third primer, Ion Adapter A PCR primer, which contained only the first 20 nucleotides of ION Adaptor Oligo 1, was used in the PCR step as described below.

Similarly, a second double-stranded adaptor ("ION Adaptor 2") was prepared by hybridizing the complementary single-stranded oligonucleotides Ion T-Tailed Adapter Oligo 2 and Ion A-Tailed Adapter Oligo 2' using the procedure in Appendix C of the SOLiD 4.0 User Manual. ION T-tailed Adaptor Oligo 2 was 52mer in length and included a priming sequence of 30 nucleotides to the 5' end, followed by a stretch of 22 thymidine ("T") residues (SEQ ID NO:22) at the 3' end. ION A-tailed Adaptor Oligo 2' was 50mer in length and included a stretch of 20 adenine ("A") residues (SEQ ID NO:21) at the 5' end, followed by a 30-nucleotide stretch complementary to the priming sequence of ION T-tailed Adaptor Oligo 2. Hybridization of the ION T-tailed Adaptor Oligo 2 with the ION A-tailed Adaptor Oligo 2' forms the double-stranded adaptor "Ion Adaptor 2", which includes a 30mer double stranded priming sequence flanking a 20mer poly-A/poly-T duplex (SEQ ID NOS:21 and 3, respectively), and has one blunt end and one "sticky" end including a 3' overhang of two additional T residues.

The double-stranded adaptors Ion Adaptor 1 and Ion Adaptor 2 were ligated to the end-repaired DNA. The ligation product was size-selected and subjected to 8 cycles of amplification using the following primers: Ion Adapter A PCR primer (which contained only the first 20 nucleotides of ION Adaptor Oligo 1) and ION T-tailed Adapter Oligo 2. The amplified reaction product was subjected to size selection, yielding a final adapted double-stranded DNA library with a median size of 209 bp.

Isothermal Amplification of Nucleic Acids:

The adapted double-stranded library obtained as described above was mixed with polymer matrices including 30mer polyA primers (SEQ ID NO:1) (these matrices are referred to herein as "SNAPPs" for Scaffolded Nucleic Acid Polymer Particles, and were prepared essentially as described in U.S. Patent Publication No. 20100304982, Hinz et al.).

Annealing Templates to Particles:

The double-stranded library was annealed to the SNAPP particles. Briefly, 10 million SNAPPs were washed 2× in buffer (each wash carried out by pipetting up and down to resuspend the SNAPPs, then pelleting the SNAPPs by centrifugation)

The dsDNA adapter-ligated and size-selected library was diluted in buffer, such that the library was added at an average ratio of 1 double-stranded template molecule per SNAPP, in a total volume of 100 ul.

The template library was hybridized to the SNAPPs by running the following thermocycling program:

95° C. for 3 minutes

50° C. for 1 minute

40° C. for 1 minute

30° C. for 1 minute

25° C. for 2 minutes

The template-annealed SNAPPs were washed twice in buffer.

Isothermal Templating Reaction and Processing:

The annealed and washed SNAPPs were resuspended in the following amplification reaction mixture:

1×Phi29 DNA Polymerase Reaction Buffer, 0.1 mg/mL BSA, 1 uM ION Adaptor A PCR primer, 1 mM equimolar dNTP mix and 100 U Phi29 enzyme (NEB #MO269L)

The amplification reaction mixture including the SNAPPs were then incubated in a thermomixer with 1000 RPM shaking as follows:

30° C. for 6 hours
65° C. for 30 minutes

The SNAPPS were pelleted and washed 2× in Life TEX Buffer

The double-stranded amplified DNA on the SNAPPs was then denatured to remove complementary strands that were not covalently attached to the SNAPP, by performing 2 washes in ION Denaturing Solution (125 mM NaOH, 0.1% Tween-20) with a 5 minute incubation at room temperature for each wash.

The SNAPPS were then washed 2× in Life TEX Buffer (10 mM Tris, 1 mM EDTA, 0.01% Triton X-100). The SNAPPs were then subjected to an ion-based sequencing reaction using the Ion Torrent PGM™ sequencer, as described below:

Sequencing Using the Ion Torrent PGM™ Sequencer

The SNAPPs including the amplified DNA were washed 2× in Annealing Buffer, which includes Gibco brand PBS, pH 7.2 (1.54 mM Potassium Phosphate monobasic, 155.17 mM sodium chloride, 2.71 mM sodium phosphate dibasic) with 0.2% Tween-20.

5 ul of ION sequencing primer (Part number 602-1021-03, as provided in the Nucleotides, Enzyme and Controls Kit, Part number 4462916, of the Ion PGM™ 314 Sequencing Kit, Part No. 4462909; Ion Torrent Systems, which is a subsidiary of Life Technologies Corp., Carlsbad, Calif.) was added to the washed SNAPPs and hybridized in a thermocycler as follows:

95° C. for 2 minutes
37° C. for 2 minutes

Annealed SNAPPs were washed 2× in Annealing Buffer, with approximately 7 µl of buffer left on the SNAPP pellet after the final wash.

1 ul of Ion Sequencing Polymerase (Part number 602-1023-01, as provided in the Nucleotides, Enzyme and Controls Kit, Part number 4462916, of the Ion PGM™ 314 Sequencing Kit, Part No. 4462909; Ion Torrent Systems, a subsidiary of Life Technologies, Carlsbad, Calif.) was added to the SNAPPs and the mixture was incubated for 5 minutes at room temperature.

SNAPPs were gently sonicated for 10 seconds in a water bath to disperse any clumps.

2 ul of 50% glycerol (diluted in Annealing Buffer) was added and the sample was loaded on an Ion Torrent PGM™ 314 sequencing chip from the Ion Sequencing 314 Kit (part number 4462909, Ion Torrent Systems, Life Technologies. Briefly, the chip was primed by addition of 50 ul Annealing Buffer (part number 603-1047-01, included in the PGM Reagents Kit, part number 4465455, Ion Torrent Systems). 10 ul of sample was injected into the port of the chip, and the chip was then centrifuged for 10 minutes. The PGM™ sequencing run was performed using standard nucleotide flow order for 55 cycles.

Using this method, a total of 21 alignments with a minimum of Q17 quality (allows up to 2% error) were generated, representing 1391 mapped bases of DH10b sequence. Included in these sequencing reads were 18 alignments that meet the criteria for Q20 quality (allows only 1% error), representing 956 mapped bases. The longest alignment obtained was 109 bases with Q20 quality (1% error, in this case 1 base mismatch). The longest perfectly mapped read (i.e. error-free read) was 95 bases long.

Example 7

"Double" Walking

In this example, both the forward and reverse primers have a breathable PBS prone to local denaturation at the isothermal amplification conditions of choice. Each PBS thus has a corresponding tendency to reassociate with a new unextended primer. The forward primer is immobilized on a support, and thus the forward PBS, after dissociating from a first forward primer, can rehybridize with a second different forward primer that is immobilized close to the first forward primer. Similarly, the reverse PBS tends to dissociate from a first soluble reverse primer and re-hybridize to a second soluble reverse primer, which is then extended.

The following amplification reaction was done:

Hybridization:

Template at 100 µM total concentration in 1×SSPEt buffer, and pre-denatured by heat (95° C. for 3 minutes) and held on ice. 12 ul was added to each lane. The mix was subjected to 75° C. for 2 min, 50° C. for 1 min, 40° C. for 1 min, 30° C. for 1 min, 25° C. for 2 minutes. The lanes were washed with 0.1×SSPEt (2×1 ml).

Primer Extension:

The following master mix was prepared: 5 µl of 10×NEB Buffer 2; 0.5 µl of 100 mM dNTP; 1 µl of Klenow (NEB 5 u/ul, M0212L); 43.5 µl of dH2O (Total of 50 µl). 12 uL of reaction mix was added to all lanes, and incubated at 37 C for 30 min. Lanes were washed with 2×SSC+0.1% SDS, 1×TMAX (1 ml) and incubated with 1×NEB ThermoPol buffer at 60° C. for 40 min and washed again with 2×SSC+ 0.1% SDS, 1×TMAX (1 ml).

Template Walking:

The following master mix was prepared: 10 µl of 10×NEB ThermoPol Buffer; 2 µl of 100 mM dNTP; 50 µl of soluble primer PE; 40 µl of Bst (NEB 120 u/ul); 47 µl of dH2O (Total of 100 µl). 12 µL master mix was added to each lane and incubated at 60° C. for 30 min. 12 µl of the supernatant was taken out and diluted 1:100, with 5 µl used for Taqman assays. Lanes were washed with 2×SSC+0.1% SDS, 1×TMAX (1 ml). In a HiDi wash (2×12 uL for 5 min) the lanes were washed with 1×TMAX (2×1 ml).

For the TaqMan reactions, a reaction mix was prepared with 10 µl of TaqMan Fast Universal Master Mix, No UNG; 1 µl of 20× primer probe mix; 4 µl of H2O; 5 µl of Stock solution (Total: 20 µl). The mix was subjected to 95° C. (20 sec) and 40 thermocycles (95° C. 3 sec, 60° C. 30 sec), followed by data collection.

Amplification using two breathable primers (an immobilized "forward" primer and a soluble distal "reverse" primer, termed Pe or Pd in Table 2 below) was more efficient than using one breathable primer alone.

TABLE 2

|  | Cq | Supernatant | Release | Average Copy/µm$^2$ |
|---|---|---|---|---|
| Pc Conc.(uM) | 0.8 | 20.2 | 14.9 | 334 |
| Pd conc. (uM) | 0.8 | 20.0 | 14.3 | 517 |

TABLE 2-continued

|  | Cq | Supernatant | Release | Average Copy/$\mu m^2$ |
|---|---|---|---|---|
| Pe Conc. (uM) | 0.2 | 10.0 | 11.4 | 3357 |
|  | 0.3 | 8.3 | 11.4 | 3413 |
|  | 0.4 | 7.9 | 11.3 | 3601 |
|  | 0.5 | 7.8 | 10.9 | 4526 |

Those skilled in the art will recognize, or be able to ascertain using no more than routine experimentation, many equivalents to the specific embodiments of the invention described herein. The scope of the present invention is not intended to be limited to the above Description.

Unless otherwise apparent from the context, any feature can be claimed in combination with any other, or be claimed as not present in combination with another feature. A feature can be any piece of information that can characterize an invention or can limit the scope of a claim, for example any variation, step, feature, property, composition, method, step, degree, level, component, material, substance, element, mode, variable, aspect, measure, amount, option, embodiment, clause, descriptive term, claim element or limitation.

Generally, features described herein are intended to be optional unless explicitly indicated to be necessary in the specification. Non-limiting examples of language indicating that a feature is regarded as optional in the specification include terms such as "variation," "where," "while," "when," "optionally," "include," "preferred," "especial," "recommended," "advisable," "particular," "should," "alternative," "typical," "representative," "various," "such as," "the like," "can," "may," "example," "embodiment," or "aspect," "in some," "example," "exemplary", "instance", "if" or any combination and/or variation of such terms.

Any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X.

Non-limiting examples of exclusive or negative terms include "only," "solely," "consisting of," "consisting essentially of," "alone," "without", "in the absence of (e.g., other items of the same type, structure and/or function)" "excluding," "not including", "not", "doesn't", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Furthermore, it is to be understood that the inventions encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

All publications and patents cited in this specification are herein incorporated by reference as if each individual publication or patent were specifically and individually indicated to be incorporated by reference. Genbank records referenced by GID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

What is claimed:

1. A method for paired end sequencing comprising:
   (a) conducting a forward sequencing reaction on a template polynucleotide attached to a surface and having at least one cleavable scissile moiety by (i) hybridizing a first primer to the template polynucleotide, (ii) extending the first primer by conducting primer extension reactions by polymerase-catalyzed successive nucleotide incorporations and forming a first extension strand hybridized to the template polynucleotide, and (iii) identifying the incorporated nucleotides in the first extension strand;
   (b) inducing cross-linking between a nucleoside of the template polynucleotide and a nucleoside of the first extension strand;
   (c) cleaving the template polynucleotide by reacting the scissile moiety with heat, irradiation, at least one chemical, or at least one enzyme, to form a truncated template polynucleotide and forming a terminal 3' phosphate group, converting the terminal 3' phosphate group to an —OH group, and removing a portion of the cleaved template polynucleotide; and
   (d) conducting a reverse sequencing reaction on the first extension strand by extending the terminal 3' OH group on the truncated template polynucleotide with primer extension reactions by polymerase-catalyzed successive nucleotide incorporations and forming a second extension strand, and (iii) identifying the incorporated nucleotides in the second extension strand.

2. The method of claim 1, wherein the 5' end of the template polynucleotide is attached to a surface.

3. The method of claim 1, wherein the template polynucleotide further comprises a cross linking moiety.

4. The method of claim 3, wherein the cross linking moiety comprises a 3-cyanovinylcarbazole nucleoside.

5. The method of claim 1, wherein the cleavable scissile moiety comprise a uracil base.

6. The method of claim 1, wherein an appropriate wavelength of irradiation comprises 366 nm.

7. The method of claim 1, wherein the at least one enzyme that cleaves the scissile moiety comprise a glycosylase.

8. The method of claim 1, wherein the at least one enzyme that cleaves the scissile moiety comprises a lyase.

9. The method of claim 1, wherein the terminal 3' phosphate group is converted to an —OH group by a kinase enzyme.

10. The method of claim 1, wherein the portion of the cleaved template polynucleotide is removed by denaturation.

11. A method for paired end sequencing comprising:
    (a) conducting a forward sequencing reaction on a template polynucleotide attached to a surface and having at least one cross linking moiety and at least one cleavable scissile moiety by (i) hybridizing a first primer to the template polynucleotide, (ii) extending the first primer by conducting primer extension reactions by polymerase-catalyzed successive nucleotide incorporations and forming a first extension strand hybridized to the template polynucleotide, and (iii) identifying the incorporated nucleotides in the first extension strand;

(b) inducing cross linking between a nucleoside of the template polynucleotide and a nucleoside of the first extension strand with a heat, chemical or photochemical condition;

(c) cleaving the template polynucleotide by reacting the scissile moiety with heat, irradiation, at least one chemical, or at least one enzyme, to form a truncated template polynucleotide and forming a terminal 3' phosphate group, converting the terminal 3' phosphate group to an —OH group, and removing a portion of the cleaved template polynucleotide; and (d) conducting a reverse sequencing reaction on the first extension strand by extending the terminal 3' OH group on the truncated template polynucleotide with primer extension reactions by polymerase-catalyzed successive nucleotide incorporations and forming a second extension strand, and (iii) identifying the incorporated nucleotides in the second extension strand.

12. The method of claim 11, wherein the 5' end of the template polynucleotide is attached to a surface.

13. The method of claim 11, wherein the cross linking moiety comprises a 3-cyanovinylcarbazole nucleoside.

14. The method of claim 11, wherein the cleavable moiety comprise a uracil base.

15. The method of claim 11, wherein an appropriate wavelength of irradiation comprises 366 nm.

16. The method of claim 11, wherein the at least one enzyme that cleaves the scissile moiety comprise a glycosylase.

17. The method of claim 11, wherein the at least one enzyme that cleaves the scissile moiety comprises a lyase.

18. The method of claim 11, wherein the terminal 3' phosphate group is converted to an —OH group by a kinase enzyme.

19. The method of claim 11, wherein the portion of the cleaved template polynucleotide is removed by denaturation.

* * * * *